United States Patent [19]
Yoon

[11] Patent Number: 5,645,076
[45] Date of Patent: Jul. 8, 1997

[54] AUTOMATIC RETRACTABLE SAFETY PENETRATING INSTRUMENT

[76] Inventor: InBae Yoon, 2101 Highland Ridge Dr., Phoenix, Md. 21131

[21] Appl. No.: 406,217

[22] Filed: Mar. 15, 1995

Related U.S. Application Data

[62] Division of Ser. No. 196,027, Feb. 14, 1994, which is a division of Ser. No. 945,177, Sep. 15, 1992, which is a continuation-in-part of Ser. No. 745,071, Aug. 14, 1991, abandoned, Ser. No. 800,507, Nov. 27, 1991, abandoned, Ser. No. 805,506, Dec. 6, 1991, Pat. No. 5,330,432, Ser. No. 808,325, Dec. 16, 1991, Pat. No. 5,324,268, Ser. No. 848,838, Mar. 10, 1992, Pat. No. 5,445,614, Ser. No. 868,578, Apr. 15, 1992, Pat. No. 5,336,176, Ser. No. 929,338, Aug. 14, 1992, Pat. No. 5,360,405, and Ser. No. 868,566, Apr. 15, 1992, Pat. No. 5,320,610.

[51] Int. Cl.$^6$ .................................................. A61B 10/00
[52] U.S. Cl. ................................... 128/754; 604/165
[58] Field of Search ............................ 128/751, 752, 128/753, 754; 606/658, 184; 604/164–169, 272–274

[56] References Cited

U.S. PATENT DOCUMENTS

| | | |
|---|---|---|
| Re. 32,922 | 5/1989 | Levin et al. |
| 1,527,291 | 2/1925 | Zorraquin . |
| 2,496,111 | 1/1950 | Turkel . |
| 2,623,521 | 12/1952 | Shaw . |
| 2,630,803 | 3/1953 | Baran . |
| 4,230,123 | 10/1980 | Hawkins, Jr. .......... 128/753 |
| 4,254,762 | 3/1981 | Yoon . |
| 4,345,589 | 8/1982 | Hiltebrandt . |
| 4,442,836 | 4/1984 | Meinecke et al. |
| 4,488,545 | 12/1984 | Shen . |
| 4,503,856 | 3/1985 | Cornell et al. |
| 4,535,773 | 8/1985 | Yoon . |
| 4,559,041 | 12/1985 | Razi . |
| 4,601,710 | 7/1986 | Moll . |
| 4,627,841 | 12/1986 | Dorr . |
| 4,654,030 | 3/1987 | Moll et al. |
| 4,670,008 | 6/1987 | Von Albertini . |
| 4,677,979 | 7/1987 | Burns . |
| 4,747,831 | 5/1988 | Kulli . |
| 4,802,275 | 2/1989 | Haber et al. |
| 4,817,603 | 4/1989 | Turner et al. |
| 4,869,717 | 9/1989 | Adair . |
| 4,889,117 | 12/1989 | Stevens . |
| 4,900,307 | 2/1990 | Kulli . |
| 4,902,280 | 2/1990 | Lander . |
| 4,906,236 | 3/1990 | Alberts et al. |
| 4,931,042 | 6/1990 | Holmes et al. |
| 4,943,280 | 7/1990 | Lander . |
| 4,946,446 | 8/1990 | Vadher . |
| 4,955,870 | 9/1990 | Ridderheim et al. |
| 4,966,593 | 10/1990 | Lennox . |
| 4,973,316 | 11/1990 | Dysarz . |
| 4,994,042 | 2/1991 | Vadher . |
| 4,994,068 | 2/1991 | Hufnagle . |
| 5,024,665 | 6/1991 | Kaufman . |
| 5,026,388 | 6/1991 | Ingaiz . |
| 5,030,206 | 7/1991 | Lander . |
| 5,053,016 | 10/1991 | Lander . |
| 5,061,251 | 10/1991 | Juhasz . |

(List continued on next page.)

FOREIGN PATENT DOCUMENTS

| | | |
|---|---|---|
| 2544262 | 4/1977 | Germany . |
| 1435246 | 11/1988 | U.S.S.R. . |

*Primary Examiner*—Max Hindenburg
*Assistant Examiner*—Pamela L. Wingood

[57] ABSTRACT

An automatic retractable safety penetrating instrument for introduction of sleeves, such as portal sleeves, cannulas and catheters, into anatomical cavities by means of penetrating members, such as solid tip trocars, other solid configuration obturators and cannulated penetrating members, such as needles, include locking and releasing mechanisms for automatic retraction of the penetrating member into the sleeve upon the sleeve entering the anatomical cavity. Various locking and releasing mechanisms are utilized for disposition in the penetrating member hub, in the shaft of the penetrating member or partially in the shaft and the hub, and the penetrating member can be made of telescoping distal and shaft sections to minimize the length of the penetrating member hub.

4 Claims, 21 Drawing Sheets

U.S. PATENT DOCUMENTS

| | | |
|---|---|---|
| 5,066,288 | 11/1991 | Deniega et al. . |
| 5,104,382 | 4/1992 | Brinkerhoff et al. . |
| 5,104,383 | 4/1992 | Shichman . |
| 5,114,407 | 5/1992 | Burbank . |
| 5,116,353 | 5/1992 | Green . |
| 5,127,909 | 7/1992 | Shichman . |
| 5,152,754 | 10/1992 | Plyley et al. . |
| 5,158,552 | 10/1992 | Borgia et al. . |
| 5,207,647 | 5/1993 | Phelps . |
| 5,224,470 | 7/1993 | Schnepp-Pesch et al. ............. 128/753 |
| 5,226,891 | 7/1993 | Bushatz et al. . |
| 5,290,243 | 3/1994 | Chodorow et al. . |
| 5,290,304 | 3/1994 | Storace . |
| 5,295,993 | 3/1994 | Green . |
| 5,312,354 | 5/1994 | Allen et al. . |
| 5,318,580 | 6/1994 | Gresl, Jr. . |
| 5,318,585 | 6/1994 | Guy et al. . |
| 5,320,610 | 6/1994 | Yoon . |
| 5,324,268 | 6/1994 | Yoon . |
| 5,342,382 | 8/1994 | Brinkerhoff et al. . |

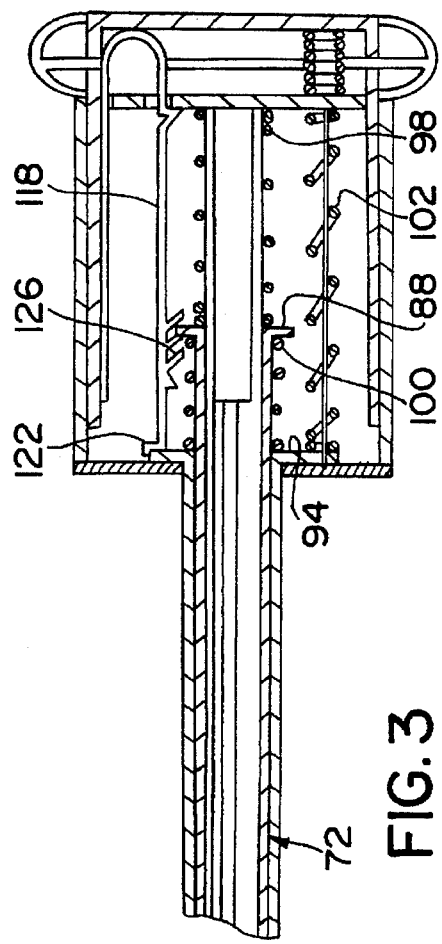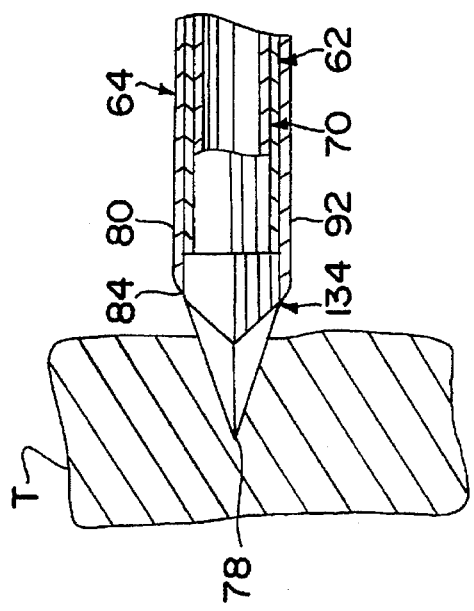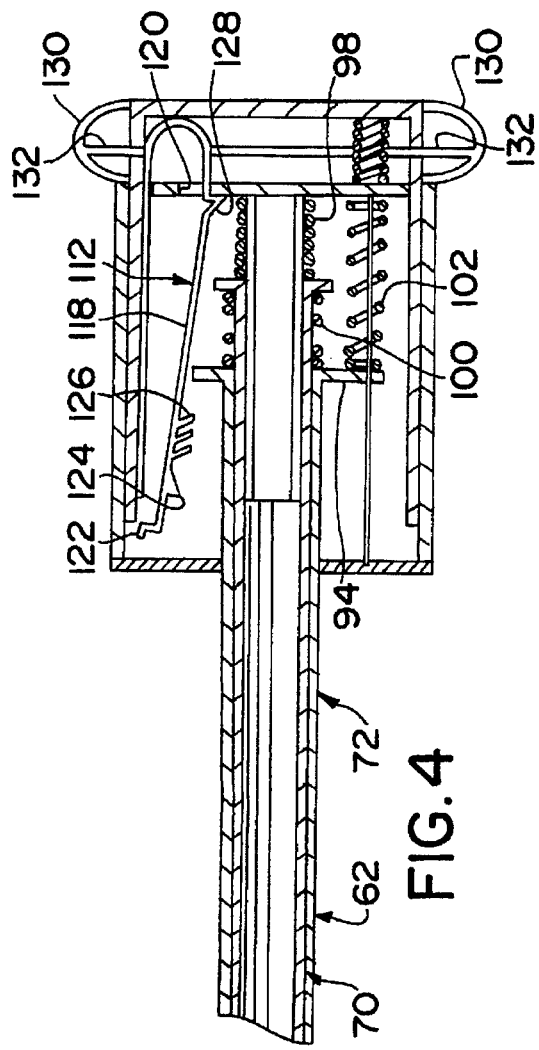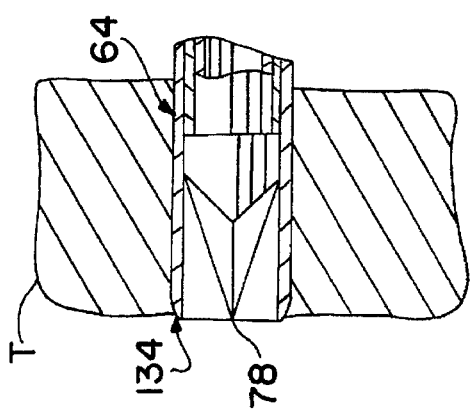
FIG. 3
FIG. 4

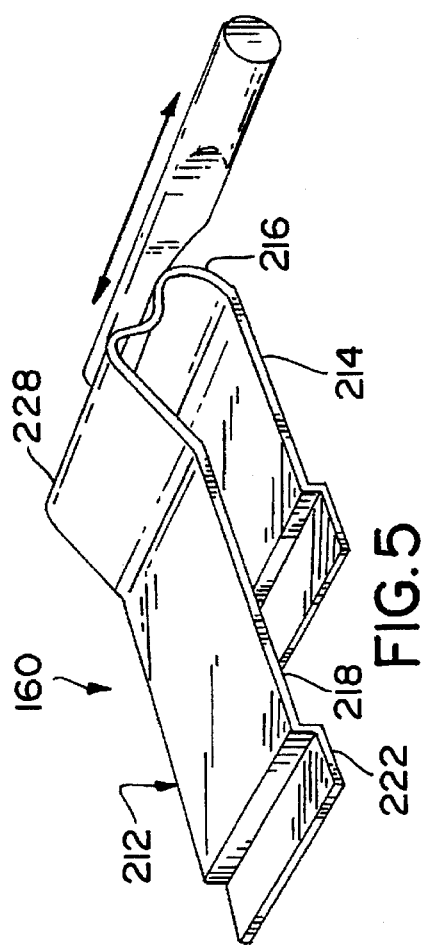
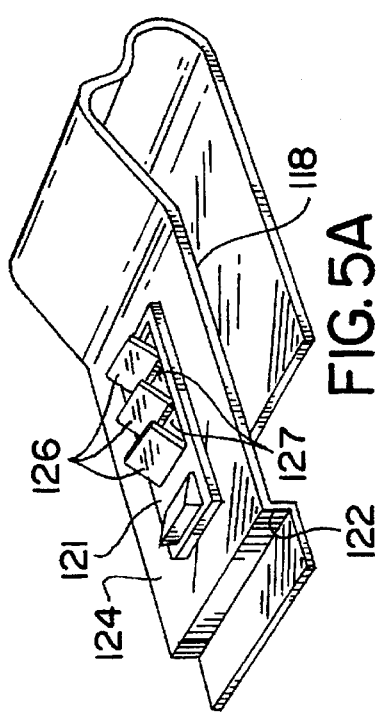
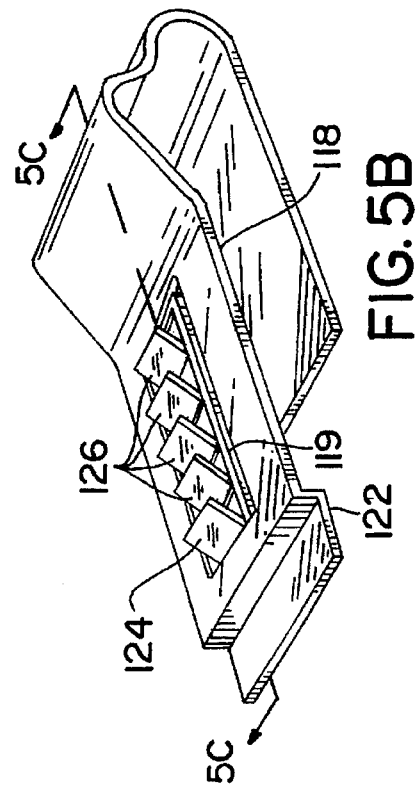
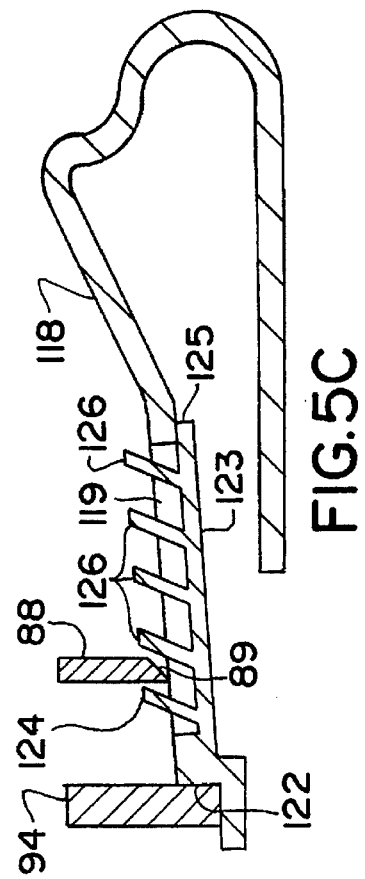

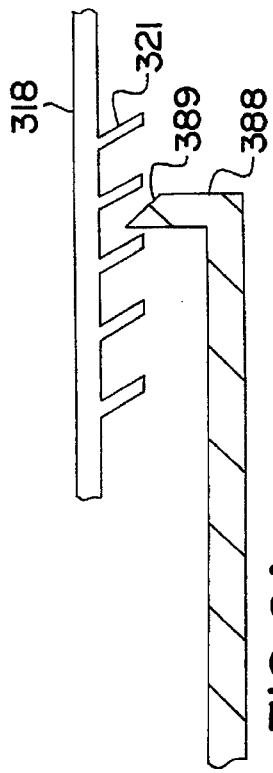
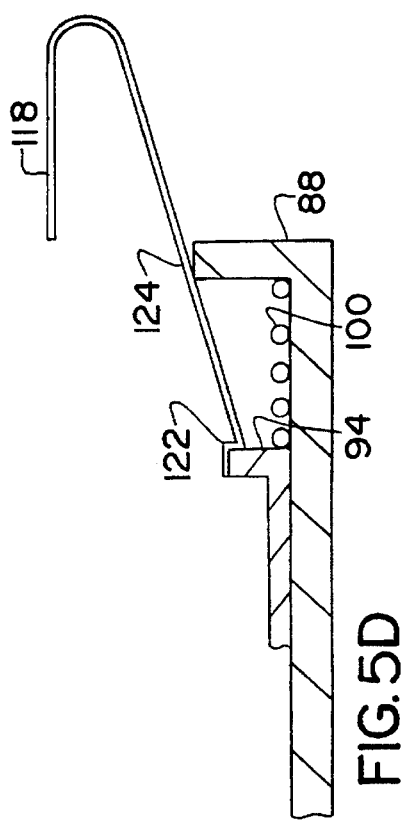
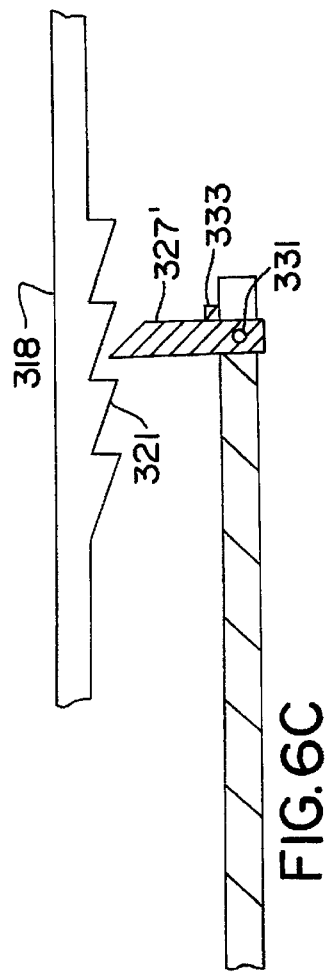
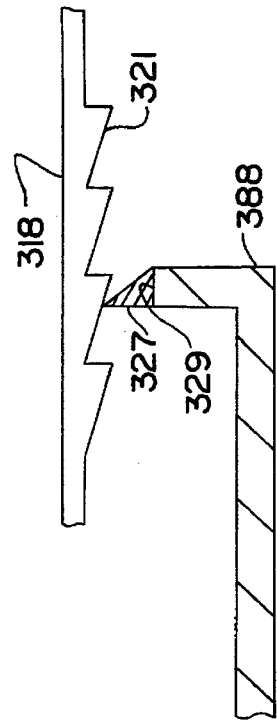
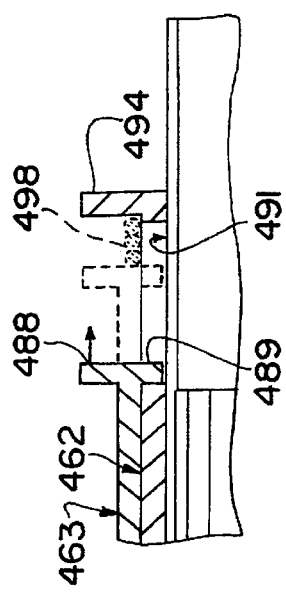

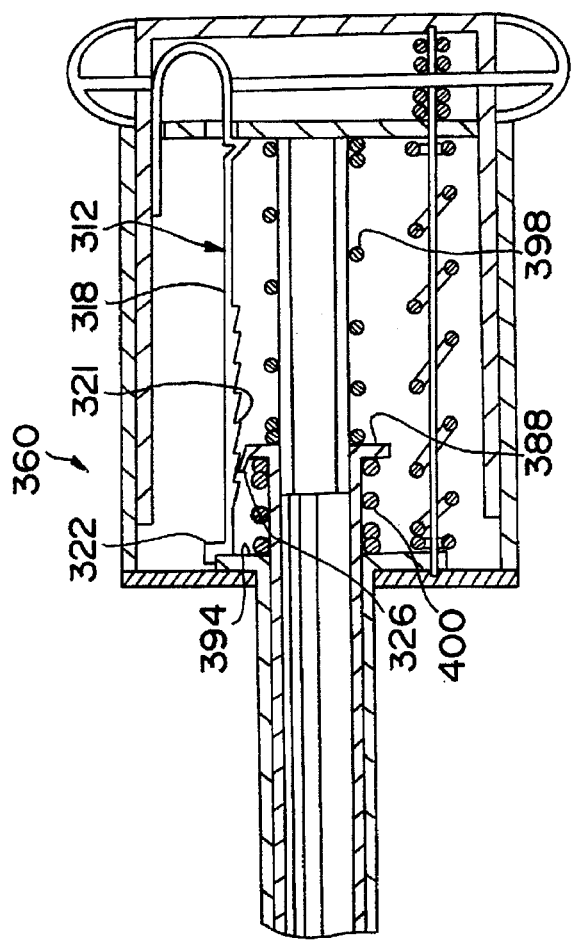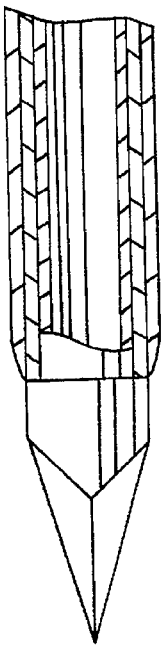
FIG. 6
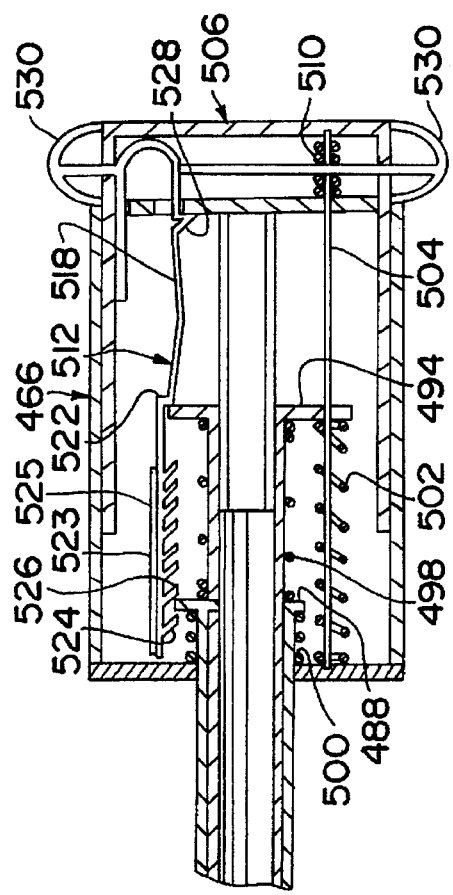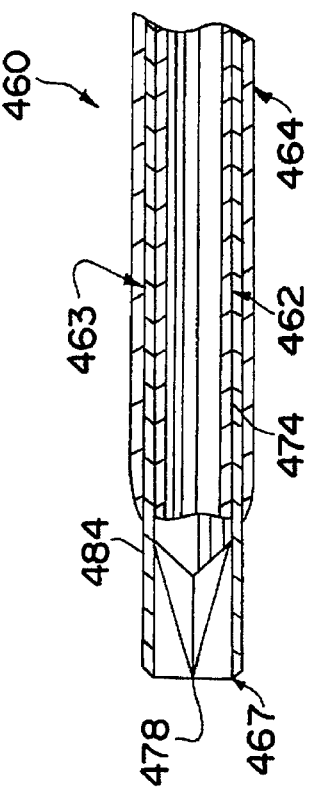
FIG. 7

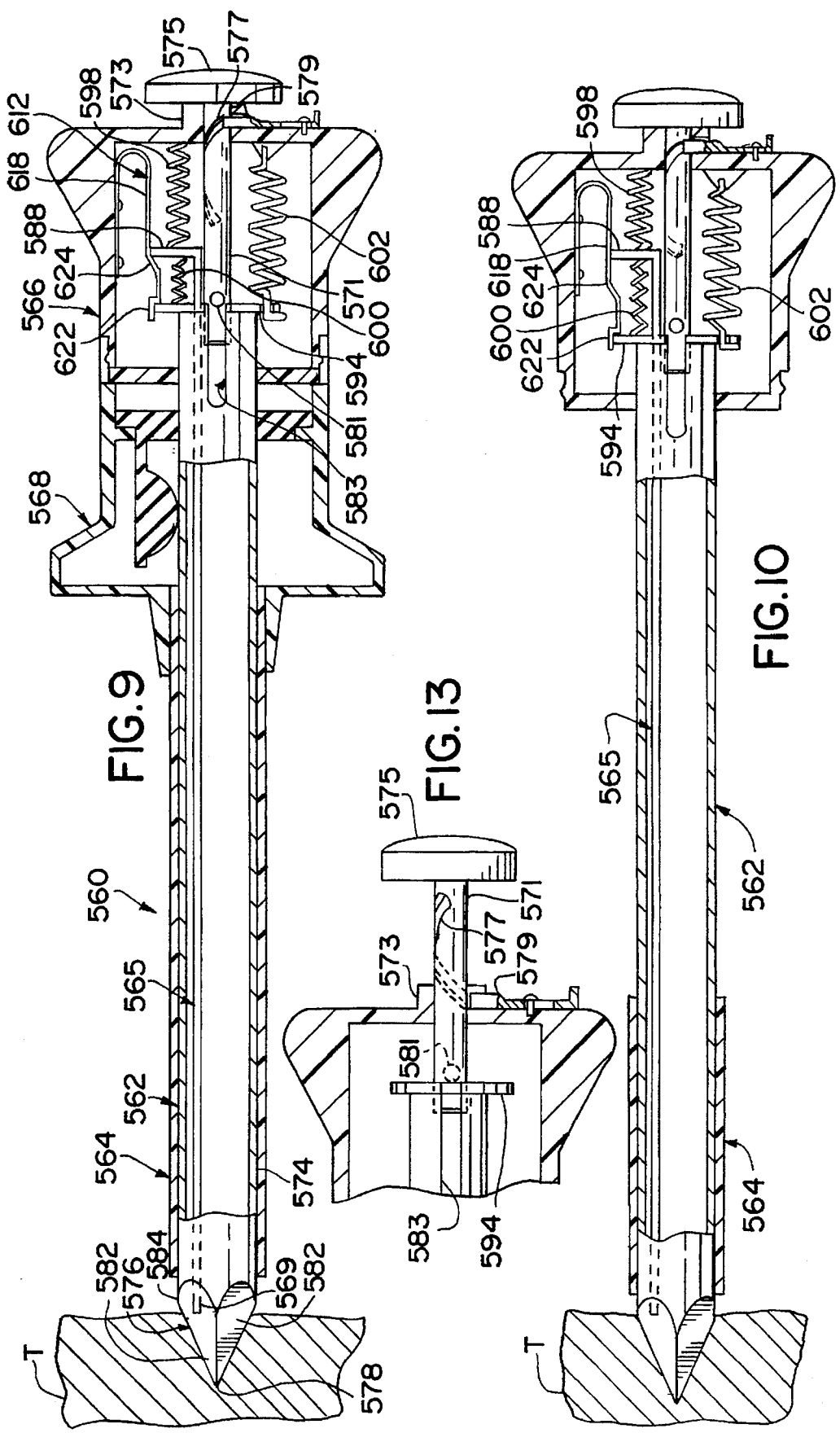

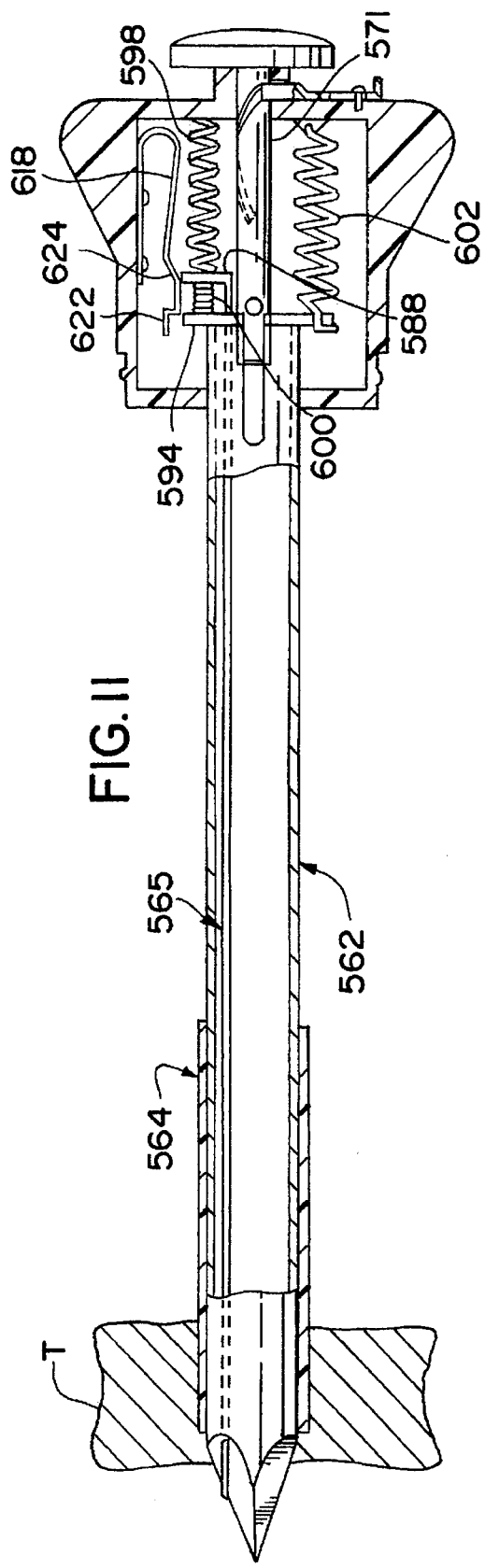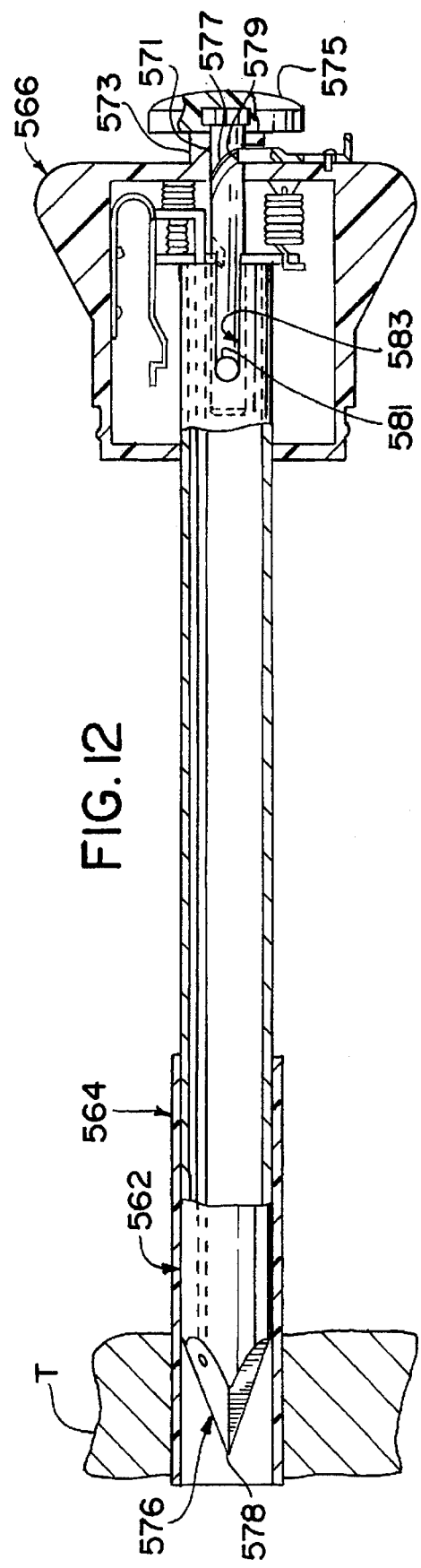

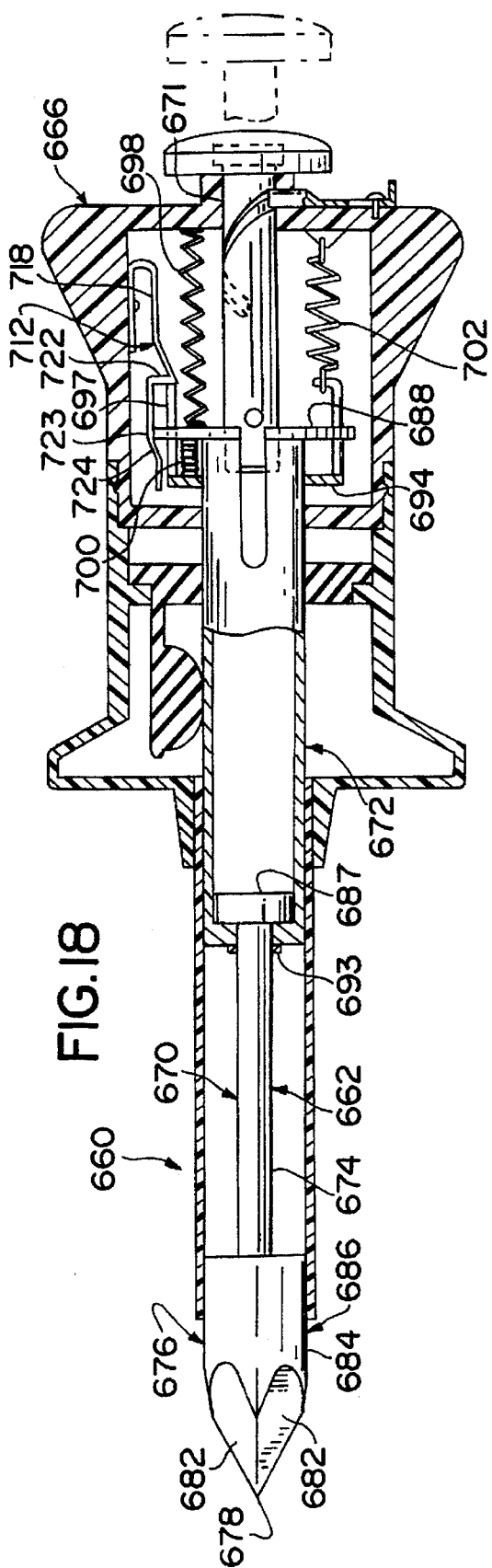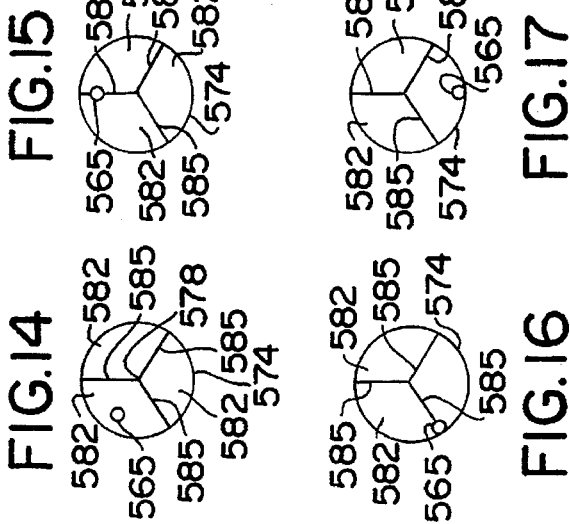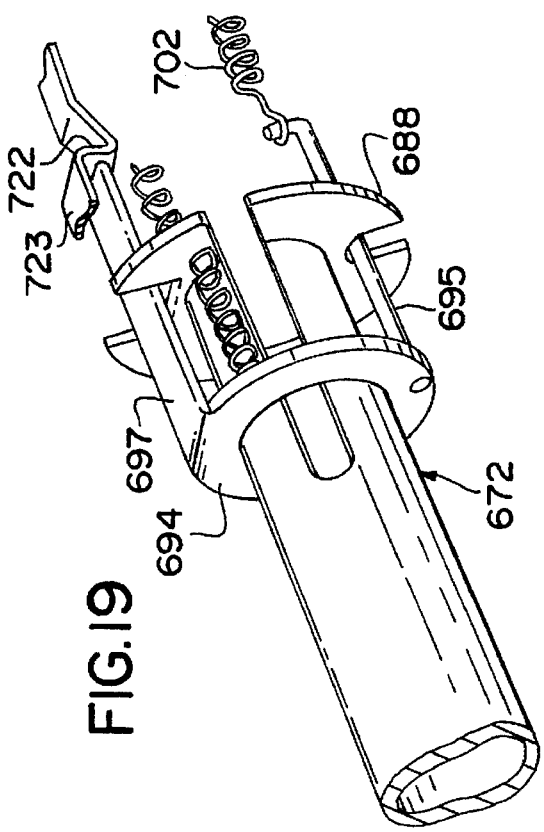

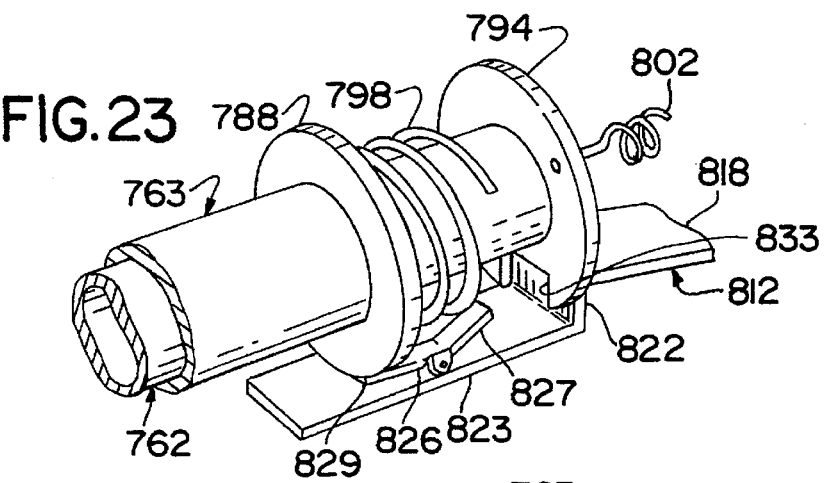
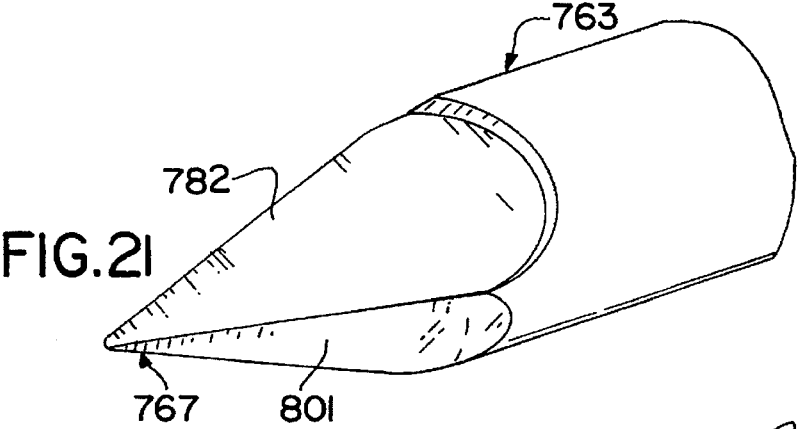
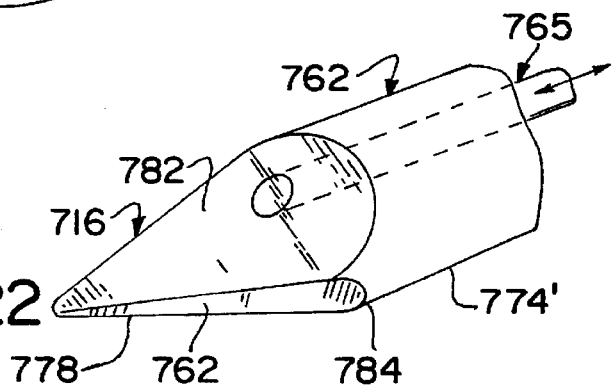
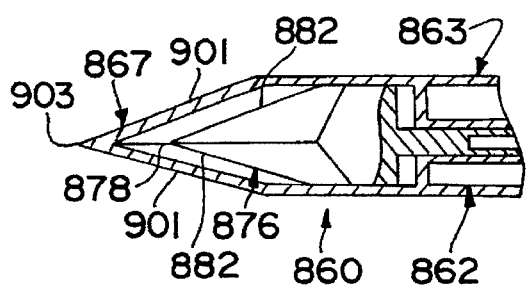
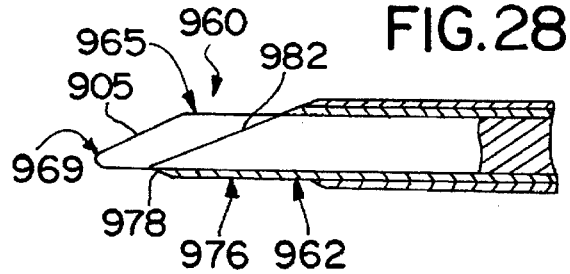

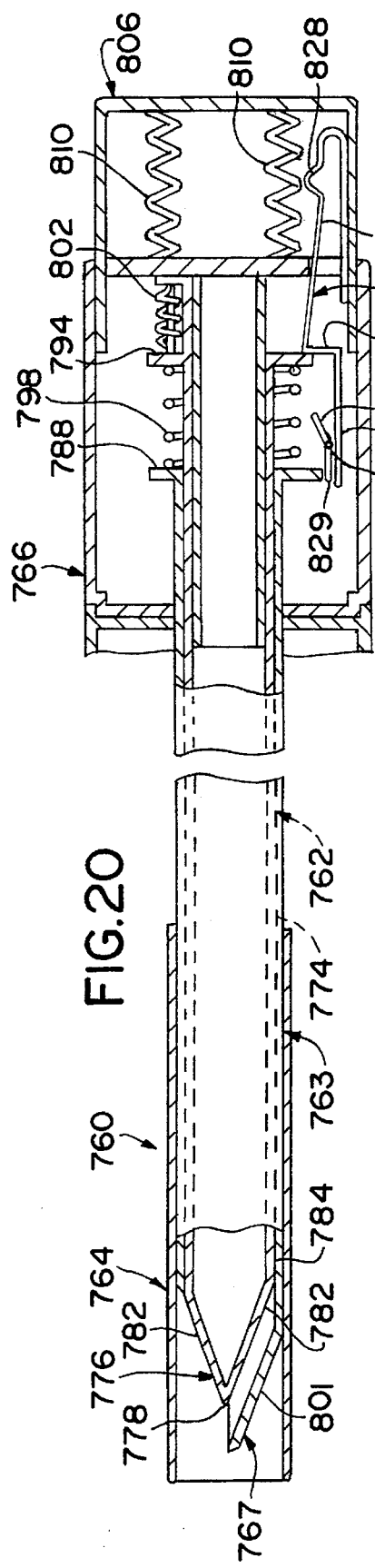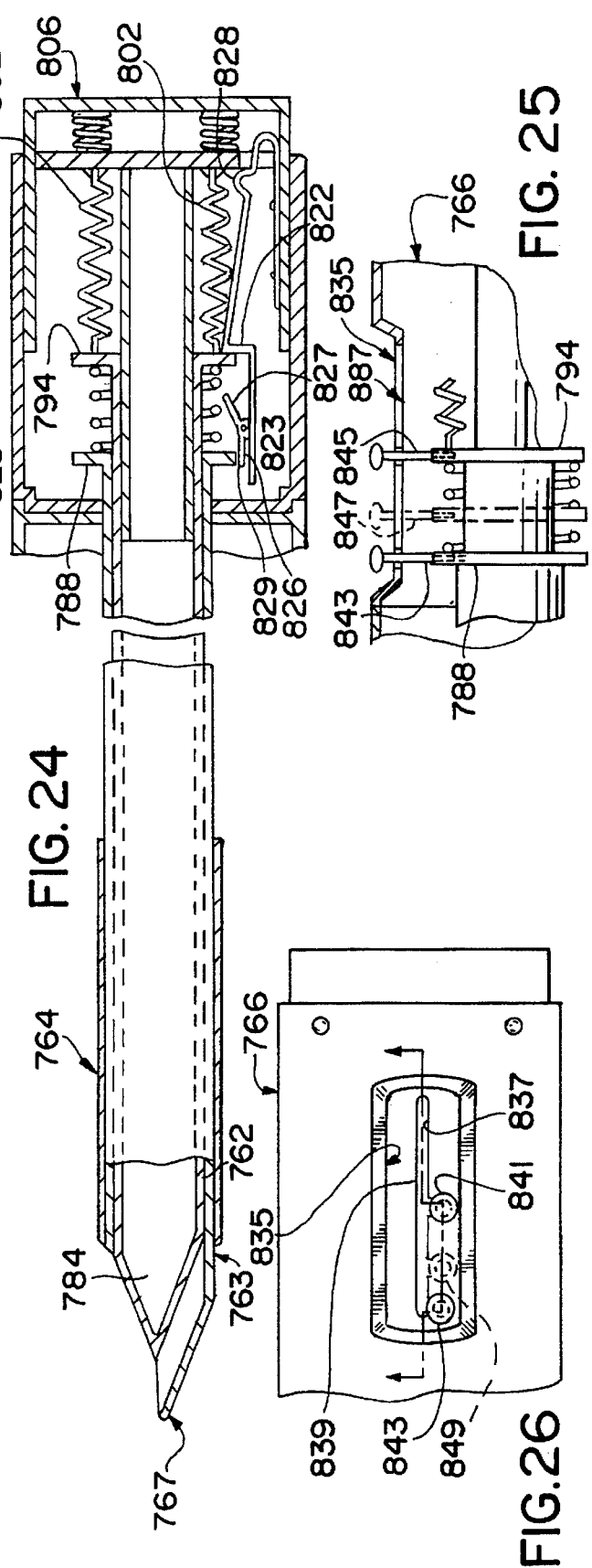

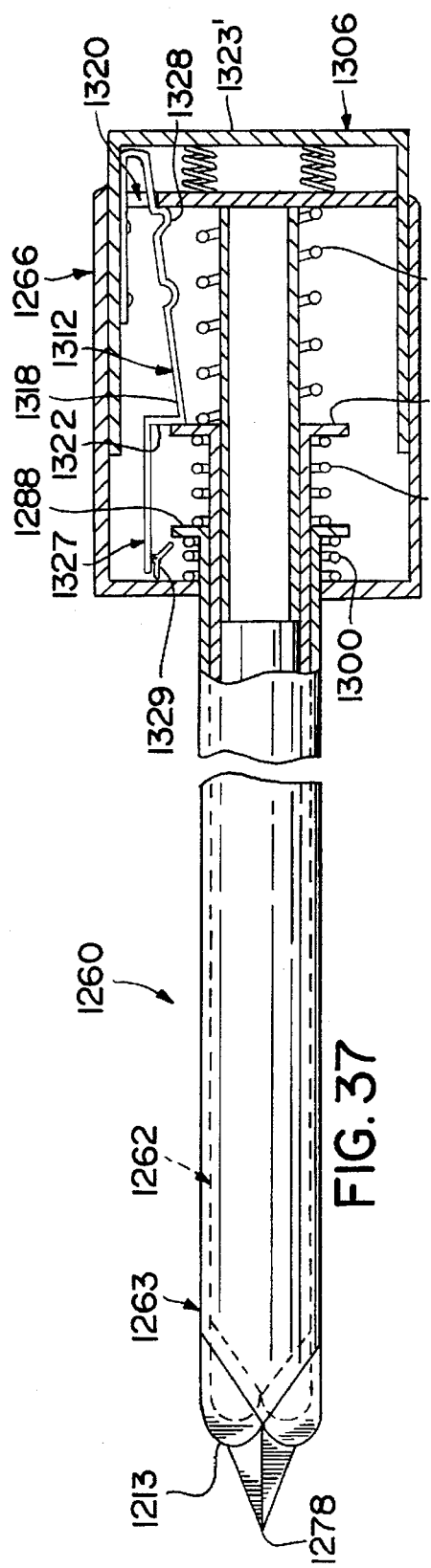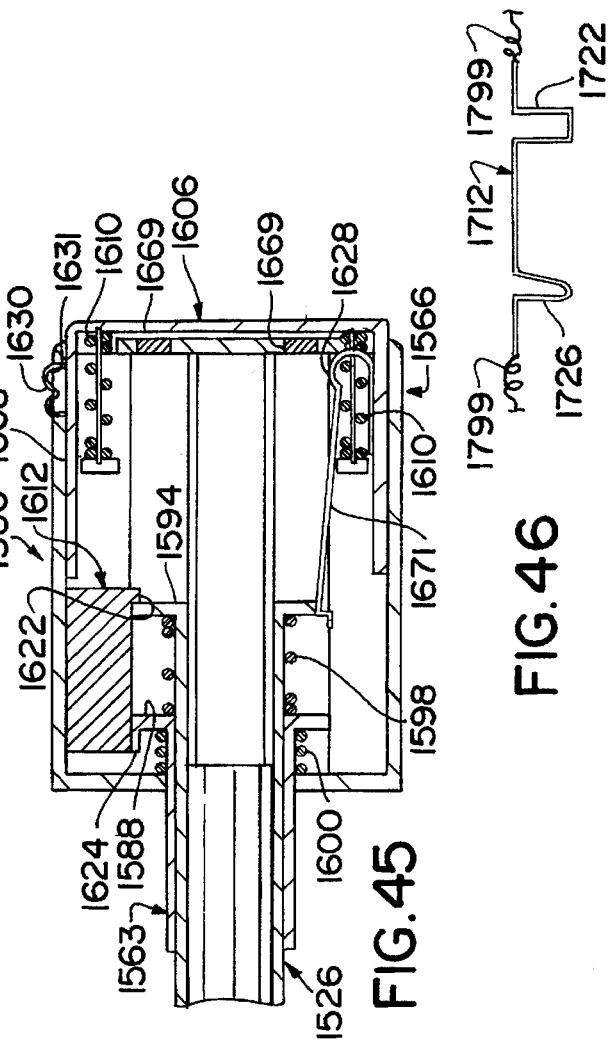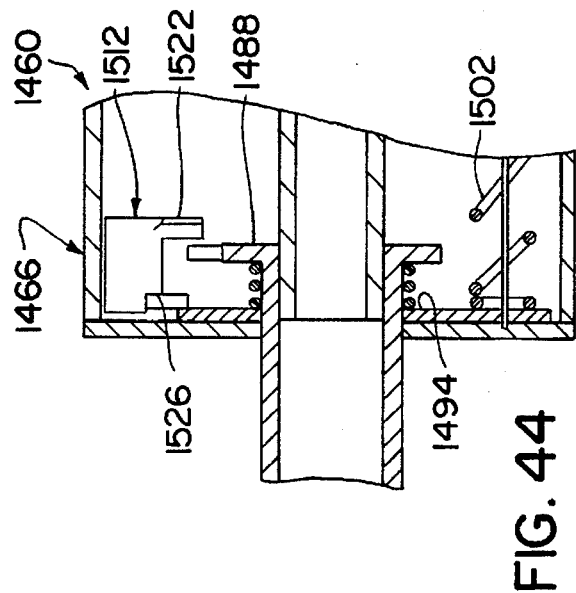

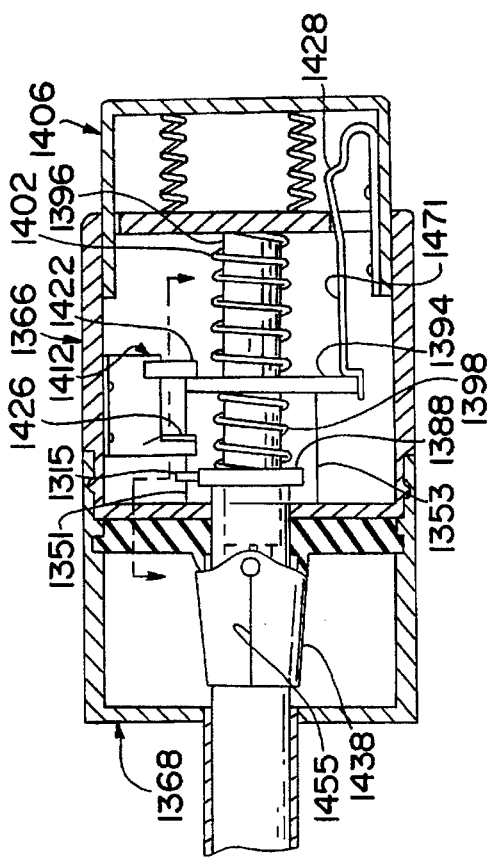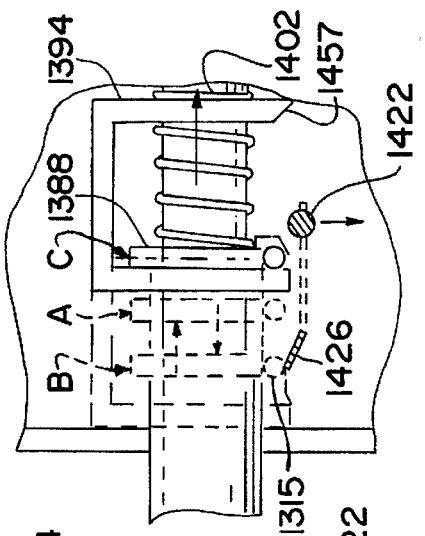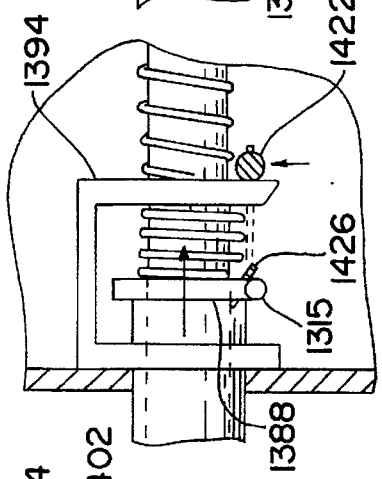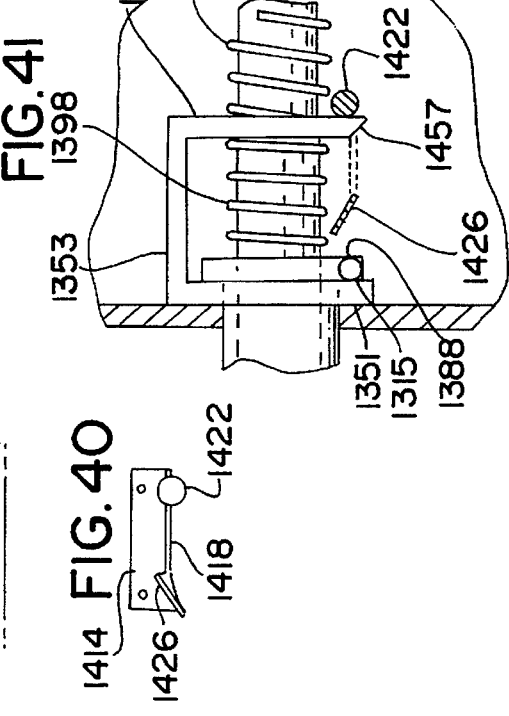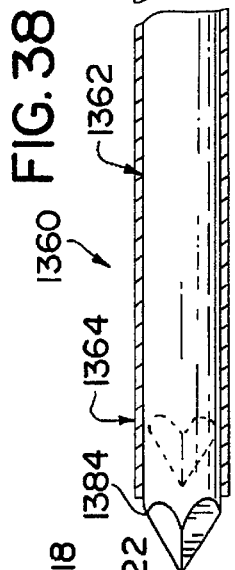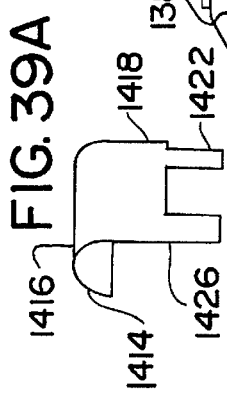

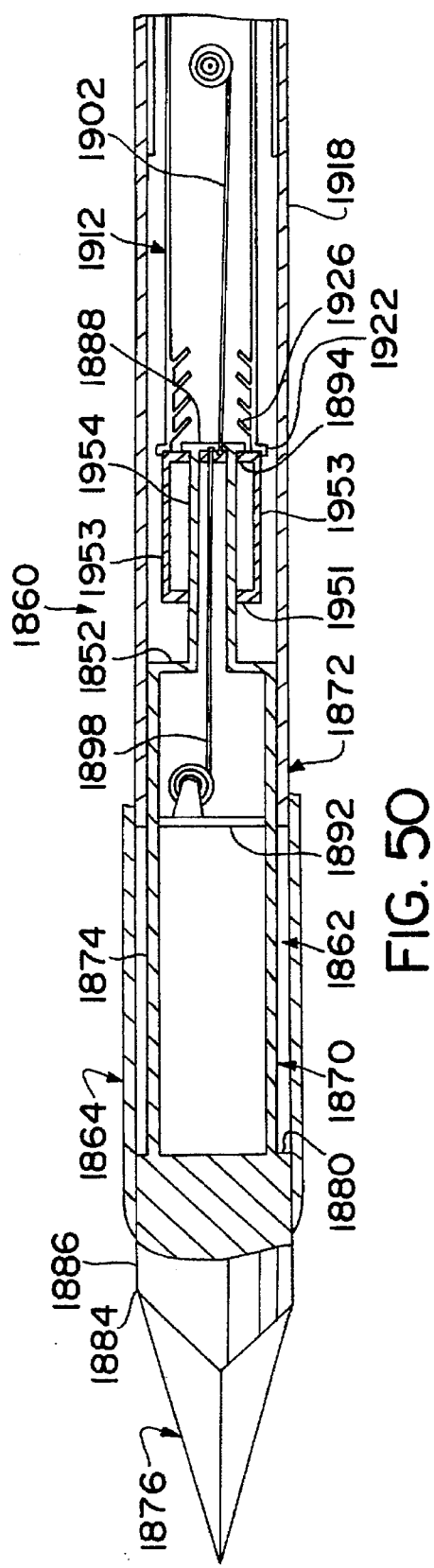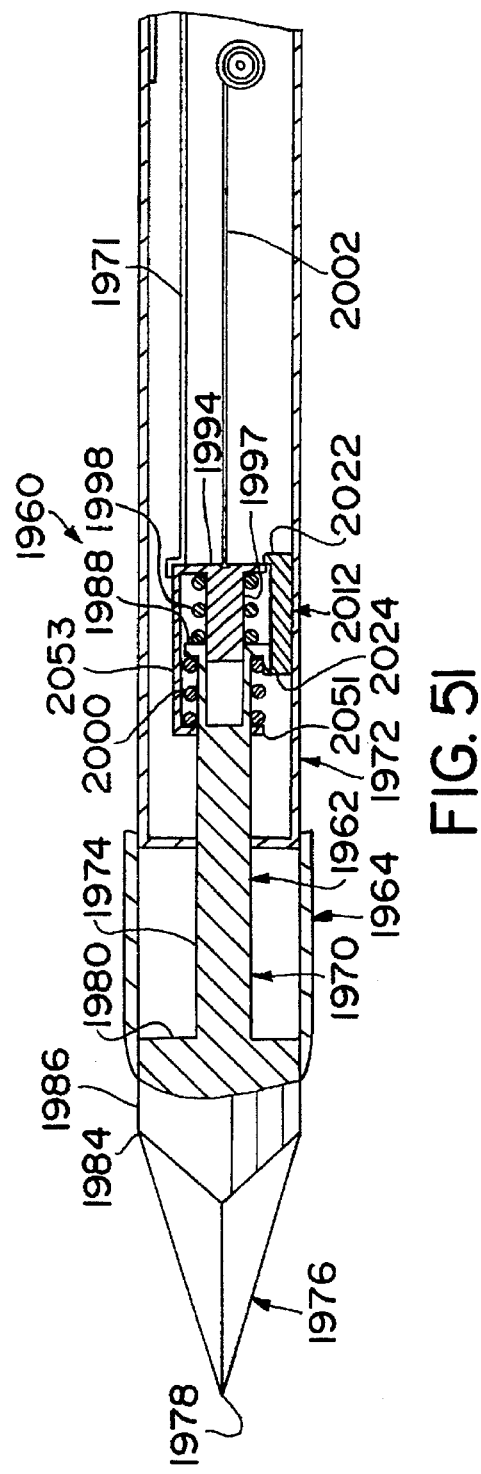

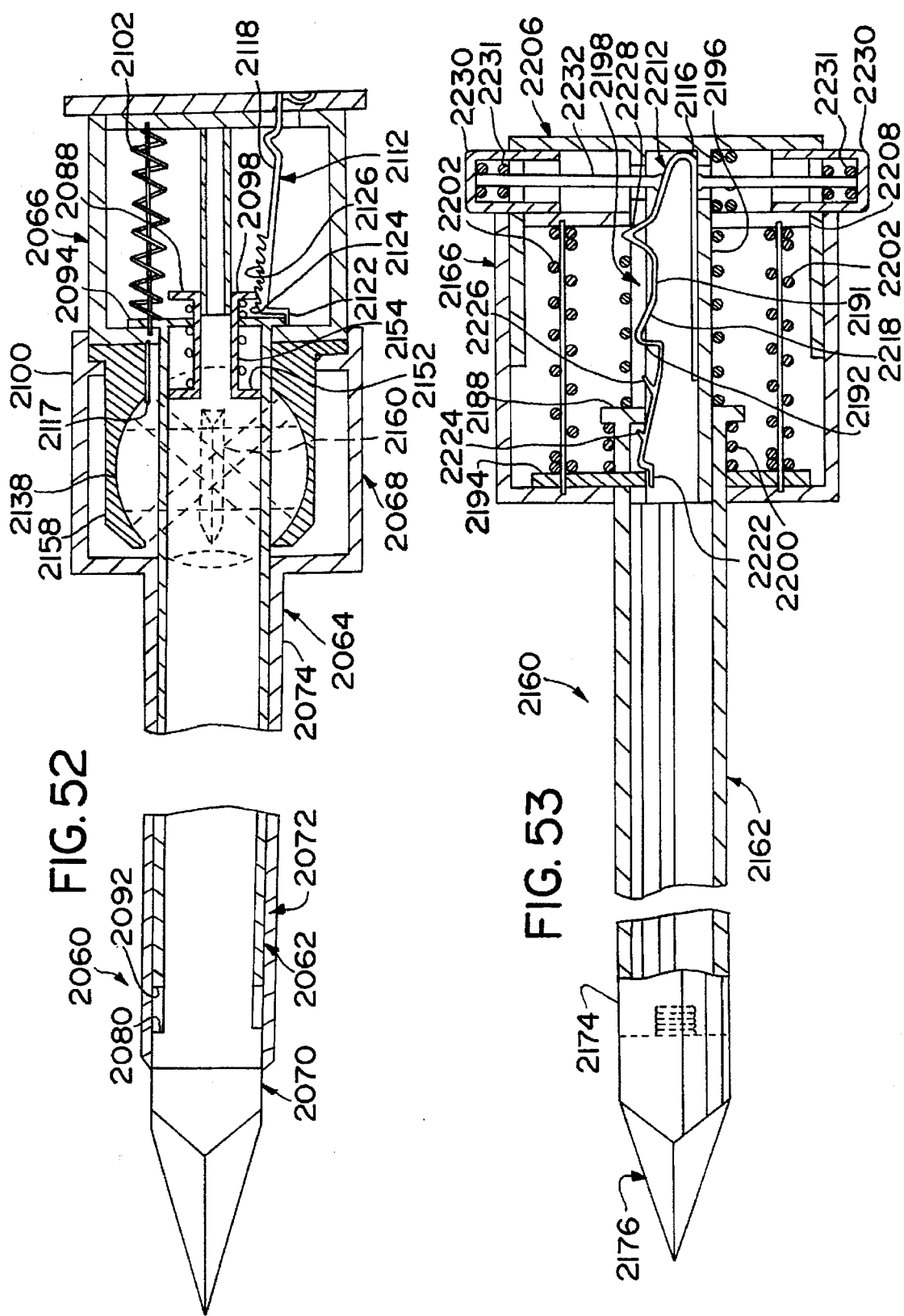

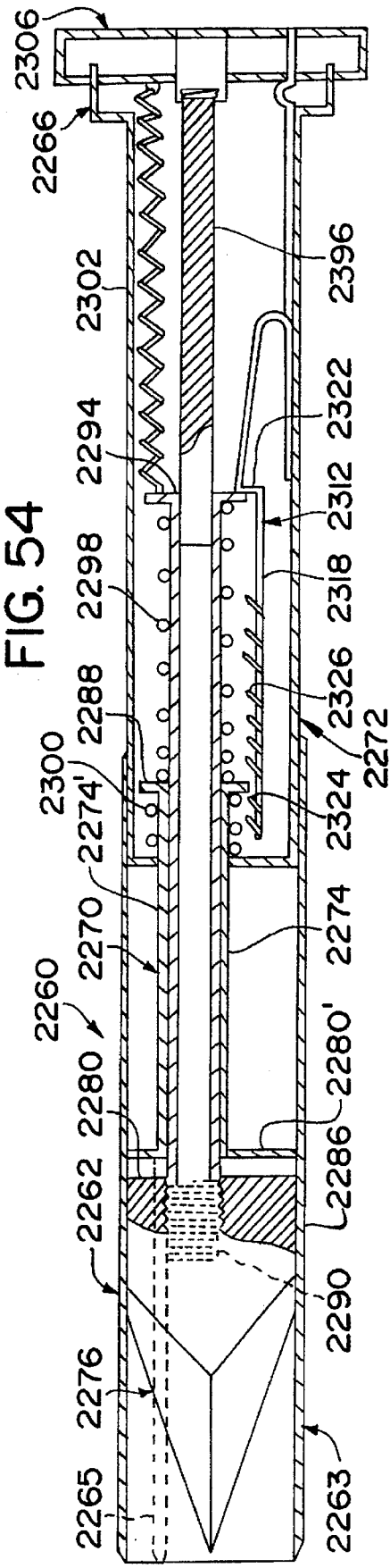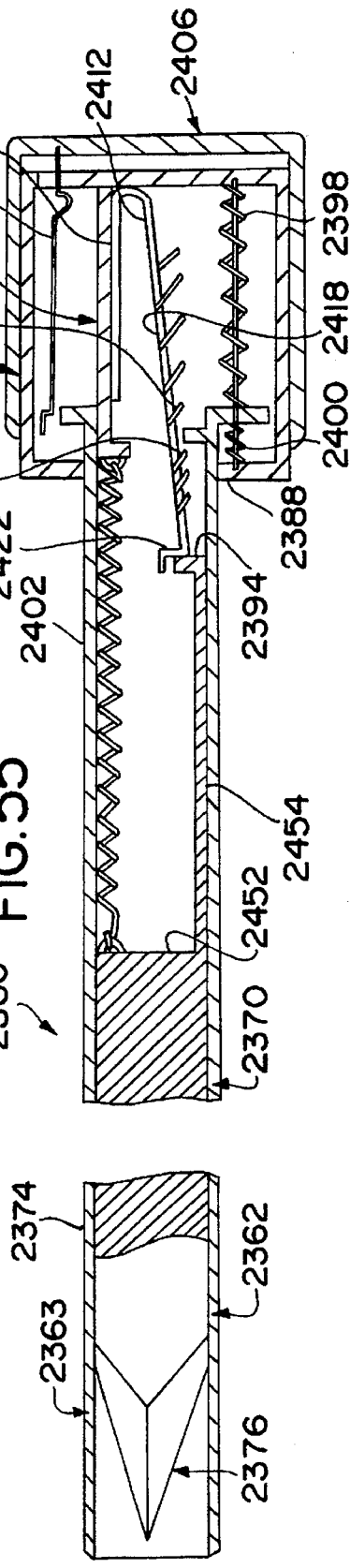

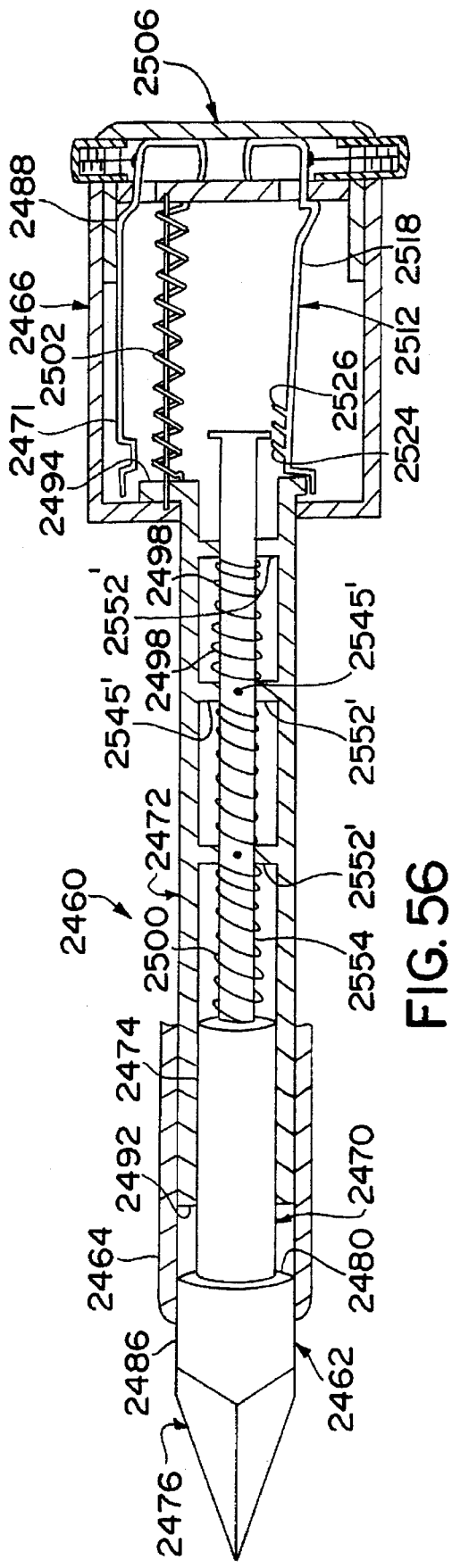
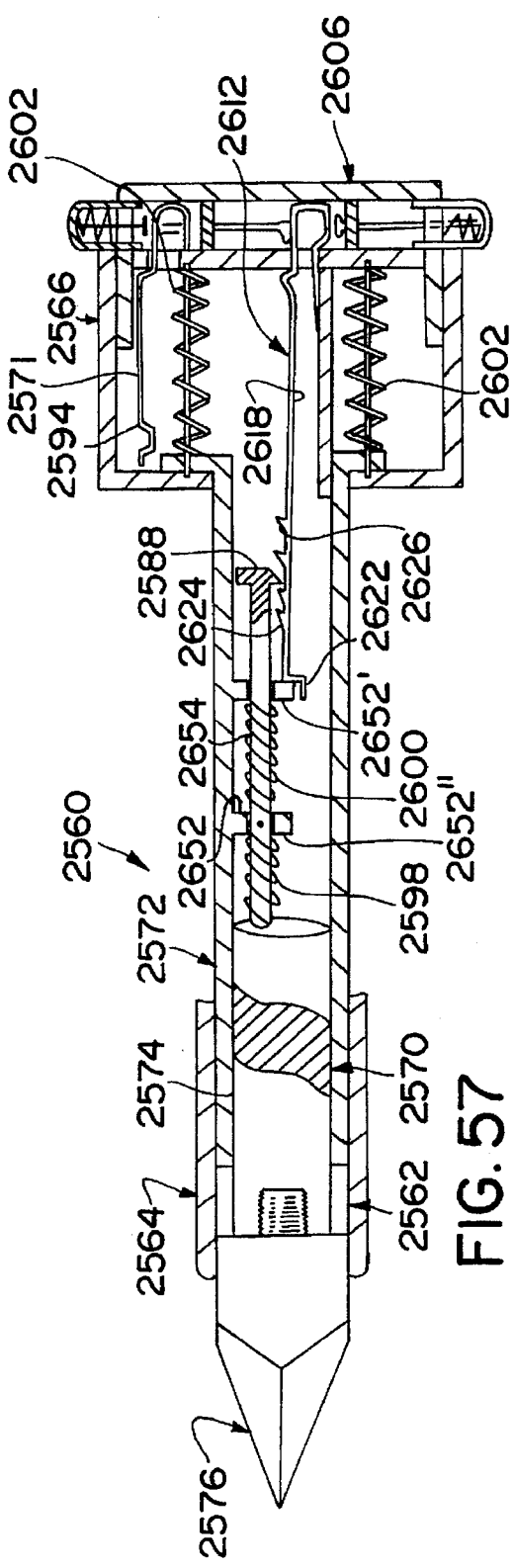
FIG. 56
FIG. 57

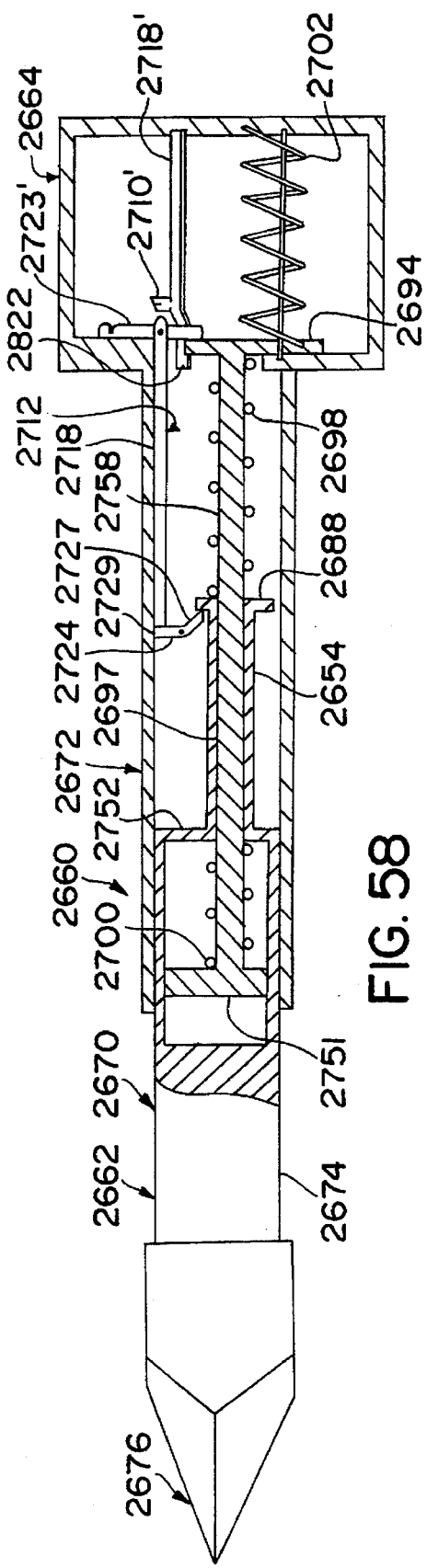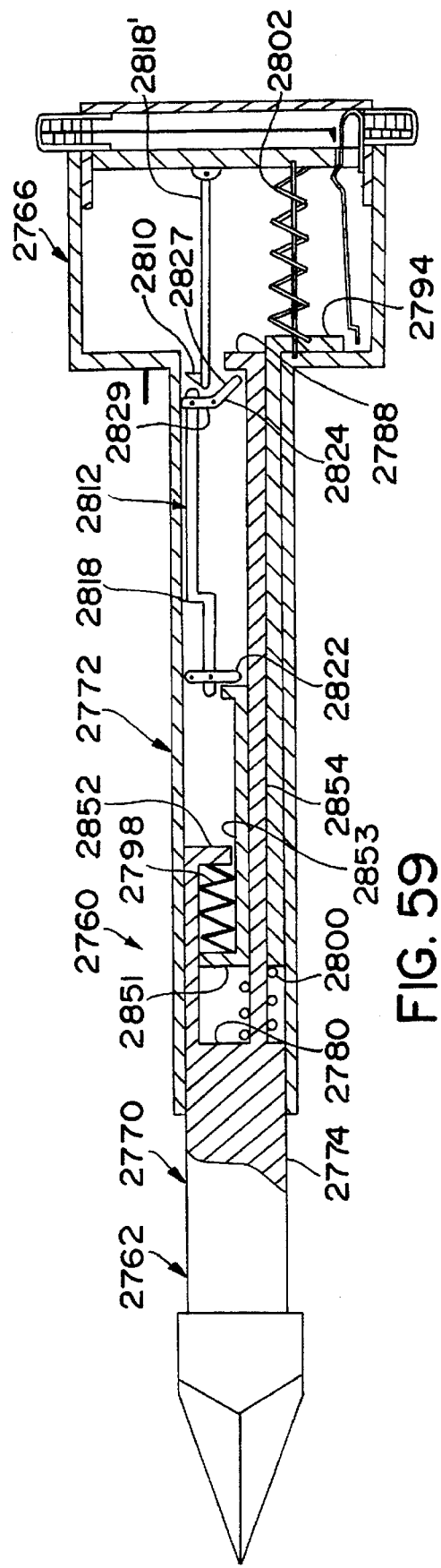

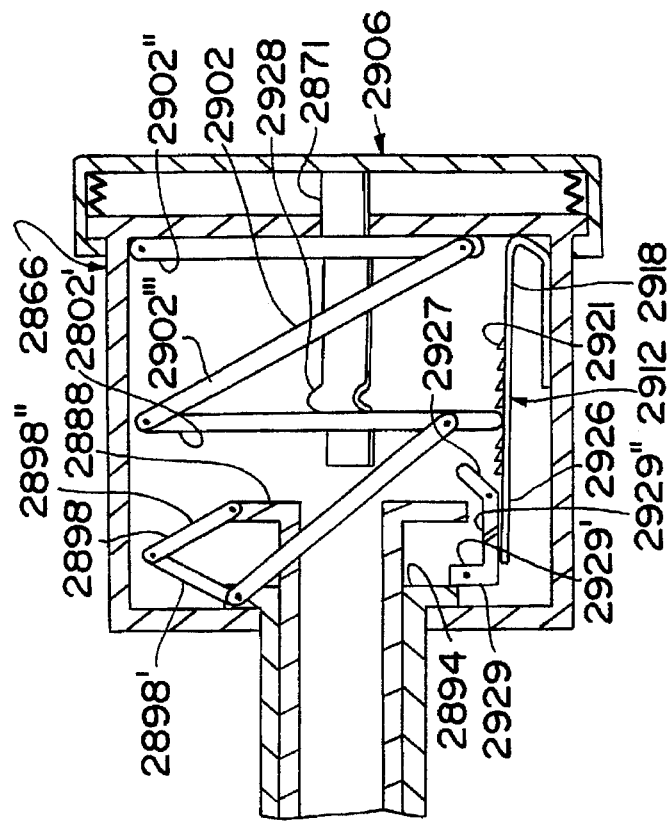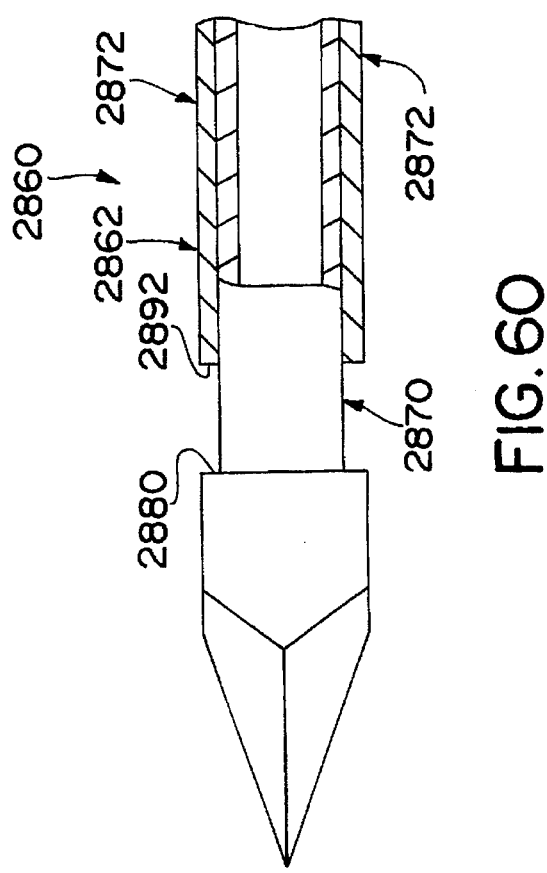
FIG. 60

AUTOMATIC RETRACTABLE SAFETY PENETRATING INSTRUMENT

CROSS-REFERENCES TO RELATED APPLICATIONS

This application is a division of pending prior application Ser. No. 08/196,027, filed Feb. 14, 1994 pending, which is a division application of prior application Ser. No. 07/945,177, filed Sep. 15, 1992 pending, which is a continuation-in-part of pending patent application Ser. No. 07/745,071 now abandoned, filed Aug. 14, 1991, 07/800,507 now abandoned, filed Nov. 27, 1991, Ser. No. 07/805,506 now U.S. Pat. No. 5,330,432 filed Dec. 6, 1991, Ser. No. 07/808,325, now U.S. Pat. No. 5,324,268, filed Dec. 16, 1991, Ser. No. 07/848,838, filed Mar. 10, 1992, now U.S. Pat. No. 5,445,614, Ser. No. 07/868,566 now U.S. Pat. No. 5,320,610 and Ser. No. 07/868,578 now U.S. Pat. No. 5,336,176, both filed Apr. 15, 1992, and Ser. No. 07/929,338 now U.S. Pat. No. 5,360,405, filed Aug. 14, 1992. The specifications of the above patent applications are incorporated herein by reference.

BACKGROUND OF THE INVENTION

1. Field of the Invention

The present invention pertains to safety penetrating instruments and, more particularly, to automatic retractable safety penetrating instruments having sleeves for introduction into anatomical cavities and penetrating members with sharp tips disposed within the sleeves for penetrating cavity walls with automatic retraction of the penetrating members into the sleeves upon penetration to protect tissue and organ structures within the cavities from the sharp tips of the penetrating members.

2. Discussion of the Prior Art

Penetrating instruments are widely used in medical procedures to gain access to anatomical cavities ranging in size from the abdomen to small blood vessels, such as veins and arteries, epidural, plural and subachroniad spaces, heart ventricles and spinal and synovial cavities, with access being established via a sleeve positioned during penetration into the cavity with the penetrating instrument. Use of penetrating instruments has become an extremely popular and important first step in endoscopic, or least invasive, surgical procedures to establish an endoscopic portal for many various procedures with access being established via portal sleeves of the penetrating instruments. Such penetrating instruments typically include a portal sleeve and a penetrating member disposed within the portal sleeve and having a sharp tip or point to pierce or penetrate the tissue forming the cavity wall with the force required to penetrate the cavity wall being dependent upon the type and thickness of the tissue of the wall. Once the wall is penetrated, it is desirable to prevent the sharp tip of the penetrating member from inadvertent contact with or injury to tissue or organ structures in or forming the cavity, and a particular problem exists where substantial force is required to penetrate the cavity wall or the cavity is very small in that, once penetration is achieved, the lack of tissue resistance can result in the sharp tip traveling too far into the cavity and injuring adjacent tissue or organ structures.

Safety trocars having a spring-biased protective shield disposed between an outer sleeve and an inner trocar are marketed by Ethicon, Inc. as the Endopath and by United States Surgical Corp. as the Surgiport. U.S. Pat. Nos. 4,535,773 to Yoon, 4,601,710 to Moll and 4,654,030 to Moll et al are illustrative of such safety trocars. A trocar disposed within a portal sleeve and retractable within the sleeve when force from tissue contact is removed from the sharp tip of the trocar is set forth in U.S. Pat. No. 4,535,773 to Yoon.

SUMMARY OF THE INVENTION

It is a primary object of the present invention to provide improved, simplified automatic retractable safety penetrating instruments capable of use in a wide variety of procedures.

A further object of the present invention is to provide an automatic retractable safety penetrating instrument having a locking and releasing mechanism rotatable or pivotal around an axis in parallel and spaced from a longitudinal axis of the automatic retractable safety penetrating instrument for automatically releasing a retracting mechanism to permit retraction of a penetrating member upon entry of the instrument into an anatomical cavity.

An additional object of the present invention is to position a rotatable locking and releasing mechanism within a shaft of a penetrating member of an automatic retractable safety penetrating instrument to reduce the size of the proximal hub or handle for the penetrating member.

A further object of the present invention is to form a penetrating member of an automatic retractable safety penetrating instrument of telescoping parts such that the distal end can be moved proximally relative to the shaft upon retraction thereby reducing the length of the hub or handle for the penetrating member.

Yet another object of the present invention is to automatically trigger retraction of a penetrating member within a sleeve upon movement of an operating member distally of a rest position after initial movement of the operating member proximally of the rest position during penetration of tissue.

A further object of the present invention is to combine trigger mechanisms in an automatic retractable safety penetrating instrument such that retraction can be triggered by distal movement of an operating member at a position rearward of a rest position of the operating member and/or a position forward of the rest position.

Another object of the present invention is to configure a safety penetrating instrument to allow the safety penetrating instrument to have various optional modes of operation including retraction of the penetrating member, retraction of the penetrating member along with a safety shield or probe, the penetrating member locked against retraction to operate as a standard penetrating instrument, the penetrating member retracts while the safety shield or probe remains extended, or the penetrating member locked against retraction while safety shield or probe moves distally.

Some of the advantages of the present invention over the prior art are that small or narrow anatomical cavities can be safety penetrated, sleeves can safely be introduced into anatomical cavities of various sizes to expand the use of least invasive procedures in many areas including, for example, cardiac, brain, vascular, chest, genitourinary system, breast and spinal fields, safe penetration of cavities can be accomplished with no parts of the safety penetrating instrument other than the sleeve protruding beyond the sharp tip of the penetrating member as is particularly desirable where organ structures adhere to cavity walls, the automatic retractable safety penetrating instrument encourages the use of a smooth, continuous penetration motion by the surgeon thereby reducing trauma, tears and irregular surfaces in the tissue of the cavity wall, the automatic retractable safety penetrating instrument can be used to penetrate anatomical cavities of the type containing organ structures that could be injured by contact with even a blunt instrument part such as a safety shield, the automatic retractable safety penetrating instrument can be economically made of plastic with relatively few components, safe penetration is achieved while permitting injection or evacuation of fluids, a single puncture can be used for both insufflation and forming an endoscopic portal thereby simplifying diagnostic and surgical procedures, trauma and damage to tissue is minimized, tissue jamming and trapping are avoided and automatic retractable safety penetrating instruments according to the present invention can be inexpensively manufactured to be reusable or disposable for universal use.

These and other objects and advantages of the present invention will become apparent from the following description of the preferred embodiments taken in conjunction with the accompanying drawings wherein identical reference numbers indicate identical parts or parts providing identical functions.

BRIEF DESCRIPTION OF THE DRAWINGS

FIGS. 2, 3 and 4 are broken side views, partly in section of the automatic retractable safety penetrating instrument of FIG. 1 in various states of operation.

FIG. 5 is a broken perspective view of an end cap release mechanism for use with the automatic retractable safety penetrating instrument of the present invention.

FIG. 5A is a perspective view of an end cap release mechanism carrying a locking and releasing mechanism for use with the automatic retractable safety penetrating instrument of the present invention.

FIG. 5B is a perspective view of an end cap release mechanism carrying a modified locking and releasing mechanism for use with the automatic retractable safety penetrating instrument of the present invention.

FIG. 5C is a section taken along lines 5C—5C of FIG. 5B with the addition of a retraction plate and an operating member.

FIG. 5D is a broken side view, partly in section, of a modified locking and releasing mechanism for use with the automatic retractable safety penetrating instrument of the present invention wherein the trigger is formed by an angled flat spring member.

FIG. 6 is a broken side view, partly in section, of an automatic retractable safety penetrating instrument according to the present invention having a modified locking and releasing mechanism.

FIGS. 6A, 6B and 6C are broken side views, partly in section, showing a modified locking and releasing mechanism for use with the instrument of FIG. 6.

FIG. 7 is a broken side view, partly in section, of an automatic retractable safety penetrating instrument according to the present invention having a safety shield.

FIG. 8 is a broken view, partly in section, showing interconnection of the shield and penetrating member of FIG. 7 to allow retraction of the shield and penetrating member together or the penetrating member alone.

FIG. 9 is a side view, partly in section, of another embodiment of an automatic retractable safety penetrating instrument according to the present invention in a rest state utilizing a probe for triggering retraction.

FIGS. 10, 11, 12 and 13 show operating states for the instrument of FIG. 9.

FIGS. 14, 15, 16 and 17 are end views of the trocar penetrating member of the instrument of FIG. 9 showing various positions of the probe.

FIG. 18 is a side view, partly in section, of a modification of the automatic retractable safety penetrating instrument of FIG. 9 wherein the penetrating member triggers retraction.

FIG. 19 is a broken perspective of the locking and releasing mechanism of the instrument of FIG. 18.

FIG. 20 is a broken side view, partly in section, of another embodiment of an automatic retractable safety penetrating instrument according to the present invention having a safety shield for triggering retraction.

FIGS. 21 and 22 are broken perspective views of distal ends for the instrument of FIG. 20.

FIG. 23 is a broken perspective view of the locking and releasing mechanism of the instrument of FIG. 20.

FIG. 24 is a broken side view, partly in section, of the instrument of FIG. 20 in the operative position.

FIGS. 25 and 26 are a broken side view, partly in section, and a broken top view, respectively, of the hub of the instrument of FIG. 20.

FIG. 27 is a broken side view, partly in section, of a modified distal end for an automatic retractable safety penetrating instrument according to the present invention.

FIG. 28 is a broken side view, partly in section, of the distal end of an automatic retractable safety penetrating instrument according to the present invention having a cannulated penetrating member.

FIG. 37 is a broken side view, partly in section, of an automatic retractable safety penetrating instrument according to the present invention wherein retraction is triggered by a shield.

FIG. 38 is a broken side view, partly in section, of an automatic retractable safety penetrating instrument according to the present invention having a modified locking and releasing mechanism.

FIGS. 39 and 39a are side and perspective views of locking and releasing members for use with the instrument of FIG. 38.

FIG. 40 is an end view of the locking and releasing member for use with the instrument of FIG. 38.

FIGS. 41, 42 and 43 are broken views showing operation of the locking and releasing mechanism of the instrument of FIG. 38.

FIG. 44 is a broken view, partly in section, of a modification of the locking and releasing mechanism of FIG. 38.

FIG. 45 is a broken side view, partly in section, of the locking and releasing mechanism of FIG. 38 triggered by a safety shield.

FIG. 46 is a broken side view of a modified locking and releasing member of the type illustrated in FIG. 38.

FIGS. 50 and 51 are broken side views, partly in section, of modifications of the instrument of FIG. 47.

FIG. 52 is a broken side view, partly in section, of an automatic retractable safety penetrating instrument according to the present invention in combination with a multi-lumenal member in the portal sleeve housing.

FIG. 53 is a broken side view, partly in section, of an automatic retractable safety penetrating instrument according to the present invention wherein the locking and releasing mechanism is disposed within a control tube.

FIG. 54 is a side view, partly in section, of an automatic retractable safety penetrating instrument according to the present invention wherein the distal end of a penetrating member telescopes with respect the shaft and is triggered for retraction by a safety shield for a probe, FIG. 55 is a broken side view, partly in section, of an automatic retractable safety penetrating instrument according to the present invention wherein the locking and releasing mechanism is located partly in the hub and partly in the shaft of the penetrating member.

FIGS. 56, 57, 58, 59 and 60 are broken side views, partly in section, of modifications of the automatic retractable safety penetrating instrument according to the present invention with various locking and releasing mechanisms.

DESCRIPTION OF THE PREFERRED EMBODIMENTS

Figure 1:
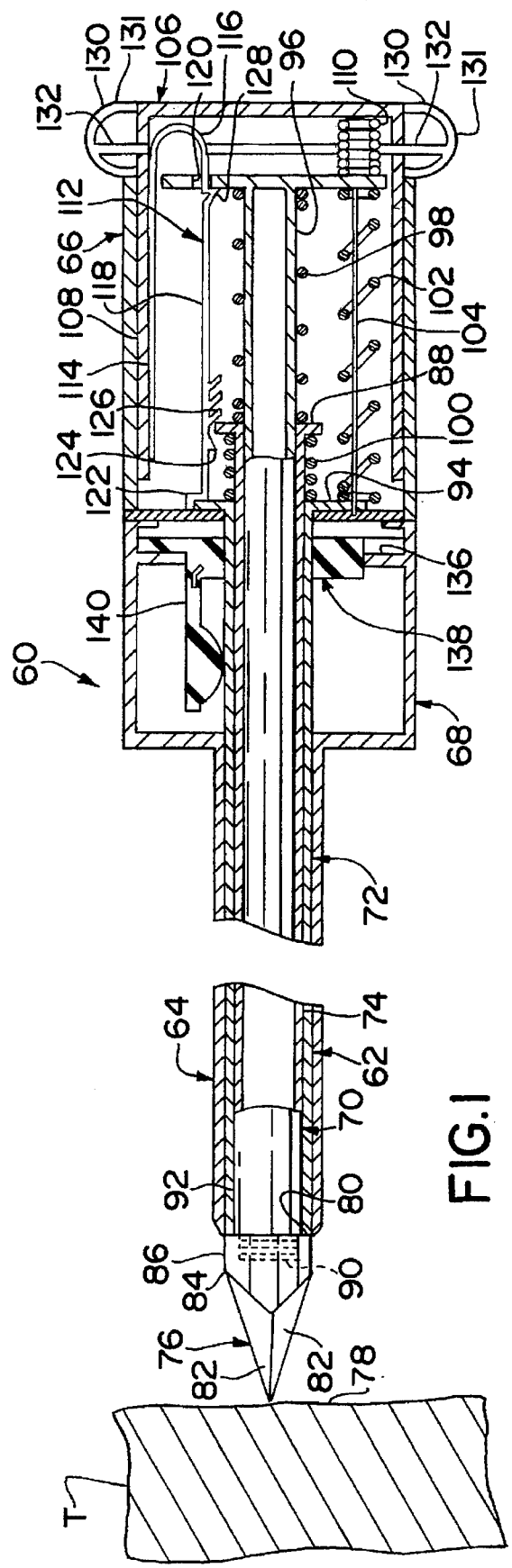
FIG. 1 is a broken side view, partly in section, of an automatic retractable safety penetrating instrument according to the present invention in a rest state.

An automatic retractable safety penetrating instrument 60 according to the present invention is illustrated in FIG. 1 and includes an elongate penetrating member 62, an outer sleeve or cannula, such as portal sleeve 64, concentrically disposed around the penetrating member, a hub 66 mounting penetrating member 62 and a valve housing 68 mounting portal sleeve 64. The hub 66 can be latched to housing 68 with the use of any suitable releasable mechanism, such as detents operated by buttons, allowing the hub to be removed from the housing withdrawing the penetrating member from the portal sleeve. Accordingly, the automatic retractable safety penetrating instrument 60 can be considered to be formed of a portal unit and a penetrating unit, the portal unit including portal sleeve 64 and housing 68 and the penetrating unit including penetrating member 62 and hub 66.

The penetrating member 62 is preferably made of a medical grade material, such as stainless steel, and has an outer diameter or size dependent upon the surgical procedure to be performed and the anatomical cavity to be penetrated. The penetrating member 62 is made up of a distal part 70 and a tubular end part 72 concentrically disposed around the distal part with the distal part mounted for longitudinal telescoping movement relative to the end part. Distal part 70 includes an elongate body 74 which can be cylindrical or have any desired configuration in cross-section terminating distally at a distal end 76 of the penetrating member. Distal end 76 terminates distally at a tip 78 for penetrating anatomical tissue and proximally at an end wall or shoulder 80 joining the distal end to body 74. The distal end 76 can have various solid or hollow geometric configurations including various trocar, blade and needle distal end configurations such as conical and pyramidal, and the tip 78 can be sharp or blunt and provided with an external thread. As shown in FIG. 1, distal end 76 is formed as a trocar having a pyramidal configuration with equally spaced end surfaces or facets 82 tapering distally to a sharp tip 78 and proximally joined at a junction 84 to a cylindrical neck 86 terminating proximally at shoulder 80. Body 74 terminates proximally at an operating member or flange 88 at a proximal end of the penetrating member, the proximal end being disposed in hub 66 with body 74 passing through an opening in a front wall of the hub. The distal end 76 can be formed integrally, unitarily with body 74 or the distal end can be formed separately from body 74 and removably mounted thereon, such as with threads 90, allowing various distal ends of diverse configurations to be interchangeably mounted on body 74. Body 74 has an outer diameter or size that is less than the outer diameter of neck 86 with end part 72 having an inner diameter sized to closely receive the outer diameter or size of body 74. End part 72 has an outer diameter that is the same as the outer diameter of neck 86 such that the neck and end part are closely received by the inner diameter of the portal sleeve 64. End part 72 terminates distally at a stop or abutment 92 proximally spaced from shoulder 80 with the instrument in an extended position as shown in FIG. 1 and proximally at a retraction member including a retraction plate or flange 94 disposed in hub 66 with the end part passing through the opening in the front wall of the hub and body 74 passing through an opening in the retraction plate. Body 74 can be hollow or tubular along the length thereof, or the body can be partly hollow or tubular to receive a control tube 96 extending distally from a rear wall of hub 66 and into the proximal end of the penetrating member. Where body 74 is hollow or tubular or formed with an internal passage along the length thereof communicating with the lumen of the control tube, a channel (not shown) can be disposed in distal end 76 in communication with the lumen or passage of the body to provide fluid communication entirely through the instrument 60. A valve (not shown), which can be of any conventional design, can be mounted in communication with the lumen of the control tube, such as along the rear wall of hub 66, to control fluid flow through the instrument. A cautery attachment can be provided on the penetrating member for electric cautery procedures. A helical coil operating spring 98 is disposed concentrically around the control tube and connected between operating flange 88 and the rear wall of the hub to bias the penetrating member in a distal direction. A helical coil balancing, cushion or positioning spring 100 is disposed concentrically around body 74 and connected between retraction plate 94 and the operating flange 88 to bias the penetrating member in a proximal direction such that the operating flange is maintained at an initial, rest or balanced position with the instrument in the extended position as shown in FIG. 1. A retracting mechanism engages the proximal end of the penetrating member and includes the retraction member, retraction plate 94 in FIG. 1, and a helical coil retracting spring 102 connected between retraction plate 94 and the rear wall of the hub. If required, a guide rod 104 can extend from the rear wall of the hub to the front wall thereof passing through the retraction plate with the retracting spring concentrically disposed around the guide rod to provide a guide to maintain the retracting spring in axial alignment.

Hub 66 can be made of any suitable material to be disposable or reusable and has an external configuration to cooperate with housing 68 to facilitate grasping by a surgeon with one hand for use in penetrating tissue. Hub 66 can have any desired configuration in cross-section and is shown in FIG. 1 as being substantially rectangular. An end cap 106 of hub 66 has a skirt 108 extending distally through an opening in the hub rear wall, the end cap being mounted for longitudinal movement relative to the hub by a mounting member including a helical coil mounting spring 110 connected between the hub rear wall and a rear wall of the end cap rear wall to bias the end cap in a proximal direction. If needed, various mechanisms can be provided in the hub or end cap to limit proximal movement of the end cap relative to the hub.

A locking and releasing or trigger mechanism 112 actuates the retracting mechanism and includes a latch or locking spring having a substantially flat base 114 secured to an inner surface of skirt 108 to extend through the opening in the hub rear wall and a U-shaped bend 116 disposed in the end cap and proximally joining base 114 to an arm 118. Arm 118 extends distally from bend 116 through a slot 120 in the rear wall of the hub, the arm extending in the direction of the retraction plate 94 substantially parallel with a longitudinal axis of the instrument. A bent locking finger or member 122 is carried on a distal end of the arm to engage the retraction plate 94 when the locking spring is in its normal condition as illustrated in FIG. 1. A trigger or releasing member 124 including a cam or bend in arm 118 is disposed distally of the operating flange 88 in the initial position the trigger member 124 being angled in a distal direction from the arm to cause bending or flexing of the arm in am direction outwardly from the instrument longitudinal axis when the operating flange is moved distally of the initial position as will be explained further below. One or more than one additional trigger or releasing members 126 are disposed on arm 128 proximally of the operating flange 88 in the initial position; and where a plurality of trigger members 126 are provided, it is preferred that the trigger members be closely spaced to extend longitudinally along the arm as shown in FIG. 1. The trigger members 126 are angled in a proximal direction from arm 118 to allow movement of the operating flange thereby in a proximal direction to a set position without causing bending or flexing of arm 118 and to cause bending or flexing of arm 118 in a direction outwardly from the instrument longitudinal axis when the operating flange is moved distally from the set position toward the initial position. A detent including a bump, protrusion or cam 128 is provided on arm 118 distally of bend 116 and proximally of the trigger members 126. Protrusion 128 has a forward portion angled from arm 118 in a proximal direction to permit distal movement of the protrusion through slot 120 and a transverse rear portion joined to the forward portion to prevent proximal movement of the protrusion through the slot to lock the end cap relative to the hub when the instrument is in the extended position. An end cap release mechanism for releasing the detent from the hub is provided in instrument 60 and includes an actuating device made up of a pair of actuating buttons 130 externally mounted on end cap 106 at diametrically opposing locations with release arms 132 extending from buttons 130 through skirt 108 in a direction transverse to the instrument axis to be disposed on opposite sides of bend 116. Buttons 130 can have various configurations to move the release arms to squeeze, flatten or compress bend 116 inwardly to align protrusion 128 with slot 120, the release arms being moved in a direction aligned with the direction of squeezing of bend 116 when the buttons are pressed inwardly in the direction of the instrument axis as will be explained further below. As shown in FIG. 1, buttons 130 are in the nature of springs 131 made of resilient strips of metal, plastic or other spring material forming lobes having a bulging configuration in a direction outwardly from the instrument axis with the release arms extending therefrom to be moved by the lobes when the lobes are flattened or collapsed. One or more than one button 130 can be provided on end cap 106; and, where two buttons are provided at diametrically opposing locations, bilateral actuation of the end cap release mechanism is facilitated. The release arms 132 can be arranged in many ways to be aligned with or offset from one another; and, where only a single button and release arm are provided, the bend can be compressed between the release arm and the skirt.

Sleeve 64 can be a portal sleeve or cannula as shown in FIG. 1 or any other tubular structure, such as a catheter for intravenous use, designed to establish communication with an anatomical cavity. Sleeve 64 is preferably made of a substantially cylindrical length of rigid or flexible and transparent or opaque material, such as stainless steel or other suitable, medically acceptable, plastic or metal material; and, where the sleeve is made of a flexible material, the penetrating member can also be made of a flexible material. The sleeve has an outer diameter dependent upon the size of the penetrating member and the surgical procedure to be performed, the sleeve typically ranging in size from portal sleeve size to intravenous tube size, with an inner diameter sized to closely receive the outer diameters of neck 86 and end part 72. Portal sleeve 64 has a distal end 134 with a configuration to produce a smooth profile with the distal end 70 of the penetrating member when the instrument is in an operative position to penetrate tissue as will be explained further below, a proximal end mounted in or formed with a front wall of valve housing 68 and a lumen extending between the distal and proximal ends.

Housing 68 can be made of any suitable material to be disposable or reusable and has a configuration in cross-section corresponding to the cross-sectional configuration of hub 66. A wall 136 extends inwardly from housing 68 at a position distally spaced from the rear end thereof to produce a recess suitable for receiving detents (not shown) releasably securing the hub and housing, the wall 136 having a central passage for receiving a valve assembly. The valve assembly can have any conventional configuration to produce a closed or sealed condition upon removal of the penetrating unit. As shown in FIG. 1, the valve assembly is formed as a unitary, one-piece integral construction of rubber or soft plastic to facilitate sealing to prevent fluid flow through the instrument when the penetrating unit is removed. The valve assembly is formed of a valve body 138 having a passage therethrough and a proximal flange extending outwardly therefrom to be received in the recess at the rear end of the housing. The valve body 138 has a peripheral configuration to fit snugly within the passage through wall 136, and a valve member extends distally from valve body 138 and has a normally sealed position with a hemispherical bulging end received in a valve seat formed at an end of the passage to produce a normally closed, sealed configuration. To provide assisted bias toward the sealed configuration, a spring member 140 can be imbedded within the valve assembly to bias the valve member toward the valve seat. While the face of the valve seat is illustrated as being transverse to the longitudinal axis of the automatic retractable safety penetrating instrument 60, the valve seat can be angularly oriented.

Figure 2:
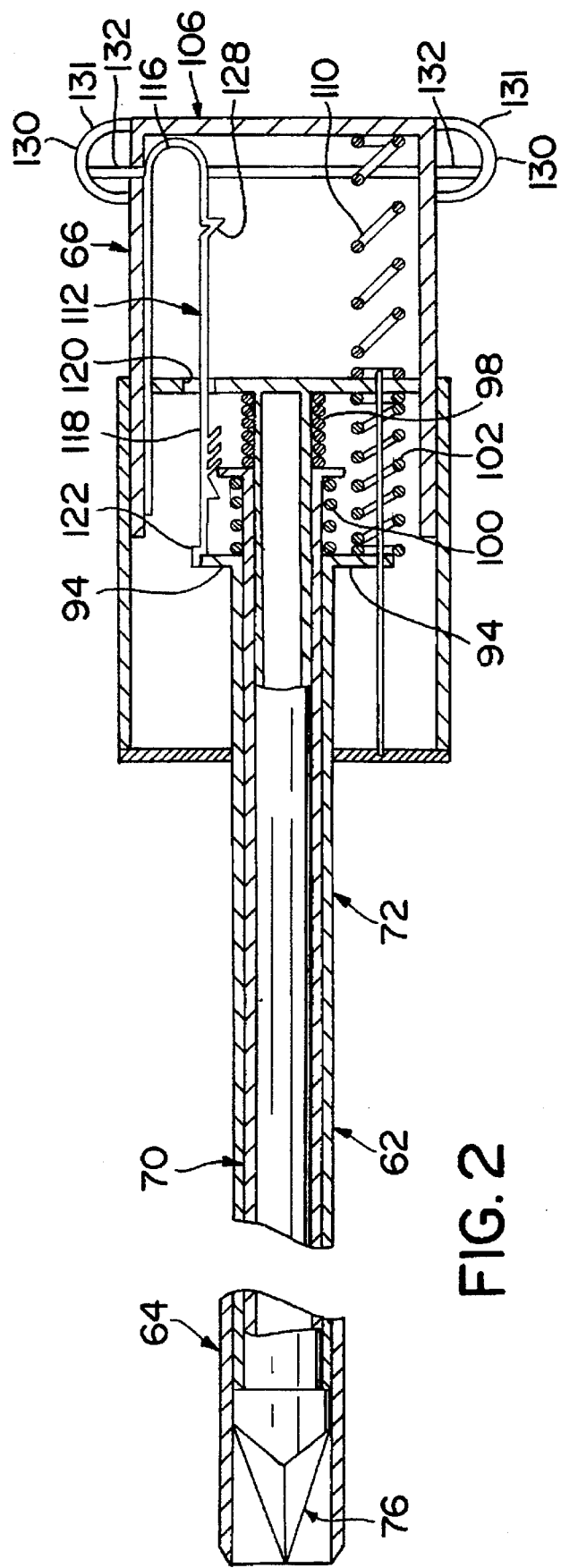

In use, the automatic retractable safety penetrating instrument 60 is normally provided in a rest state wherein the distal end 76 of penetrating member 62 is retracted within portal sleeve 64 to be in a safe, protected position, the rest state coinciding with the retracted position for the penetrating member. In the rest state, retracting spring 102 is in a relaxed, unbiased or unloaded state causing retraction plate 94 to be moved proximally carrying with it penetrating member 62. Springs 131 are in relaxed states forming lobes extending in a direction outwardly from the instrument axis. Operating spring 98 and cushion spring 100 are also in relaxed, unloaded or unbiased states; and, accordingly, with the automatic retractable safety penetrating instrument 60 initially provided in a rest state, no loading of the springs 98, 100, 102 and 131 exists such that the strength of the springs is not weakened and shelf life is increased. Where it is desired to supply the instrument 60 in as small a configuration as possible, end cap 106 can be supplied in a locked position with protrusion 128 locked within the hub and locking and releasing mechanism 112 disengaged from the retracting mechanism in the rest position for the instrument. Where the instrument 60 can be supplied in a ready position with end cap 106 biased proximally relative to the hub as illustrated in FIG. 2, mounting spring 110 can be in an unloaded or relaxed state with protrusion 128 disposed proximally of the hub rear wall, and the locking and releasing mechanism 112 can be in a relaxed state with the locking spring in the normal condition with locking member 122 engaged with retraction plate 94. Where the instrument is supplied with the end cap locked within the hub, buttons 130 are depressed causing release arms 132 to move toward each other squeezing bend 116 to align the rear portion of protrusion 128 with slot 120 such that mounting spring 110 automatically moves the end cap proximally, and the instrument will be in the ready position shown in FIG. 2. When it is desired to utilize the instrument 60 to penetrate tissue and enter an anatomical cavity, the hub and housing are grasped by a surgeon, and the end cap 106 is squeezed causing movement of the end cap distally relative to the hub such that arm 118 functions as a push member to move the retraction plate 94 and with it end part 72 distally carrying distal part 70 in the distal direction. Continued squeezing of the end cap causes the forward portion of protrusion 128 to be engaged by the hub rear wall such that arm 118 is bent or flexed a small amount allowing the protrusion 128 to pass through the slot 120 and into the hub while the retraction plate 94 remains held by the locking member 122. Once protrusion 128 has entered the hub, arm 118 returns to the normal condition, and the rear portion of the protrusion engages the rear wall of the hub to lock the end cap against proximal movement at which time the end part 72 will be locked against proximal movement with the retraction plate 94 locked in place adjacent the front wall of the hub as shown in FIG. 1. With the instrument 60 in the extended position shown in FIG. 1, the operating flange 88 will be in the initial position disposed proximally of trigger member 124 and distally of trigger members 126 and the distal end junction 84 of the penetrating member will be spaced from the distal end 134 of the portal sleeve by a distance that is the same as the spacing between shoulder 80 and abutment 92.

The instrument can now be utilized to penetrate tissue and enter an anatomical cavity. The hub and housing are grasped by the surgeon, and the instrument is forced against tissue, such as tissue T forming a wall of an anatomical cavity, causing distal part 70 of penetrating member 62 to move proximally relative to end part 72 against the bias of operating spring 98. Abutment of shoulder 80 with stop 92 limits proximal movement of the distal part at which time the instrument will be in an operative position illustrated in FIG. 3 with the distal end junction 84 aligned with the distal end 134 of the portal sleeve to form a substantially smooth profile. As distal part 70 moves proximally, operating flange 88 moves proximally deflecting trigger members 126 in the proximal direction such that the operating flange moves proximally therepast to a set position without disengaging the locking member 122 from the retraction plate 94. Once the distal end 134 of the portal sleeve has passed through the tissue T and entered the anatomical cavity, operating spring 98 will move distal part 70 distally relative to end part 72 causing the operating member 88 to be moved distally from the set position toward the initial position to engage a trigger member 126 distally closest thereto such that arm 118 is flexed or bent in a direction outwardly from the instrument axis causing locking member 122 to be moved out of engagement with retraction plate 94. Accordingly, retracting spring 102 will automatically move the retraction member 94 and with it the end and distal parts of the penetrating member to the retracted position with the distal tip 78 of the penetrating member in a safe, protected position within the portal sleeve as shown in FIG. 4. By providing a plurality of closely spaced trigger members 126, the distance that the operating member must be moved distally from the set position prior to retraction can be minimized. Where the operating member is moved to a set position that is not proximal of a trigger member 126 due to the resistance of the tissue being small or where trigger members 126 are not provided, operating spring 98 will move the distal part of the penetrating member distally from the set position upon the portal sleeve distal end entering the anatomical cavity, and the momentum of the operating spring will override the bias of the cushion spring 100 such that the operating member 88 will be moved distally of the initial position to engage trigger member 124 and flex arm 118 in a direction outwardly from the instrument axis such that the locking member 122 is moved out of abutment with retraction plate 94. By providing both trigger members 124 and 126, redundant protection is provided for the automatic retractable safety penetrating instrument 60 in that triggering can be obtained via either distal movement of the operating member from the set position toward the initial position or distal movement of the operating member past the initial position.

Once the distal end of the instrument 60 has entered the anatomical cavity and the penetrating member has moved to the retracted position, the portal sleeve will have been introduced into the cavity such that the penetrating unit can be withdrawn from the portal unit. When the penetrating unit is withdrawn, the valve member will return to the biased position such that the bulging end will engage the valve seat to seal the portal unit from fluid flow therethrough from insufflation pressure. Additionally, the axial length of the passage produces an elongated seal with penetrating member 62 minimizing escape of fluid during cavity penetration; and, if an instrument of a different size than the penetrating member is to be introduced after withdrawal of the penetrating unit, the valve assembly can be easily interchanged to install a valve assembly having a passage of a diameter to seal along the different size instrument.

The instrument 60 can be reusable or disposable for single patient use; and, where reusable, instrument 60 can be moved from the retracted position to the ready position by pushing or depressing buttons 130 causing release arms 132 to move toward each other. Accordingly, bend 116 will be compressed or flattened such that the rear portion of protrusion 128 is aligned with the slot 120 in the hub rear wall causing mounting spring 110 to automatically move the end cap 10 proximally relative to the hub. The locking spring will return to the normal condition with locking member 112 engaged with retraction plate 94, and the instrument will be in the ready position to be reset in the extended position via squeezing operation of the end cap.

Various mechanisms can be utilized in the automatic retractable safety penetrating instrument in place of or in addition to the end cap for use in setting the instrument in the extended position. As one example, a pin and slot arrangement can be used as the resetting mechanism with a pin provided on the penetrating member or the retracting mechanism, such as in the periphery of the retraction plate, to extend through a longitudinal slot in the hub allowing the retracting mechanism to be moved via manual movement of the pin along the slot when setting the instrument in the extended position.

While coiled springs are shown in the instrument 60 for the operating, retracting, cushion and mounting springs, many different arrangements and types of springs or other bias devices can be utilized with the present invention, and the bias devices can be arranged in instrument 60 in many various ways. Where springs are utilized, the springs can be tension, compression or torsion springs. When the operating member is proximally spaced from the trigger member 124 in the initial position, the cushion and operating springs can be of equal strength, and where the operating member is engaged with the trigger member 124 in the initial position, the cushion spring can be of lesser strength than the operating spring due to the increased resistance provided by the trigger member 124. The cushion spring can be disposed at various locations in the instrument including within the shaft of the penetrating member to position the operating member in the initial position. Various single or multiple piece devices can be utilized as the locking and releasing mechanism to lock the retracting mechanism against movement and to be released in response to distal movement of an operating member. The locking and releasing mechanism can be mounted for movement around an axis transverse to the instrument axis as shown in FIG. 1, parallel with the instrument axis, aligned with the instrument axis and in many other ways. Various types of trigger members including cams, springs with bumps or springs cut to provide extending leaves or triggers, linkages and many other types of devices can be utilized to trigger retraction in response to distal movement of the operating member, and the trigger members can be provided at any suitable location including on the locking member or the operating member. Where provided on the locking member, the trigger members can be formed integrally, unitarily with the locking spring or separately therefrom. As shown in FIG. 1, locking member 122 and trigger members 124 and 126 are unitarily, integrally formed of a single strip of resilient, spring material such as metal or plastic. In addition to the penetrating member, various other parts of the instrument including the sleeve can be utilized to trigger retraction; and, where the instrument is supplied with a safety shield or probe, movement of the probe or shield trigger release of the retracting mechanism. Where movement of the shield or probe is utilized to trigger retraction, retraction can be triggered via movement of an operating member from the set position toward the initial position or distally of the initial position. The locking and releasing mechanism can be arranged in the instrument 60 in many ways; and, depending on the size of the instrument, the locking and releasing mechanism can be mounted within or externally of the penetrating member, within the control tube, the hub or the housing. Where disposed within the penetrating member, the locking and releasing mechanism can be mounted at any location along the shaft of the penetrating member including the penetrating member distal end to be disposed entirely or partially within the penetrating member. The end cap can be mounted on the hub in many ways with the skirt disposed within or externally of the hub, and various bias members can be utilized to bias the end cap. Where secured to the end cap, the locking and releasing mechanism can be provided as a module facilitating assembly of the automatic retractable safety penetrating instrument. The locking and releasing mechanism can be utilized as the push member or the push member can be a separate device. Various release mechanisms can be utilized in the instrument 60 to be manually actuated to release the end cap from the hub, and the release mechanisms can be mounted on the instrument in many various ways in accordance with the structure of the locking and releasing mechanism or push member with the release mechanism of FIG. 1 being particularly advantageous for bilateral operation with right and left hand compatibility. The distance that the end cap must be moved proximally in the ready position will be in accordance with the distance that the push member must be moved proximally to be in a position to move the retracting mechanism distally. Accordingly, the length of skirt 108 will depend upon the distance that the end cap must be moved proximally, and various devices such as a bellows can be provided in the instrument to bridge any longitudinal gap or space between the skirt and the hub where the skirt is moved outside of the hub in the ready position. Instrument 60 can be provided with or without a control tube, although a control tube is desirable to allow fluid flow through the instrument. Control tube 96 can be rotatably mounted and can extend through the end cap to terminate at the end cap rear wall. A valve can be disposed along the rear wall of the end cap in communication with the lumen of the control tube to control fluid flow through the instrument where the inner member is hollow or formed with an internal passage.

A modified locking and releasing mechanism and end cap release arm for the automatic retractable safety penetrating instrument according to the present invention are illustrated in FIG. 5 at 160 wherein the locking and releasing mechanism 212 is shown without a trigger member. Locking and releasing mechanism 212 is similar to locking and releasing mechanism 112 and includes a latch or locking spring having a base 214 for being secured to the end cap of the automatic retractable safety penetrating instrument, a U-shaped bend 216 and an arm 218 joined to base 214 by bend 216. Arm 218 has a locking member 222 at a distal end thereof to engage the retracting member for locking the retraction mechanism of the automatic retractable safety penetrating instrument against movement; and, if desired, arm 218 can be used as the push member for use in setting the automatic retractable safety penetrating instrument in the extended position via squeezing operation of the end cap. A detent or protrusion 228 is disposed on arm 218 distally of bend 216 for locking the end cap relative to the hub of the automatic retractable safety penetrating instrument in the extended position. Various trigger members can be provided on the locking spring to be actuated by the operating member to trigger retraction, or the locking spring can be designed to cooperate with a trigger member provided on the operating member as will be explained further below. Release arm 218 extends into the end cap to terminate at a tapered end 219 for compressing or squeezing bend 216 when the release arm is moved toward the locking spring by an actuating device, such as buttons 130, in a direction transverse to the direction of squeezing. Accordingly, by moving the release arm 218 into the end cap in a direction transverse to the desired direction of flattening or squeezing of the bend, the tapered configuration of the release arm will progressively flatten or compress the bend allowing protrusion 228 to move through the slot in the hub rear wall thusly releasing the end cap.

A modification of the locking and releasing mechanism for the instrument 60 is illustrated in FIG. 5A wherein triggers 124 and 126 are mounted on a substrate 121 laminated to arm 118 with triggers 126 and 127 cut from substrate 121 as indicated by apertures 127 to be bent upwardly therefrom. Accordingly, triggers 126 will flex distally and downwardly looking at FIG. 5 during proximal movement of the operating member; and, during distal movement of the operating member, the triggers 126 will cause the arm 118 to flex to release the retracting mechanism, the substrate providing additional strength to allow repetitive operation of the triggers 126.

In the modified locking and releasing mechanism illustrated in FIGS. 5B and 5C, the arm 118 is cut at 119 to allow triggers 124 and 126 to extend therethrough angled proximally to allow operating member 88 to pass thereby while flexing the triggers 126 without flexing the arm 118, the operating member having a beveled ends 89 to facilitate proximal movement thereof. The triggers 124 and 126 extend from a member 123 disposed below arm 118 and having a lip 125 engaging the edge of arm 118 such that member 123 can flex downwardly looking at FIG. 5C without movement of arm 118 with proximal movement of operating member 88. Upward movement of member 123 is prevented during distal movement of operating member 88 such that the arm 118 is caused to deflect downwardly moving lock 122 from the locked position to a release position actuating the retraction mechanism.

In the modified locking and releasing mechanism illustrated in FIG. 5D, no trigger members 126 are utilized and the trigger 124 is formed of an angled portion of arm 118. The rest position is illustrated in FIG. 5D; and, after movement of operating member 88 rearwardly from the rest position, the operating member will be subsequently moved distally past the rest position due to the force from operating spring 98 compressing spring 100. As the operating member 88 moves forwardly of the rest position, the peripheral edge of the operating member, which is preferably angled at the same angle as the trigger 124, engages the trigger 124 to move the lock 122 to the release position allowing retraction.

A modification of the automatic retractable safety penetrating instrument according to the present invention is illustrated at 360 in FIG. 6, only the penetrating unit of the instrument 360 being shown. The automatic retractable safety penetrating instrument 360 is similar to automatic retractable safety penetrating instrument 60; however, the operating member or flange 388 for the automatic retractable safety penetrating instrument 360 has a trigger member 326 extending from the periphery thereof, the trigger member 326 being angled outwardly from the operating member in a distal direction. The locking and releasing mechanism 312 for the automatic retractable safety penetrating instrument 360 includes a latch or locking spring similar to that described for locking and releasing mechanism 112; however, arm 318 for locking and releasing mechanism 312 has a plurality of spaced barbs, ratchet teeth or serrations 321 extending longitudinally therealong for being successively engaged by trigger member 326.

Operation of automatic retractable safety penetrating instrument 360 is similar to that described for automatic retractable safety penetrating instrument 60 in that the operating flange is positioned by the operating and balancing springs 398 and 400 in an initial position with trigger 326 disposed distally of some of the barbs 321. Where the initial position for the trigger member is such that at least one barb is disposed distally of the trigger member, the trigger member can be maintained in engagement with the nearest distal barb as illustrated in FIG. 6 allowing the cushion spring to be of lesser strength than the operating spring and for further stability in the initial position. During penetration of anatomical tissue, operating member 388 will be moved proximally causing trigger member 326 to move proximally past and engage successive barbs 321 such that the penetrating member moves incrementally in a controlled manner until the operating member has moved to the set position with the trigger engaged with a distally closest barb. Once the distal end of the portal sleeve has entered the anatomical cavity, operating spring 398 will move operating flange 388 distally from the set position such that trigger member 326, via engagement with the distally nearest barb, causes arm 318 to be pivoted and locking member 382 to be released from engagement with retraction plate 394 for immediate retraction upon penetration with minimal distal movement of the operating flange. By providing a plurality of closely spaced barbs, trigger member 326 will be engaged with a nearest distal barb for various set positions ensuring immediate retraction upon distal movement of the operating member. Where momentum triggering is desired, one or more barbs 321 can be disposed distally of the initial position to be utilized to pivot the arm 318 upon distal movement of the operating member distally of the initial position. Where momentum triggering is utilized, one barb disposed distally of the initial position should be sufficient to trigger retraction; however, more than one barb can be provided for increased safety. The automatic retractable safety penetrating instrument 360 can be used with or without momentum triggering; and, where momentum triggering is provided in addition to triggering by distal movement of the operating member from the set position toward the initial position, redundant protection is provided.

A modification of the instrument 360 is shown in FIG. 6A wherein teeth or barbs 321 are formed of flexible members while operating member 388 has a beveled end 389 whereby the configuration of the teeth 321 and the operating member 388 allows flexing of the teeth as the operating member moves proximally thereby but, during distal movement of the operating member upon entry into an anatomical cavity, the arm 318 will be flexed to release lock 322 and actuate retraction.

In the modification of FIGS. 6B and 6C for use with instrument 360, the trigger 326 is replaced with a pivotal member 327 having an angled surface to facilitate movement past teeth 321. The pivotal member 327 shown in FIG. 6B is mounted on a pivot 329 on the peripheral edge of operating member 388 and the pivotal member has a triangular shape such that the member can pivot only counterclockwise looking at FIG. 6B. Accordingly, the pivotal member 328 can pivot to allow proximal movement of the operating member 388 but, upon distal movement of the operating member, will cause the arm 318 to flex to actuate the retraction mechanism. In FIG. 6C, pivotal member 327' is mounted on a pivot 331 to form a transversely extending operating member which can pivot only counterclockwise looking at FIG. 6C due to a protrusion 333 preventing clockwise pivoting. Accordingly, member 327' will pivot during proximal movement but will cause arm 318 to deflect to actuate the retracting mechanism upon distal movement.

Another modification of the automatic retractable safety penetrating instrument according to the present invention is illustrated at 460 in FIG. 7, only the penetrating unit of the instrument 460 being shown. The automatic retractable safety penetrating instrument 460 is similar to automatic retractable safety penetrating instrument 60 except that a safety shield 463 is concentrically disposed around the penetrating member 462 with the penetrating member including a body 474 terminating proximally at retraction plate or flange 494 disposed in hub 466. Safety shield 463 has a distal end 467 disposed beyond the tip 478 of the penetrating member when the instrument is in an extended position as shown in FIG. 7 and a proximal end terminating at an operating member or flange 488 disposed in hub 466. A helical coil operating spring 498 is concentrically disposed around the penetrating member and connected between operating flange 488 and retraction plate 494 to bias the safety shield in a distal direction. A helical coil cushion spring 500 is disposed concentrically around the safety shield and connected between the front wall of the hub and the operating flange 488 to bias the safety shield in a proximal direction such that the operating flange is maintained at an initial position with the instrument in the extended position as shown in FIG. 7. A helical coil retracting spring 502 disposed around guide rod 504 is connected between retraction plate 494 and the front wall of the hub. Hub 466 and end cap 506 are similar to hub 66 and end cap 106 with end cap 506 being mounted for longitudinal movement relative to the hub and biased in a proximal direction by a bias member including a mounting spring 510. A locking and releasing or trigger mechanism 512 for actuating the retracting mechanism includes a latch or locking spring similar to that described for locking and releasing mechanism 112 except that arm 518 for locking and releasing mechanism 512 includes a proximal portion angled from the protrusion 528 to extend distally in the direction of a longitudinal axis of the instrument and a distal portion bent from the proximal portion to extend distally in a direction outwardly from the longitudinal axis, the distal portion terminating distally at the locking finger or member 522 engaged with the retraction plate 494 when the locking spring is in its normal condition as illustrated in FIG. 7. An extension 523 of arm 518 extends distally from the locking member substantially parallel with the instrument longitudinal axis. A plurality of trigger members 524 are disposed longitudinally along the extension at spaced locations therealong with a most proximal one of the trigger members 524 positioned distally of the operating member in the initial position as illustrated in FIG. 7. A plurality of trigger members 526 extend longitudinally along extension 523 at spaced locations therealong with a most distal one of the trigger members 526 disposed proximally of the operating member in the initial position. When the trigger members are formed of or cut from the material of the locking spring as shown in FIG. 7, an extra layer or strip of material 525 can be provided on arm 518 including extension 523 for additional strength. As best illustrated in FIG. 8, a nub 489 extends radially inwardly from an inner surface of the wall of the safety shield 463, the nub extending from the operating flange 488. A longitudinal slot 491 is formed in the penetrating member 462 to receive the nub such that, with the operating flange in the initial position, the nub is disposed at a distal end of the slot in engagement with the wall of the penetrating member.

Operation of the automatic retractable safety penetrating instrument 460 is similar to that previously described for automatic retractable safety penetrating instrument 60 in that the instrument 460 is normally provided in a rest state and is moved to the ready position by releasing end cap 506 from hub 466 via actuation of buttons 530. The instrument is moved to the extended position illustrated in FIG. 7 via squeezing operation of the end cap 506 causing the retracting mechanism to be moved distally by the arm 518 to lock the retraction plate 494 in place against the locking member 522 with the end cap held in place by protrusion 528 within the hub. With the instrument 460 in the extended position, the operating member 488 will be in the initial position disposed proximally of a most proximal one of the trigger members 524 and distally of a most distal one of the trigger members 526, the distal end junction 484 of the penetrating member will be substantially aligned with the distal end of the portal sleeve and the distal end 467 of the safety shield will extend beyond the tip 478 of the penetrating member such that the penetrating member is in a safe, protected position. When the instrument 460 is forced against tissue to enter an anatomical cavity, the safety shield 463 will be moved proximally against causing the operating member 488 to move to a set position with trigger members 526 deflecting proximally allowing movement of the operating member therepast. Movement of the safety shield causes nub 489 to be moved proximally within the longitudinal slot 491 as shown in dotted lines in FIG. 8, and a proximal end of the slot can serve as a stop or abutment limiting proximal movement of the safety shield. Once the distal end of the portal sleeve 464 has entered the anatomical cavity, the operating spring 498 will move the safety shield distally causing the operating member 488 to move distally toward the initial position and engage the distally closest trigger member 526 to flex the locking spring and release the retraction plate 498 from the locking member 522. Once the retraction plate is released, retracting spring 502 will automatically move the penetrating member 462 proximally to a retracted position, the penetrating member carrying with it the safety shield 463 due to engagement of the penetrating member wall with the nub 489. Accordingly, both the penetrating member and safety shield distal ends can be retracted within the portal sleeve minimizing extension of the automatic retractable safety penetrating instrument into the anatomical cavity. Where trigger members 526 are not provided or the set position is such that there is no trigger member 526 between the initial and set positions, trigger members 524 can be utilized to trigger retraction in that the momentum of the operating spring upon penetration into the anatomical cavity overrides the bias of the cushion spring to move the operating member distally of the initial position causing the operating member to engage a trigger member 524 and flex the locking spring to release the retraction plate. Where the nub 489 and slot 491 are not provided, the penetrating member alone will be retracted upon penetration through the tissue with the safety shield remaining extended. Instrument 460 can be designed to allow removal of the penetration member and the safety shield together or individually from the portal sleeve.

Another modification of an automatic retractable safety penetrating instrument according to the present invention is illustrated in FIG. 9 at 560. The automatic retractable safety penetrating instrument 560 includes a penetrating member 562, a portal sleeve 564 concentrically disposed around the penetrating member, a probe 565 disposed within the penetrating member, a hub 566 mounting penetrating member 562 and probe 565 and a valve housing 568 mounting portal sleeve 564. The hub 566 can be latched to housing 568 with detents formed on the hub at a forward end thereof, the detents being in the nature of beads or protrusions for being snapped or locked in place in recesses formed along an inner surface of the wall of the housing at a rear end thereof. The detents can be frictionally retained in the recesses allowing the hub to be removed from the housing with manual force such that the penetrating unit can be removed from the portal unit. The penetrating member 562 is similar to penetrating members 462 and has a distal end 576 with a pyramidal configuration defined by equally spaced end surfaces or facets 582 tapering distally to a tip 578 and terminating proximally at a scalloped junction 584 joining the facets to an elongate body 574, the body 574 terminating proximally at a retraction plate 594 disposed in hub 566. Probe 565 includes an elongate member which can be cylindrical or have any other desired configuration in cross section terminating distally at a blunt tip 569 extending through an aperture in one of the facets and proximally at an operating member 588. The probe can be solid, hollow or tubular or partly hollow or tubular; and, as shown in FIG. 9, the probe 565 is in the nature of a solid, cylindrical rod, bar or wire having a minimal outer diameter or size with a relatively thicker piece of material joined proximally to the bar at a right angle thereto to define the operating member 588. Body 574 can be hollow or tubular or formed with an internal passage along the length of the penetrating member with the probe disposed in the lumen or passage of the body to be laterally offset from a longitudinal axis of the instrument 560 as shown in FIG. 9 or aligned with the instrument axis including being concentrically disposed within the penetrating member. A push member 571, which can be solid or tubular, extends distally through a rear wall of hub 566 and into a proximal end of the penetrating member for setting the instrument in the extended position shown in FIG. 9, the push member being aligned with the instrument longitudinal axis with the probe laterally offset therefrom. A helical coil operating spring 598 is connected between operating flange 588 and the rear wall of the hub laterally offset from the push member to bias the probe in a distal direction. A helical coil cushion spring 600 is connected between the operating flange 588 and the retraction plate 594 to bias the probe in a proximal direction against the distal bias of the operating spring such that the operating member is maintained at an initial position with the instrument in the extended position as illustrated in FIG. 9. A helical coil retracting spring 602 is connected between retraction plate 594 and a rear wall of the hub to bias the retraction member proximally. The hub rear wall has an opening therein allowing passage therethrough by the push member 571, and a tubular collar 573 extends proximally, externally from the hub rear wall with the push member 571 extending proximally through the collar to terminate at an external knob 575 for rotating the push member around an axis aligned with the instrument longitudinal axis. A helical or spiral-like groove 577 is formed in an outer surface of the push member to receive a cam or pin 579 mounted externally along the hub rear wall and extending into the lumen of the collar such that rotation of the push member around the instrument axis produces longitudinal movement of the push member relative to the hub. With the push member fully inserted in the hub such that knob 575 abuts the collar 573 as shown in FIG. 9, the pin 579 is received in a proximal end of the groove 577, and a nub 581 protruding from the control tube distally of the groove is longitudinally aligned with a longitudinal slot 583 in the penetrating member, the slot extending through the retraction plate 594. The locking and releasing mechanism 612 for actuating the retracting mechanism includes a latch or locking spring similar to the locking spring for locking and releasing mechanism 112 except that no trigger members 126 are provided and trigger member 624 is made from a portion of arm 618 angled in a distal direction toward the instrument longitudinal axis to be disposed distally of the operating member in the initial position.

In use, the automatic retractable safety penetrating instrument 560 is normally provided in a rest state with the distal end 576 of the penetrating member 562 retracted within portal sleeve 564 to be in a safe, protected position, the rest state coinciding with the retracted position for the penetrating member illustrated in FIG. 12. In the rest state, push member 571 is fully inserted in hub 566 with pin 579 disposed at a proximal end of the groove 577 and nub 581 disposed in the longitudinal slot 583 at a distal end thereof. When it is desired to utilize the instrument 560 to penetrate tissue and enter an anatomical cavity, knob 575 is rotated counterclockwise looking distally at FIG. 12 such that pin 579 and groove 577 cause the push member 571 to move proximally, longitudinally relative to the hub withdrawing the push member therefrom until a distal end of the groove 577 is disposed in the collar 573 with the pin 579 received therein in a ready position for the instrument as illustrated in FIG. 13. With the push member 571 withdrawn, the nub 581 is no longer longitudinally aligned with the slot 583 but, rather, is aligned with a solid portion of the retraction plate 594 offset 180° from the slot. The knob 575 is then rotated clockwise looking distally at FIG. 13 causing movement of the push member 571 longitudinally into the hub with movement of the retraction plate distally via engagement with nub 581. Once the push member has been fully inserted in the hub, the instrument will be in the extended position shown in FIG. 9 with the retraction plate 594 locked in place against the locking member 622 and the nub 581 longitudinally aligned with the slot 583. In the extended position, the junction 584 will be substantially aligned with the distal end of the portal sleeve and the distal end 569 of the probe 565 will be disposed beyond the facet or end surface 582 with the cushion and operating springs positioning the operating member in the initial position proximally of the trigger member 624. When the instrument 560 is forced against tissue, such as tissue T forming a wall of an anatomical cavity, the probe 565 will be moved proximally as shown in FIG. 10 causing the operating member 588 to be moved proximally without bending or flexing the arm 618. Once a distal end of the sleeve 564 has entered the anatomical cavity, the probe 565 will be moved distally, and the momentum of the operating spring 598 moves the operating member 588 distally of the initial position to engage trigger member 624 and flex arm 618 in a direction outwardly from the instrument axis to release the retraction plate 594 as illustrated in FIG. 11. Once the retraction plate is released, retracting spring 602 automatically moves the penetrating member and with it the probe to a retracted position with the slot 583 moving along the nub 581. In the retracted position, the tip 578 of the penetrating member is disposed within the portal sleeve and the tip of the probe is disposed within the penetrating member as illustrated in FIG. 12. The instrument 560 can be reset in the extended position by withdrawing push member 571 from the hub to align nub 581 with the solid portion of the retraction plate and reinserting the push member in the hub to move the retracting mechanism distally.

The probe 565 can be arranged in the penetrating member 562 in many various ways, and FIGS. 14–17 illustrate by way of example alternative arrangements for the probe within the penetrating member where the probe is offset from a longitudinal axis of the penetrating member. In FIG. 14, the penetrating member distal end includes three equally spaced end surfaces or facets 582 joined along three edges 585 terminating distally at tip 578 and proximally at a junction joining the facets to body 574 with the probe 565 protruding through one of the end surfaces inwardly of the junction, i.e. inwardly of the circumference of body 574, a substantially equal angular distance from the edges 585 of the one end surface. The penetrating member of FIG. 15 includes three equally spaced end surfaces 582 joined along edges 585 with the probe 565 protruding in part through two adjoining end surfaces 582 inwardly of the circumference of the body 574 and along the edge 585 joining the two end surfaces. In FIG. 16, the penetrating member includes three equally spaced end surfaces 582 joined along edges 585 with the probe 565 protruding in part through two adjoining end surfaces along the edge 585 joining the two end surfaces and along the circumference of the body 574. The penetrating member of FIG. 17 includes three equally spaced end surfaces 582 joined along edges 585 with the probe 565 protruding through one of the end surfaces along the circumference of the body 574 a substantially equal angular distance from the edges of the one end surface. It will be appreciated that the arrangements for the probe illustrated in FIGS. 14–17 are exemplary only and that the probe can be arranged in the penetrating member in many various ways in accordance with the structure for the probe and the configuration of the penetrating member. By positioning the probe to protrude from the penetrating member close to the junction 584 and the circumference of body 574, retraction of the penetrating member immediately upon the sleeve distal end entering the anatomical cavity can be realized.

Another modification of an automatic retractable safety penetrating instrument according to the present invention is illustrated at 660 in FIG. 18. Penetrating member 662 of instrument 660 is made up of a distal part 670 and an end part 672, the distal part 670 having a distal end 676 defined by end surfaces 682 tapering distally to tip 678 and terminating proximally at a scalloped junction 684 joining the facets to a cylindrical neck 686 which in turn is joined to an elongate body 674 having an outer diameter or size less than the outer diameter of neck 686. Body 674 extends proximally from neck 686 to terminate at an end flange 687 disposed in the end part with body 674 passing through an opening in a forward wall of the end part. The end part forward wall is rigidly held between the end flange and a projection or plate 693 on body 674 such that the distal and end parts move together as a unit. End part 672 terminates proximally at an operating member or flange 688 at a proximal end of the penetrating member disposed in hub 666, the end part being hollow or tubular or formed with an internal passage to receive a push member 671 that is the same as push member 571 for setting the instrument in the ready and extended positions as was described for automatic retractable safety penetrating instrument 560. Operating spring 698 is connected between operating flange 688 and the rear wall of the hub to bias the penetrating member in a distal direction, and cushion spring 700 is connected between the operating flange and a retraction plate 694 disposed in the hub distally of the operating member to maintain the operating member at an initial position with the instrument in the extended position as shown in FIG. 18. As best illustrated in FIG. 19, retraction plate 694 has an opening therein allowing passage therethrough by the end part 672 with a leg 695 and an extension 697 extending proximally from the retraction plate at diametrically opposing locations. The leg 695 and extension 697 extend through respective slots in the operating flange 688 with retracting spring 702 connected between the leg 695 and the rear wall of the hub to bias the retraction plate in a proximal direction. A locking and releasing mechanism 712 for actuating retraction of the penetrating member includes a locking spring similar to that described for locking and releasing mechanism 612 except that trigger member 724 is disposed distally of locking member 722, the trigger member 724 being disposed on an extension 723 of arm 718. Extension 723 extends distally from locking member 722 with trigger member 724 disposed distally of the operating member in the initial position and the locking member in engagement with the extension 697 of the retraction plate in the normal condition for the locking spring illustrated in FIG. 18.

Operation of the automatic retractable safety penetrating instrument 660 is similar to that previously described for instrument 560 in that the push member 671 can be utilized to move the instrument from the rest to the ready position and thereafter to the extended position illustrated in FIG. 18 with the junction 684 of the penetrating member disposed beyond a distal end of the portal sleeve and the retraction plate 694 locked in place via engagement of extension 697 with the locking member 722 and the operating member 688 in the initial position disposed proximally of the trigger member 724. When the instrument 660 is forced through tissue to enter an anatomical cavity, the penetrating member 662 will be moved proximally causing proximal movement of the operating flange 688 to a set position with the locking member 722 serving as a stop or abutment limiting proximal movement of the operating flange. Upon the portal sleeve distal end entering the anatomical cavity, the operating flange will move distally, and the momentum of the operating spring 698 will cause movement of the operating member distally of the initial position to engage trigger member 724 and flex the locking spring to release the retraction plate 794.

An additional modification of an automatic retractable safety penetrating instrument according to the present invention is illustrated at 760 in FIG. 20, the instrument 760 being similar to automatic retractable safety penetrating instrument 460 in that movement of a safety shield distally upon a distal end of the portal sleeve entering an anatomical cavity is utilized to trigger retraction. As illustrated in FIGS. 20 and 22, the penetrating member 762 for automatic retractable safety penetrating instrument 760 has a distal end 776 defined by a plurality of facets 782 terminating distally at tip 778 and proximally at a junction 784 joining the facets to a body 774. As illustrated in FIGS. 20 and 21, the safety shield 763 has a distal end 767 joined to an elongate body concentrically disposed around the body of the penetrating member, the safety shield distal end being defined by one or more end surfaces 801 for being disposed along a corresponding facet or facets 782 of the penetrating member when the instrument is in an operative position during penetration of tissue as shown in FIG. 21. The end surfaces 801 of the safety shield are disposed at an angle with a longitudinal axis of the instrument 760 that is the same as the angle that the corresponding facet or facets 782 are disposed with the longitudinal axis such that the safety shield distal end completes or conforms to the geometric configuration of the penetrating member in the operative position. The penetrating member and safety shield distal ends can have various configurations to produce a predetermined solid or hollow geometric configuration in the operative position. Body 774 terminates proximally at a retraction plate 794 disposed in hub 766, and one or more than one retracting spring 802 is connected between retraction plate 794 and the rear wall of the hub to bias the penetrating member in a proximal direction, one retracting spring being illustrated in FIG. 20 and two retracting springs being illustrated in FIG. 24. The safety shield terminates proximally at an operating member 788 disposed in hub 766 with an operating spring 798 disposed concentrically around the penetrating member and connected between the retraction plate 794 and the operating flange 788 to bias the safety shield in a distal direction. An end cap 806 similar to end cap 106 is mounted for longitudinal sliding movement relative to the hub by bias members including mounting springs 810 connected between the hub rear wall and the rear wall of the end cap to bias the end cap in a proximal direction. As best illustrated in FIGS. 20 and 23, a locking and releasing mechanism 812 for the instrument 760 includes a locking spring similar to that described for locking and releasing mechanism 712 in that arm 818 has an extension 823 extending distally from the locking member 822 to carry a trigger member 826 pivotally mounted on extension 823. Trigger member 826 includes a trigger cam 827 angled in a proximal direction and a leg 829 disposed parallel with extension 823 to allow proximal movement of the operating flange past the trigger cam without causing flexing of arm 818 and to cause flexing of arm 818 in response to distal movement of the operating member against the trigger cam. A notch or slot 833 can be formed in the retraction plate 794 to facilitate assembly of the instrument 760.

Operation of the automatic retractable safety penetrating instrument 760 is similar to that previously described for automatic retractable safety penetrating instrument 460 in that the instrument can be supplied in a rest state and moved to a ready position illustrated in FIG. 20 by releasing the end cap 806 from the hub 766. In the ready position, the penetrating member 762 and safety shield 763 are in a retracted position with end cap 806 biased proximally. End cap 806 is moved distally to set the instrument in the extended position illustrated in FIG. 24, the arm 818 serving as a push member for moving the retracting mechanism distally via engagement of the locking member 822 with the retraction plate 794. Once the protrusion 828 has entered the hub through the slot in the hub rear wall, the end cap will be locked in place at which time the retraction plate 794 is locked or held in place against the locking member 822. With the instrument in the extended position, the junction 784 of the penetrating member will be aligned with the distal end of the portal sleeve, and the distal end of the safety shield will be disposed beyond the tip 778 of the penetrating member. When the instrument 760 is forced through tissue forming a wall of an anatomical cavity, the safety shield will move proximally causing proximal movement of the operating member 788 past the trigger cam 827 without causing flexing of arm 818. In the operative position, the end surfaces 801 of the safety shield will be disposed along the corresponding facets 782 of the penetrating member to produce a predetermined geometric configuration. Once the distal end of the portal sleeve has entered the anatomical cavity, the safety shield 763 will be moved distally causing distal movement of the operating member 788 to engage trigger cam 827 and pivot leg 829 causing arm 818 to flex and release the retraction plate 794. Accordingly, retracting spring 802 will move the penetrating member and with it the safety shield to the retracted position shown in FIG. 20.

As illustrated in FIGS. 25 and 26 the hub 766 can have a side wall thereof formed with a central recessed channel 835 with a slot 837 formed in the hub wall to be disposed in the recessed channel. The slot 837 includes a longitudinal slot portion 839, a proximal transverse slot portion 841 and a distal transverse slot portion 843. A pin 845 is threadedly secured on the penetrating member, such as in the periphery of retraction plate 794, the pin 845 extending through the longitudinal slot portion 839 to terminate at an external knob 818 with the location of the proximal transverse slot portion 841 corresponding to the location of the pin 845 in the extended position. A pin 847 is secured to the safety shield, such as in the periphery of the operating flange 788, the pin 847 similarly extending through the longitudinal slot portion 839 to terminate at an external knob with the location of the distal transverse slot portion 843 corresponding to the location of the pin 847 in the extended position. The length of the longitudinal slot portion is sufficient to allow movement of the safety shield and the penetrating member between the extended and retracted positions with the knobs moving within the longitudinal slot portion. Where retraction is not desired, the pin 845 can be moved into the proximal transverse slot portion 841 preventing retraction of the penetrating member and safety shield such that the safety shield distal end is disposed beyond the tip of the penetrating member upon the portal sleeve distal end entering an anatomical cavity for use as a standard safety trocar instrument. Where it is desired to penetrate tissue with the safety shield distal end disposed beyond the tip of the penetrating member, pin 847 can be moved into the distal transverse slot portion 843 to lock the safety shield against proximal movement; and, accordingly, retraction of the penetrating member will be prevented. Where the safety shield distal end does not complete the configuration of the penetrating member distal end in the operative position and it is desired that the safety shield distal end be locked in a position substantially aligned with the portal sleeve distal end for use as a standard trocar instrument, an intermediate transverse slot portion 849 can be provided along the slot 837 corresponding in location to the location of pin 843 when the safety shield is in the retracted position allowing the pin 847 to be moved into the intermediate transverse slot portion as shown in dotted lines in FIGS. 25 and 26. A probe can be used with the instrument 760 to trigger retraction; and, as shown in FIG. 22, a probe 765 can be mounted within the penetrating member 762 to extend through a hole in an end surface or facet 782. Various types of release mechanisms can be used with the instrument 760 to release the end cap from the hub allowing the instrument to be reset in the extended position.

A modification of the automatic retractable safety penetrating instrument according to the present invention is illustrated at 860 in FIG. 27 wherein safety shield 863 includes a distal end 867 having a configuration that is the same as the configuration of the distal end 876 of the penetrating member 862 such that the safety shield can be utilized to cut tissue when disposed beyond the distal end of the penetrating member as illustrated in FIG. 27. As shown in FIG. 27, distal end 867 of safety shield 863 has a plurality of end surfaces or facets 901 tapering distally to a sharp tip 903, and the penetrating member distal end 876 includes a plurality of corresponding facets 882 tapering distally to sharp tip 878 with the facets 901 of the safety shield being disposed at an angle with the longitudinal axis of the penetrating member that is the same as the angle that the facets 882 are disposed with the longitudinal axis. By forming the safety shield distal end of a severable material, the distal end 867 of the safety shield can be cut prior to use to remove the sharp tip 903 where use of the safety shield to cut tissue is not desired.

Another modification of the automatic retractable safety penetrating instrument according to the present invention is illustrated at 960 in FIG. 28 wherein the penetrating member 962 is in the nature of a cannulated needle having a distal end 976 defined by an angled edge 982 terminating distally at a sharp tip 978. A safety probe 965 is disposed concentrically within the penetrating member, the safety probe 965 having a distal end 969 with an angled end surface 905. The edge 982 of the penetrating member is disposed at an angle with the longitudinal axis of the penetrating member that is the same as the angle that the end surface 905 is disposed with the axis such that the probe and penetrating member form a substantially smooth, solid geometric configuration in the operative position. Instrument 960 can be designed to allow removal of the probe and the penetrating member together or individually from the portal unit, and the probe can remain extended beyond the distal end of the portal sleeve upon retraction of the penetrating member as was described for the safety shield in instrument 760.

Figure 29:
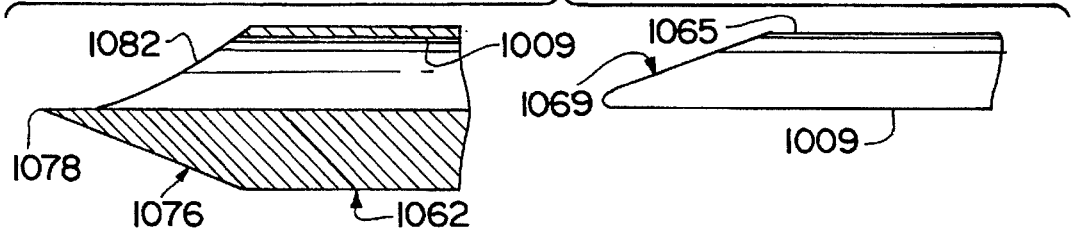
FIGS. 29 and 30 are exploded views of the distal ends of automatic retractable safety penetrating instruments according to the present invention having cannulated penetrating members.

Another embodiment of an automatic retractable safety penetrating instrument according to the present invention is illustrated in FIG. 29 wherein a hollow penetrating member 1062 is partially solid having a passage 1007 therethrough of a semicircular configuration in cross-section. A distal end 1076 of the penetrating member has a partially conical configuration terminating at a sharp tip 1078 from which extends a peripheral edge 1082 forming an opening in the distal end of the penetrating member. A safety probe 1065 is formed of a solid elongate member 1009 having a semicircular configuration in cross-section and terminating at a distal end 1069 having a partially conical configuration corresponding to the configuration of the distal end of the penetrating member.

Figure 31:
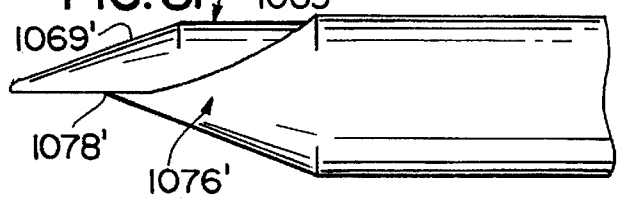
FIG. 31 is a side view of the distal ends of FIGS. 29 and 30 with the safety probe in the extended position.
Figure 32:
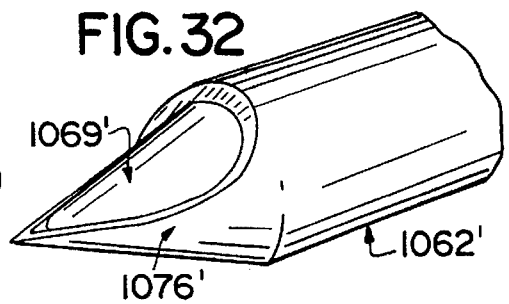
FIG. 32 is a perspective view of the cannulated penetrating members of FIGS. 29 and 30 with the probe in a retracted position.
Figure 33:
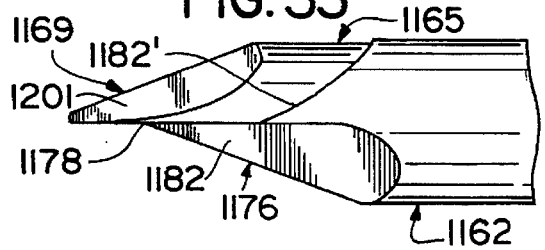
FIG. 33 is a side view of a trocar-like cannulated penetrating member for use with the automatic retractable safety penetrating instrument of the present invention.

In the extended position, the distal end 1069 of the safety probe will protrude beyond sharp tip 1078 to protect the tip as shown in FIG. 31; and, during penetration of tissue, the safety probe will move to the retracted position as shown in FIG. 32 such that the distal end 1069 of the safety probe is positioned within the opening formed by peripheral edge 1082 in substantial alignment to form, with distal end 1076 of the penetrating member, a solid geometrical configuration similar to a trocar. By utilizing the positive stop mechanisms previously illustrated, the safety probe will be prevented from retracting further than the position corresponding with the configuration of the penetrating member such that the conical configuration of the penetrating distal end of the safety penetrating instrument is assured as shown in FIG. 32.

Figure 30:
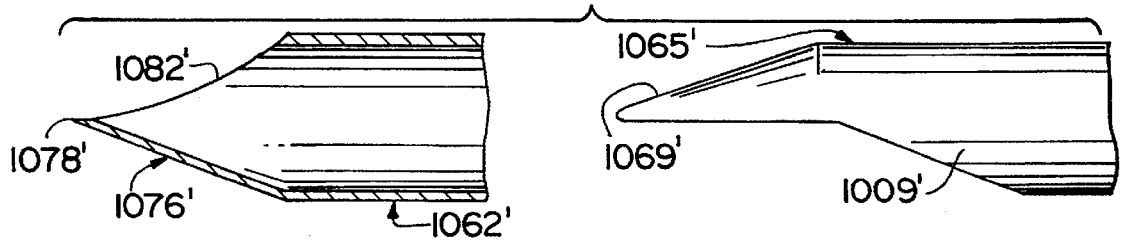

FIG. 30 shows a modification of the automatic retractable safety penetrating instrument of FIG. 29 wherein a penetrating member 1062' has the same external configuration as penetrating member 1062 but is tubular and the safety probe 1065' has an elongate member of circular configuration in cross-section corresponding to the tubular configuration of the penetrating member. The safety penetrating instrument of FIG. 30 will assume the same configuration as the safety penetrating instrument of FIG. 29 in the extended position as shown in FIG. 31 and the retracted position as shown in FIG. 32.

Figure 34:
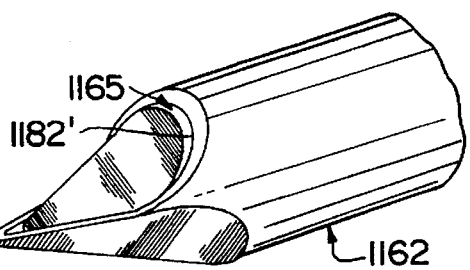
FIGS. 34, 35 and 36 are perspective top and bottom views of the penetrating member of FIG. 33 with the probe in a retracted position.
Figure 35:
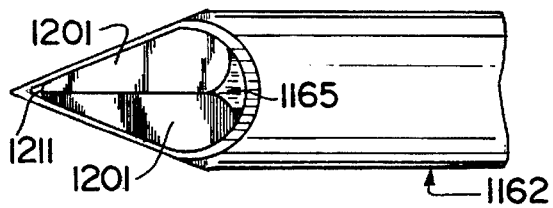
Figure 36:
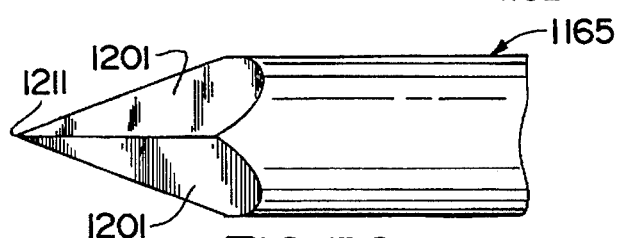

A modification of the automatic retractable safety penetrating instrument of FIG. 29 is illustrated in FIGS. 33, 34, 35 and 36 wherein the safety probe and penetrating member cooperate to produce a solid geometric pyramid configuration. More particularly, a hollow penetrating member 1162, which can be either tubular similar to the penetrating member illustrated in FIG. 30 or have a passage therethrough similar to the penetrating member illustrated in FIG. 29, has a distal end 1176 having a partial geometric configuration of a pyramid with sides or facets 1182 tapering to a sharp tip 1178 while an opening in the distal end defined by a peripheral edge 1182' terminates at sharp tip 1178. A safety probe 1165 has a cross-sectional configuration corresponding to that of the hollow penetrating member and has a distal end 1169 formed of sides or facets 1201 tapering to a narrow end, the configuration of the distal end 1169 cooperating with the configuration of the distal end 1176 of the penetrating member, when the safety probe is in the retracted position as illustrated in FIGS. 34 and 35, to produce a substantially complete geometric pyramid configuration having four sides or facets symmetrically arranged around a sharp point 1178.

Still a further modification of an automatic retractable safety penetrating instrument according to the present invention is illustrated in FIG. 37 at 1260, the instrument 1260 being similar to automatic retractable safety penetrating instrument 760 except that safety shield 1263 for automatic retractable safety penetrating instrument 1260 terminates distally at a peripheral scalloped edge 1213 and proximally at an operating member or flange 1288 disposed in hub 1266 with cushion spring 1300 disposed around the body of the safety shield and connected between the operating flange 1288 and the front wall of the hub. Operating spring 1298 is disposed around the penetrating member and connected between the operating member and the retraction plate 1294 such that the operating member 1288 is maintained at an initial position with the instrument in the extended position illustrated in FIG. 37. The locking and releasing mechanism 1312 for automatic retractable safety penetrating instrument 1260 is similar to the locking and releasing mechanism 812; however, the locking spring for locking and releasing mechanism 1312 has two protrusions 1328 and 1328' with protrusion 1328' distally spaced from protrusions 1328.

Operation of automatic retractable safety penetrating instrument 1260 is similar to that previously described in that instrument 1260 is moved to the extended position via squeezing operation of end cap 1306 causing arm 1318 to move retraction plate 1294 distally until protrusion 1328 enters the hub at which time the end cap 1306 will be locked in place with protrusion 1328' disposed within the hub distally of protrusion 1328 and the retraction plate 1294 locked in place against the locking member 1322. In the extended position, operating flange 1288 will be disposed in the initial position proximally of trigger cam 1327, and the distal edge 1213 of the safety shield will be disposed proximally of the tip 1278 of the penetrating member 1262. When the instrument 1260 is forced through tissue to enter an anatomical cavity, safety shield 1263 will be moved proximally causing proximal movement of operating flange 1288; and, upon the portal sleeve distal end entering the anatomical cavity, operating flange 1288 will be moved distally of the initial position to engage trigger cam 1327 and pivot leg 1329 thusly flexing arm 1318 to release retraction plate 1294. Accordingly, retracting spring 1302 will move the penetrating member and with it the safety shield proximally causing the retraction plate 1294 to engage protrusion 1328' such that arm 1398 is pivoted in a direction outwardly from a longitudinal axis of the instrument causing protrusion 1328 to be aligned with the slot 1320 in the hub rear wall to automatically release the end cap in response to movement of the penetrating member to the retracted position.

An additional modification of an automatic retractable safety penetrating instrument according to the present invention is illustrated at 1360 in FIG. 38. Automatic retractable safety penetrating instrument 1360 is similar to automatic retractable safety penetrating instrument 60 except that the operating member, the retraction member, the locking and releasing mechanism, the push member and the valve assembly for instrument 1360 are different than those for instrument 60. The penetrating member 1362 for automatic retractable safety penetrating instrument 1360 terminates proximally at an operating member or flange 1388 having an ear 1315 projecting outwardly therefrom; however, depending on the configuration for the operating flange, ear 1315 need not be provided. The retraction member for instrument 1360 is in the nature of a U-shaped member defining a retraction plate 1394, a forward or engagement wall 1351 distally spaced from the retraction plate and a connecting or sidewall 1353 joining the engagement wall to the retraction plate with the penetrating member 1362 passing through a hole in the engagement wall 1351. Operating spring 1398 is disposed concentrically around control tube 1396 and connected between the operating flange 1388 and the retraction plate 1394 to bias the penetrating member distally with operating flange 1388 in abutment with the engagement wall 1351. Retracting spring 1402 is disposed concentrically around control tube 1396 and connected between the rear wall of the hub 1366 and the retraction plate 1394 to bias the retracting member in a proximal direction. The locking and releasing mechanism 1412 for automatic retractable safety penetrating instrument 1360 is best shown in FIGS. 39, 39a and 40 and includes a latch or locking spring having a base 1414 for being secured to a wall of hub 1366 with arm 1418 joined to base 1414 by a bend or angle 1416, the arm 1418 being in the nature of a plate or flat piece of material. A locking member 1422 protrudes beyond a longitudinal edge of arm 1418 to engage retraction plate 1394 and prevent proximal movement thereof in a normal condition for the latch in the extended position for the instrument illustrated in FIG. 38. A trigger or release member 1426 protrudes from the longitudinal edge parallel with and distally spaced from the locking member 1422, the trigger member 1426 being disposed in the normal condition in the path of longitudinal movement of ear 1315 or operating flange 1388 where ear 1315 is not provided. Arm 1418 can be bent from base 1414 at a right angle along bend 1416 as shown in FIG. 39, or the arm can be joined to the base by a curved U-shaped bend 1416 as illustrated in FIG. 39a allowing arm 1418 to pivot around a pivot axis extending along the angle or bend. Locking member 1422 is in the nature of a cylindrical protrusion or pin, and trigger member 1426 is in the nature of a flat strip of material angled in a proximal direction from arm 1418 to allow proximal movement of ear 1315 thereby without causing pivoting of arm 1418. Various mechanisms including a pin secured on the retracting member and projecting through a slot in the hub can be utilized in the instrument 1360 to set the instrument in an extended position by moving the retracting mechanism distally such that retraction plate 1394 is moved distally to be locked against locking member 1422. As shown in FIG. 38, an end cap 1406 and push member 1471 are provided in the instrument 1360, the push member being in the nature of a spring arm mounted in end cap 1406 and having a bent end for engaging the retraction plate with a protrusion 1428, the push member being similar to the locking and releasing mechanisms previously described for use as push members. The valve assembly for instrument 1360 includes a one-piece, hollow cylindrical, truncated conical or tubular valve body 1438 having a peripheral flange for mounting in a rear end of housing 1368. Valve body 1438 is made from flexible, stretchable, elastic or resilient material, such as silicone or rubber, and is provided with one or more than one slit 1455 extending longitudinally therealong allowing instrument of various sizes to be inserted through the lumen of the valve body with the valve body conforming to the size of the instruments to produce a seal therewith.

Operation of automatic retractable safety penetrating instrument 1360 is similar to that previously described in that the instrument is moved to the extended position via squeezing operation of retracing mechanism distally to the extended position illustrated in FIG. 38. In the extended position, the junction 1384 of the penetrating member 1362 is disposed beyond the distal end of the portal sleeve 1364, operating member 1388 is in the initial position abutting engagement wall 1351 to be disposed distally of trigger member 1426, trigger member 1426 is disposed in the path of longitudinal movement of the ear 1315 and retraction plate 1394 is locked in place against locking member 1422. In order to facilitate movement of the retraction plate 1394 distally past the locking member when setting the instrument in the extended position, a forward edge 1457 of the retraction plate can be angled as shown in FIG. 41. With the instrument in the extended position, locking member 1422 will engage the retraction plate 1394 just inwardly of the forward edge 1457 as best illustrated in FIG. 41. Once the retraction plate is locked in place against the locking member 1422, further squeezing of the end cap 1406 causes the angled distal portion of protrusion 1428 to be engaged by the hub rear wall causing the push member 1471 to be pivoted in a direction outwardly form a longitudinal axis of the instrument such that the bent end is disengaged from the retraction plate. The push member will be moved out of the path of movement of the retraction plate with protrusion 1428 locking the end cap relative to the hub. When instrument 1360 is utilized to penetrate tissue, penetrating member 1362 will be moved proximally causing proximal movement of operating flange 1388 and with it ear 1315 to a set position such that junction 1384 is substantially aligned with the distal end of the portal sleeve in an operative position for the instrument, and compression of the operating spring can serve as a positive stop limiting proximal movement of the penetrating member. Ear 1315 moves proximally by trigger member 1326 causing arm 1418 to pivot around the pivot axis, i.e. over the trigger member as illustrated in FIG. 42, inwardly toward a longitudinal axis of the instrument with the pivot axis being parallel with the instrument axis. Accordingly, locking member 1422 will move inwardly along the retraction plate 1394 further from the edge 1457 as shown by the arrow in FIG. 42 such that the retraction plate 1394 remains locked in place. Once the distal end of the portal sleeve has entered the anatomical cavity, penetrating member 1362 will be moved distally causing distal movement of the operating member 1388 toward the initial position with ear 1315 moving distally, i.e. under the trigger member 1426 as shown in dotted lines in FIG. 43, causing arm 1418 to pivot around the pivot axis in a direction outwardly from the instrument axis and toward base 1416 such that the locking member 1422 is moved outwardly of the edge 1457 as shown by the arrow in FIG. 43 thusly releasing the retraction plate 1394. Accordingly, retracting spring 1402 will move the retraction member and with it the penetrating member to the retracted position. It will be appreciated that the locking member 1422 can have various structural configurations to prevent proximal movement of the retracting mechanism and to release the retraction member in response to pivoting of the latch around an axis parallel with the instrument axis. Trigger member 1426 can have various configurations to allow proximal movement of the operating member thereby without releasing the retraction plate and to cause pivoting of arm 1418 around the pivot axis in response to distal movement of the operating member toward the initial position. The operating member 1388 can have various configurations with or without ear 1315 to move proximally by the trigger member 1426 without causing disengagement of locking member 1422 from retraction plate 1394 to pivot arm 1418 to release the retraction plate in response to distal movement of the operating member toward the initial position. While one locking and releasing mechanism 1412 is provided in the instrument 1360, more than one locking and releasing mechanism can be provided. The locking and releasing mechanism 1412 can be made in many various ways including a length of wire bent in a desired configuration to form the locking and trigger members and an elongated strip or bar with the trigger and locking members thereon. The locking and releasing mechanism can be made of a spring material to produce the desired pivotal or flexing movement or the locking and releasing mechanism can be pivotably or rotatably mounted in the instrument and biased to the normal position. Depending upon its configuration, the locking and releasing mechanism can be pivotally mounted in many ways; and, where the locking and releasing mechanism is made from a wire or strip of material, one or both ends of the wire or strip can be pivotally secured in the instrument to mount the locking and releasing mechanism for pivotal movement around an axis parallel with the longitudinal axis of the instrument with a torsional bias biasing the locking and releasing mechanism to the normal position. Another modification of an automatic retractable safety penetrating instrument according to the present invention is illustrated at 1460 in FIG. 44, the instrument 1460 being similar to the instrument 1360 except that the retraction member for instrument 1460 includes only the retraction plate 1494 with the locking member 1522 disposed distally of the trigger member 1526 to lock the retraction plate against a front wall of the hub 1466 in the extended position for the instrument.

In use, instrument 1460 is forced through tissue causing proximal movement of operating member 1488 by trigger member 1526 to the set position to produce pivotal movement of the locking and releasing mechanism 1512 without disengaging locking member 1522 from retraction plate 1494. Upon a distal end of the portal sleeve entering the anatomical cavity, the operating member 1488 will be moved distally toward the initial position to engage trigger member 1526 and pivot the locking and releasing mechanism 1512 around an axis parallel with a longitudinal axis of the instrument in a direction outwardly from the longitudinal axis such that the retraction plate is released for retraction by retracting spring 1502. By forming the locking member as a retraction plate only and by positioning the locking member distally of and close to the trigger member, the space required for the locking and releasing mechanism can be reduced allowing the length of the hub 1466 to be minimized.

A still further modification of an automatic retractable safety penetrating instrument according to the present invention is illustrated in FIG. 45 at 1560. Automatic retractable safety penetrating instrument 1560 is similar to automatic retractable safety penetrating instrument 1460; however, a safety shield 1563 is utilized in instrument 1560 to trigger retraction, the safety shield terminating proximally at an operating member 1588. The locking and releasing mechanism 1612 for instrument 1560 is similar to locking and releasing mechanism 1512; however, the operating member 1588 for automatics retractable safety penetrating instrument 1560 is positioned by an operating spring 1598 and a cushion spring 1600 in an initial position disposed proximally of a trigger member 1624 with the instrument in the extended position illustrated in FIG. 45. The penetrating member 1562 terminates proximally at retraction plate 1594 with the operating spring connected between the retraction plate and the operating member and the cushion spring connected between the operating member and the front wall of hub 1566. Instead of a spring, the retracting mechanism for instrument 1560 includes a magnetic bias with magnets 1669 being mounted in a rear wall of the hub 1566 and the retraction plate 1594 being made of a magnetizable material. Where use of magnets 1659 in the hub rear wall is not desired, the rear wall of the hub can be made of a material having one polarity with the retraction plate being made of a material having the opposite polarity. End cap 1606 is movably mounted relative to hub 1566 by bias members including mounting springs 1610 secured between a rear wall of the end cap and attachment blocks 1661 secured to and disposed in hub 1566. A push member 1671 is mounted in end cap 1600 for setting the instrument in the extended position, the push member 1671 being similar to push member 1471. An end cap release mechanism for locking the end cap relative to the hub and for releasing the end cap from the hub includes an actuating button 1630 made up of a spring 1631 externally secured on skirt 1608 of end cap 1606, the spring 1631 having a normal condition defining one or more than one bumps or protrusions for being received in an opening in a wall of the hub 1566 with the instrument in an extended position as illustrated in FIG. 45 and for being moved to a collapsed or flattened position allowing the end cap to be released from the hub.

Operation of the automatic retractable safety penetrating instrument 1560 is similar to that previously described in that the instrument can be moved to the extended position by squeezing end cap 1606 causing push member 1671, via engagement with the retraction plate 1594, to move the penetrating member and with it the safety shield distally such that the retraction plate is moved past locking member 1622 to be locked in place. Continued squeezing of the end cap causes protrusion 1628 to enter the hub such that the push member is flexed in a direction outwardly from the instrument axis to be disengaged from the retraction plate. Distal movement of the end cap causes spring 1631 to be collapsed or flattened until it is aligned with the opening in the hub at which time the push member will be out of the path of movement of the retraction plate 1594 and the operating member 1588. Once aligned with the opening in the hub, spring 1631 will return to the normal condition locking the end cap in place. During penetration of tissue, safety shield 1563 will be moved proximally such that operating member 1588 is moved proximally from the initial position to a set position in the operative position for the instrument. Upon a distal end of the portal sleeve entering the anatomical cavity, the safety shield will be move distally causing operating member 1588 to be moved distally of the initial position to engage trigger member 1624 and pivot the locking and releasing mechanism 1612 around an axis parallel with a longitudinal axis of the instrument to release the retraction plate 1594. Accordingly, the magnetic bias will move the penetrating member and the safety shield to the retracted position.

A modification of a locking and releasing mechanism for use with the automatic retractable safety penetrating instruments according to the present invention is illustrated at 1712 in FIG. 46, the locking and releasing mechanism 1712 being similar to locking and releasing mechanisms 1412, 1512 and 1612 except that locking and releasing mechanism 1712 is made from a length of metal or plastic wire or filament bent to define a locking member 1722 and a trigger member 1726. Locking and releasing mechanism 1712 has ends formed as or secured to coil springs 1799 for torsionally biasing the locking and releasing mechanism to a normal position when the ends are secured, such as to the front and rear walls of the hub of an automatic retractable safety penetrating instrument.

Figure 47:
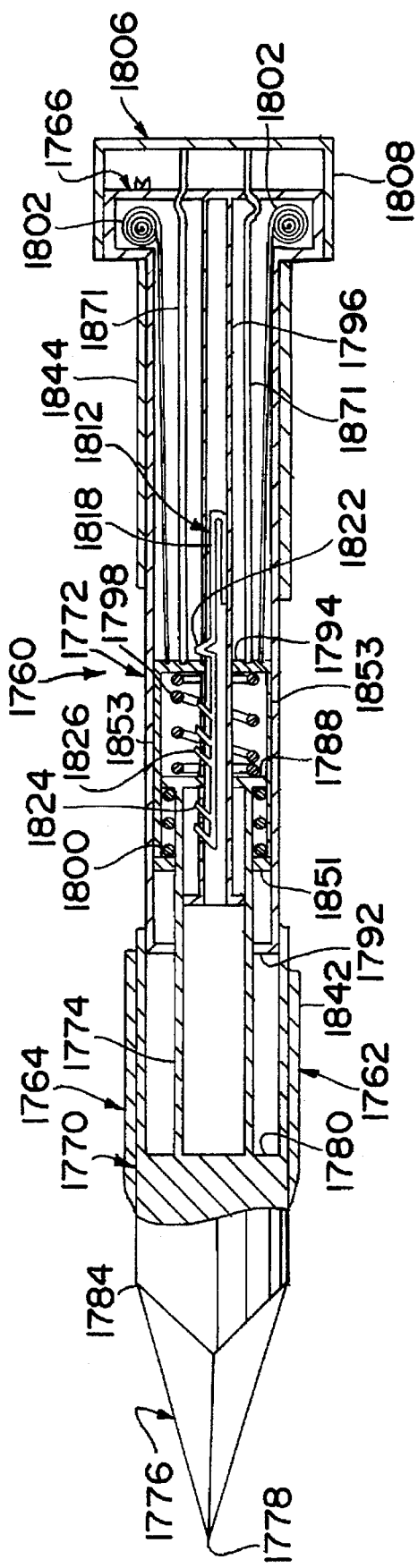
FIG. 47 is a side view, partly in section, of an automatic retractable safety penetrating instrument according to the present invention having a penetrating member formed of a distal end telescoping with respect to a shaft.
Figure 48:
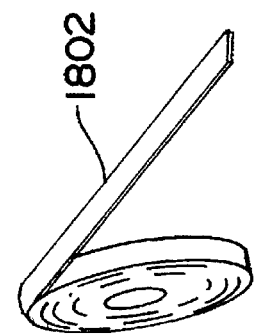
FIGS. 48 and 49 are perspective views of retracting springs for the instrument of FIG. 47.

Yet another modification of an automatic retractable safety penetrating instrument according to the present invention is illustrated in FIG. 47 at 1760, only the penetrating unit for the instrument 1760 being shown. Penetrating member 1762 for instrument 1760 is made up of a distal part 1770 mounted for telescoping movement relative to a tubular end part 1772. Distal part 1770 has a distal end 1776 terminating distally at tip 1778 and proximally at a junction 1784 joining the distal end to an elongate outer tubular body 1842. Outer body 1842 is concentrically disposed around an inner body 1774 extending proximally from an internal end wall or shoulder 1780 disposed in outer body 1842 transverse to a longitudinal axis of the instrument. Inner body 1774 terminates proximally at an operating member 1788 disposed in end part 1772 with the inner body passing through an opening in a forward or stop or abutment wall 1792 at a distal end of the end part 1772. The distal end of end part 1772 is disposed in outer body 1842 with the end part terminating proximally at a proximal end joined to or formed as part of hub 1766. A sheath 1844 is concentrically disposed around the end part 1772 at the proximal end thereof, the sheath terminating distally at a forward end spaced from the outer body 1842 by a distance that is equal to the retraction distance for the distal part 1770. Outer body 1842 has an outer diameter that is the same as the outer diameter of sheath 1844 to be received by the inner diameter of the portal sleeve 1764. A retracting member is disposed in the end part 1772 and includes a U-shaped or rectangular member defining a retraction plate 1794, one or more connecting or side walls 1853 extending distally from the retraction plate and a forward wall 1851 distally joined to side walls 1853 with the forward wall having an opening therein allowing passage therethrough by the inner body 1774. Inner body 1774 is hollow or tubular or partly hollow or tubular to receive a control tube 1796 extending distally from a rear wall of the hub, the control tube passing through an opening in the retraction plate 1794. The retracting member defines an enclosure or structure for receiving the operating flange 1788, an operating spring 1798 concentrically disposed around the control tube and connected between the operating flange 1788 and the retraction plate 1794 to bias the distal part 1770 in a distal direction relative to the end part 1772 and a cushion spring 1800 concentrically disposed around the inner body 1774 and connected between the operating flange 1788 and the forward wall 1851 to bias the distal part in a proximal direction such that the operating flange is maintained at an initial position with the instrument in the extended position as illustrated in FIG. 47. One ore more than one retracting spring 1802 biases the retraction member in a proximal direction. Various different types of springs as well as other types of bias devices can be utilized in the instrument 1760 to bias the retracting member; and, as shown in FIG. 48, the retracting spring can be a torsion spring. As illustrated in FIG. 48, the retracting spring 1802 is a coil torsion spring that can be mounted in instrument 1760 with an end of the spring connected to the retraction plate 1794, such that the spring is unwound to bias the retraction member proximally in the extended position as illustrated in FIG. 47 and is rewound to move the retraction member proximally to a retracted position upon release of the retraction plate as will be explained further below, and the spring is wound and unwound about an axis transverse to the direction of movement of the penetrating member between the extended and retracted positions. The spring 1802 can be arranged in instrument 1760 in many ways including within or externally of the penetrating member or within the control tube, the hub or the valve housing to wind on an axis transverse to the direction of retraction. Locking and releasing mechanism 1812 for automatic retractable safety penetrating instrument is similar to locking and releasing mechanism 512 except that the locking and releasing mechanism 1812 is mounted within control tube 1796 with trigger members 1824 and 1826 extending through a longitudinal slot in the control tube to be disposed in the path of movement of operating flange 1788, the operating flange projecting inwardly from an internal surface of the wall of inner body 1774. Locking member 1822 for locking and releasing mechanism 1812 includes a protrusion on arm 1818 proximally spaced from trigger members 1826, the locking member having a distal portion disposed transverse to a longitudinal axis of the instrument to prevent proximal movement of retraction plate 1794 thereby and a proximal portion angled in a distal direction to permit distal movement of the retraction member thereby when setting the instrument in the extended position. Various different types of push members can be utilized in the instrument 1760 to move the retracting mechanism distally when setting the instrument in the extended position; and, as shown in FIG. 47, a pair of push members 1871 in the nature of arms connected between a rear wall of end cap 1806 and the retraction plate 1794 are provided. End cap 1806 has a skirt 1808 disposed externally of the hub 1766, and the distance that the end cap must be moved proximally in the ready position will be in accordance with the distance that the push member must be moved proximally to engage the retracting mechanism for movement to the extended position.

In use, the automatic retractable safety penetrating instrument 1760 can be moved to the extended position via squeezing operation of end cap 1806 causing movement of the retracting member distally unwinding springs 1802 with the proximal portion of locking member 1822 allowing the retraction member to move distally thereby until the retraction plate 1794 is locked in place against the distal portion of the locking member. With the instrument in the extended position, junction 1784 of the penetrating member 1762 will be disposed beyond the distal end of the portal sleeve 1764 and the operating member 1788 will be in the initial position disposed proximally of trigger members 1824 and distally of trigger members 1826. During penetration of tissue, the distal part 1770 is moved proximally relative to the end part 1772 causing proximal movement of operating member 1788 past trigger members 1826 to a set position without causing flexing of the arm 1818, and the instrument will be in the operative position with junction 1784 substantially aligned with the distal end of the portal sleeve. Once the distal end of the portal sleeve has entered the anatomical cavity, the distal part 1770 will be moved distally relative to the end part 1772 causing operating member 1788 to move distally toward the initial position to engage a distally closest trigger member 1826 causing flexing of arm 1818 such that locking member 1822 is moved into the control tube thusly releasing the retraction plate 1794. Once the retraction plate is released, springs 1802 are rewound moving the retraction member and with it the distal part 1772 of the penetrating member in a proximal direction to the retracted position with the tip 1778 disposed in the portal sleeve in a safe, protected position. Trigger members 1824 can be utilized to trigger retraction via movement of the operating member 1788 distally of the initial position.

Thus, it will be appreciated that in automatic retractable safety penetrating instrument 1760 the shaft of the penetrating member is formed of telescoping parts such that the distal end 1776 is retracted by telescoping proximal movement of the distal part of the penetrating member relative to the end part of the penetrating member whereby hub 1766 need not house any mechanism and need not provide any longitudinal space for retraction of the penetrating member distal end such that the length of the hub can be minimized. The retracting mechanism retracts the distal end until shoulder 1780 abuts wall 1792 such that the distal end is within the portal sleeve, and the sliding or telescoping movement between the parts of the penetrating member can be accomplished with other structural arrangements, for example, by eliminating outer tubular body 1842 to permit the distal part to telescope only within the end part.

Figure 49:
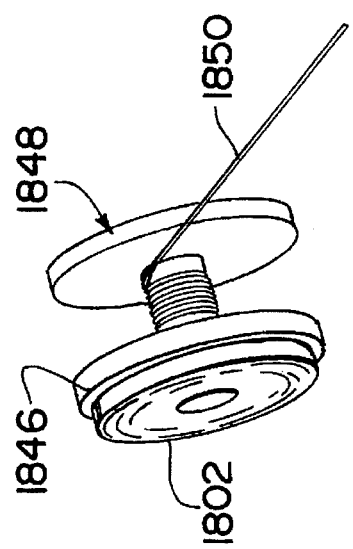

FIG. 49 illustrates an alternative arrangement for the retracting mechanism for the automatic retractable safety penetrating instrument 1760 wherein the torsion spring 1802 is connected to a flange 1846 of a spool 1848 having an axle for winding thereon of a connector 1850 secured between the spool and the retracting member. The connector can be a length of any suitable material including wire, synthetic plastic, string materials and the like for being in a wound condition on the spool 1848 in response to rotation of the spool by torsion spring 1802.

Yet another modification of an automatic retractable safety penetrating instrument according to the present invention is illustrated in FIG. 50 at 1860, only the penetrating unit for the instrument 1860 being shown. Penetrating member 1862 for instrument 1860 is made up of a distal part 1870 mounted for telescoping movement within a tubular end part 1872. Distal part 1870 includes a distal end 1876 proximally joined to a cylindrical neck 1886 at a junction 1884, the neck 1886 terminating proximally at a shoulder 1880. A body 1874 having an outer diameter or size less than the outer diameter of neck 1886 extends proximally from shoulder 1880 to be disposed within the end part 1872 with the body 1874 extending through an opening in a forward or abutment wall 1892 at a distal end of the end part. End part 1872 has an outer diameter that is the same as the outer diameter of neck 1886 to be received by the inner diameter of the portal sleeve. Body 1874 terminates proximally at an end wall 1852, and a tubular neck or extension 1954 extends proximally from the end wall to terminate at an operating flange 1888 disposed in end part 1872. A coil torsion operating spring 1898 is connected between operating member 1888 and abutment wall 1892, the spring 1898 being partially unwound to bias the distal part 1870 in a distal direction relative to the end part 1872. A retraction plate 1894 is disposed within the end part and has an opening therein allowing passage therethrough by the neck 1854. A coil torsion retracting spring 1902 is connected between the retraction plate 1894 and a non-movable part, such as a wall of end part 1872, of the instrument 1860, the retracting spring being unwound to bias the retraction plate in a proximal direction to abut the operating flange in the extended position for the instrument illustrated in FIG. 50. Connecting walls 1953 extend distally from retraction plate 1894 to terminate at a forward wall 1951 serving as a stop or abutment limiting proximal movement of the distal part 1870 during penetration of tissue. Locking and releasing mechanism 1912 for instrument 1860 is similar to the locking and releasing mechanism 112 except that two locking springs are provided in the instrument 1860 having triggers 1926 disposed proximally of the operating member 1888 in the initial position illustrated in FIG. 50. The locking springs for instrument 1860 can be utilized as push members or the locking springs can be utilized only for locking and releasing the retracting mechanism with separate push members provided for moving the instrument to the extended position.

Operation of the automatic retractable safety penetrating instrument 1860 is similar to that previously described in that the distal part 1870 of the penetrating member 1862 will be moved proximally relative to the end part 1872 during penetration of tissue causing proximal movement of operating member 1888 from the initial position past triggers 1926 to the set position at which time the instrument will be in the operative position with junction 1884 substantially aligned with the distal end of portal sleeve 1864. Movement of the operating member proximally causes operating spring 1898 to be further unwound with the forward wall 1951 serving as a positive stop limiting proximal movement of the distal part. Once the distal end of the portal sleeve has entered the anatomical cavity, operating spring 1898 will rewind causing the distal part 1870 to be moved distally relative to the end part 1872 such that the operating flange 1888 engages the distally closest triggers 1926 to flex the arms 1918 in a direction outwardly from a longitudinal axis of the instrument such that the retracting plate 1894 is released from the locking members 1922. Accordingly, retracting spring 1902 will rewind causing telescoping proximal movement of the distal part 1870 relative to the end part 1872 such that the distal end 1876 of the penetrating member 1862 is moved to a retracted position within the portal sleeve with abutment 1892 limiting retraction of the distal part.

A further modification of an automatic retractable safety penetrating instrument according to the present invention is illustrated in FIG. 51 at 1960. Automatic retractable safety penetrating instrument 1960 is similar to instrument 1760 except that the penetrating member 1962 for instrument 1960 does not have an outer body and the locking and releasing mechanism 2012 for instrument 1960 includes a latch that is similar to the latch for instrument 1360. The penetrating member 1962 for automatic retractable safety penetrating instrument 1960 includes a distal part 1970 mounted for telescoping movement relative to a tubular end part 1972. Distal part 1970 has a distal end 1976 terminating distally at tip 1978 and proximally at a junction 1984 joining the distal end to a cylindrical neck 1986 terminating proximally at an end wall or shoulder 1980. An elongate body 1974 extends proximally from shoulder 1980 to terminate at an operating member 1988 disposed in end part 1972, the neck 1986 having an outer diameter that is the same as the outer diameter of end part 1972. Body 1974 can be hollow or tubular or partly hollow or tubular as illustrated in FIG. 51 to receive an extension 1997 extending distally from retraction plate 1994 of a retraction member. A connecting wall 2053 extends distally from the retraction plate to terminate at a forward wall 2051 with the operating member 1988 being disposed between the forward wall and the retraction plate. The retraction member defines a structure for mounting the operating member 1988, an operating spring 1998 disposed around the extension 1967 and connected between the operating member and the retraction plate 1994 and a cushion spring 2000 disposed around body 1974 and connected between the operating member 1988 and the forward wall 2051 to position the operating member in an initial position with the instrument in the extended position as illustrated in FIG. 51. The latch or locking spring for locking and releasing mechanism 2012 includes a locking member 2022 engaged with retraction plate 1994 to prevent proximal movement thereof and a trigger member 2024 disposed distally of the operating member 1988 in the initial position. A coil torsion retracting spring 2002 connected with the retraction member is provided in the instrument 1960 to bias the retraction plate 1994 in a proximal direction. A push member 1971 can be provided for setting the instrument in the extended position.

Operation of automatic retractable safety penetrating instrument 1960 is similar to that described for instrument 1760 in that the distal part 1970 is moved proximally relative to the end part 1972 during penetration of tissue causing proximal movement of the operating member 1988 from the initial position to a set position at which time the instrument will be in an operative position with junction 1984 substantially aligned with the distal end of portal sleeve 1964. Once a distal end of the portal sleeve has entered the anatomical cavity, the distal part 1970 will be moved distally relative to the end part 1972 causing movement of operating member 1988 distally of the initial position to engage trigger 2024 such that the locking and releasing mechanism 2012 pivots around an axis parallel with a longitudinal axis of the instrument 1960 to release retraction plate 1994 from locking member 2022.

Another modification of an automatic retractable safety penetrating instrument according to the present invention is illustrated in FIG. 52 at 2060, the instrument 2060 being similar to automatic retractable safety penetrating instrument 60 except that the end part 2072 of penetrating member 2062 does not retract with the distal part 2070, and the valve assembly for instrument 2060 is different than the valve assembly for instrument 60. End part 2072 for penetrating member 2062 terminates distally at a stop or abutment 2092 and proximally at a proximal end secured in or formed with a front wall of hub 2066. Distal part 2070 includes a cylindrical body 2074 extending proximally from shoulder 2080 to terminate at an end wall 2152 with a tubular neck 2154 extending proximally from end wall 2152 to terminate at operating member 2088 disposed in hub 2066. A retraction plate 2094 is disposed in hub 2066 and has an opening therein allowing passage therethrough by neck 2154. A retracting spring 2102 is connected between the retraction plate 2094 and a rear wall of hub 2066 to bias the retraction plate in a proximal direction. A locking and releasing mechanism 2112 is disposed in hub 2066, the locking and releasing mechanism 2112 being similar to the locking and releasing mechanism 112 for automatic retractable safety penetrating instrument 60. End wall 2152 is disposed within the end part 2072, and an operating spring 2098 is disposed around neck 2154 and connected between the operating member 2088 and the retraction plate 2094 to bias the distal part 2070 in a distal direction. A cushion spring 2100 is disposed concentrically around neck 2154 and connected between the retraction plate 2094 and the end wall 2152 to bias the distal part in a proximal direction such that operating member 2088 is in an initial position disposed proximally of trigger member 2124 and distally of trigger members 2126 with the retraction plate 2094 held against the front wall of the hub via locking member 2122 in the extended position for the instrument illustrated in FIG. 52. The valve assembly for instrument 2060 is similar to the valve assembly disclosed in applicant's U.S. patent application Ser. No. 07/557,869, filed Jul. 26, 1990, the specification of which is incorporated herein by reference. The valve assembly includes a valve block 2158 having a peripheral flange for being disposed in a recess at a rear end of housing 2068 and a cylindrical member extending distally from the flange to mount a cylindrical or spherical valve body 2138. Valve body 2138 has a plurality of different size lumens or passages that can be selectively aligned with the open proximal end of the portal sleeve 2064 and a passage in the valve block to provide communication through housing 2068. The valve assembly includes a spring rotationally biased to maintain the valve body 2138 in a closed position wherein a solid surface of the valve body is aligned with the passage in the valve block to close off and seal the valve housing. An external ridge 2160 is provided on the valve body for rotating the valve body to an open position corresponding to one of the lumens being aligned with the passage. A pin 2117 protrudes distally from the front wall of hub 2066 for penetrating through the valve block 2158 and into the valve body 2138 when the hub 2066 is combined with the valve housing 2068 as illustrated in FIG. 52.

In operation, the hub 2066 is combined with the valve housing 2068 with pin 2117 penetrating the valve assembly to enter the valve body 2138 thusly preventing rotational movement of the valve body toward the closed position such that strain or friction on penetrating member 2062 is eliminated. When the instrument 2060 is forced through tissue, distal part 2070 will be moved proximally relative to end part 2072 causing proximal movement of operating member 2088 from the initial position to a set position at which time the instrument will be in the operative position. Once a distal end of portal sleeve 2064 has entered the anatomical cavity, distal part 2070 will move distally relative to end part 2072 causing movement of operating member 2088 distally toward the initial position to engage a trigger 2126 or distally of the initial position to engage trigger 2124 such that arm 2118 will be flexed releasing retraction plate 2094 from locking member 2122.

A still further modification of an automatic retractable safety penetrating instrument according to the present invention is illustrated in FIG. 53 at 2160, wherein only the penetrating unit for instrument 2160 is shown. Penetrating member 2162 for instrument 2160 includes a distal end 2176 joined to an elongate tubular or partly tubular body 2174 terminating proximally at an operating flange 2188 disposed in hub 2166. A control tube 2196 extends distally from a rear wall of end cap 2206 and into body 2174, the operating flange 2188 extending inwardly from an internal surface of the wall of the body to be disposed in a longitudinal slot 2191 in the control tube. A retraction plate 2194 is disposed in hub 2166, the retraction plate extending inwardly through a hole in body 2174 to be disposed in the slot 2191. Operating spring 2198 is disposed concentrically around the control tube and connected between a rear wall of hub 2166 and the operating flange 2188, and a cushion spring 2200 is disposed concentrically around body 2174 and connected between the operating flange 2188 and the retraction plate 2194 to position the operating flange in an initial position with the instrument in the extended position illustrated in FIG. 53. The locking and releasing mechanism 2212 for instrument 2160 is disposed within control tube 2196 and includes a latch or locking spring having an arm 2218 formed with a protrusion 2228 for locking the end cap 2206 within the hub 2166 in the extended position for the instrument, a locking member 2222 for holding the retraction plate 2194 against a front wall of hub 2166 and triggers 2224 and 2226. A stop or abutment in the nature of an additional bump or protrusion 2192 formed on arm 2218 serves as a positive stop limiting proximal movement of operating member 2188 during penetration of tissue. Actuating buttons 2230 for instrument 2160 are made up of casings or housings mounted in openings in skirt 2208 with helical springs 2231 disposed in the casings concentrically around release arms 2232 biasing the casings in a direction outwardly from a longitudinal axis of the instrument and allowing the casings to be moved inwardly toward the instrument axis to compress bend 2116. Although illustrated in FIG. 53 as extending through skirt 2208 adjacent a rear wall of the end cap, the buttons 2230 can be mounted at any suitable location in accordance with the location for the locking and releasing mechanism. A valve can be provided along the rear wall of end cap 2206 in communication with the lumen of the control tube 2196 to provide fluid flow through the instrument.

Automatic retractable safety penetrating instrument 2160 can be utilized to penetrate tissue and enter an anatomical cavity as previously described with the penetrating member moving proximally during penetration of tissue causing proximal movement of operating flange 2188 from the initial position to a set position at which time the instrument 2160 will be in an operative position. Upon the portal sleeve distal end entering the anatomical cavity, the penetrating member 2162 will be moved distally causing operating flange 2188 to move toward the initial position to engage trigger 2226 or distally of the initial position to engage trigger 2224 causing arm 2218 to move within control tube 2196 releasing locking member 2222 from retraction plate 2194 while protrusion 2228 remains engaged with the rear wall of the hub. Accordingly, retracting spring 2202 will move the retracting member 2194 and with it the penetrating member to a retracted position.

A still further modification of an automatic retractable safety penetrating instrument according to the present invention is illustrated in FIG. 54 at 2260. Penetrating member 2262 for automatic retractable safety penetrating instrument 2260 is similar to penetrating member 1962 for automatic retractable safety penetrating instrument 1960 and includes an elongate body 2274 joined to neck 2286 at shoulder 2280, the body 2274 terminating proximally at a retraction plate 2294 disposed in end part 2272. Body 2274 can be removably secured to neck 2286 such as by threads 2290 allowing distal end 2276 to be removed from body 2274 and replaced with various other distal ends of diverse configurations. A safety shield 2263 is disposed around the penetrating member 2262 and includes an outer body concentrically disposed around the neck 2286 and end part 2272 of the penetrating member and an inner tubular body 2274' joined to the outer tubular body at an internal shoulder or end wall 2280'. Inner body 2274' is concentrically disposed around body 2274 and terminates proximally at an operating member 2288 disposed in end part 2272 distally of retraction plate 2294 with body 2274' passing through an opening in a forward wall of the end part. A locking and releasing mechanism 2318 is mounted in end part 2272, the locking and releasing mechanism 2318 being similar to the locking and releasing mechanism 1812. A control tube 2296 extends from a rear wall of end cap 2306 and into body 2274, and a retracting spring 2302 is connected between retraction plate 2294 and a rear wall of hub 2266 to bias the distal part 2270 of the penetrating member in a proximal direction. Control tube 2296 can be rotatably, releasably mounted in end cap 2306 to be partially withdrawn from body 2274 with ears, nubs or projections provided on the control tube to allow the control tube to serve as a push member for setting the instrument in the extended position as disclosed in applicant's co-pending U.S. patent application Ser. No. 07/868,578 filed Apr. 15, 1992, the specification of which is incorporated herein by reference. An operating spring 2298 is disposed concentrically around body 2274 and connected between retraction plate 2294 and operating member 2288, and a cushion spring 2300 is concentrically disposed around body 2274' and connected between operating flange 2272 and the forward wall of end part 2278 to position the operating flange at an initial position in the extended position for the instrument illustrated in FIG. 54. In the extended position, operating flange 2288 will be in the initial position disposed proximally of triggers 2324 and distally of triggers 2326, and the retraction plate 2294 will be locked in place against locking member 2322.

Operation of automatic retractable safety penetrating instrument 2260 is similar to that previously described in that safety shield 2263 will move proximally during penetration of tissue causing movement of operating flange 2288 from the initial position to a set position at which time the instrument will be in an operative position. Once a distal end of the portal sleeve has entered the anatomical cavity, the safety shield will be moved distally causing movement of operating flange 2288 toward the initial position to engage a trigger 2326 or distally of the initial position to engage a trigger 2324 such that arm 2318 is flexed releasing retraction plate 2294 from locking member 2322. Accordingly, retracting spring 2302 will move the distal part 2270 of the penetrating member and, via engagement of shoulder 2280 with end wall 2280', the safety shield, to a retracted position. A probe can be utilized in the instrument 2260 in place of the safety shield to trigger retraction as shown in dotted lines at 2265. By utilizing a pin and slot arrangement, retraction of the distal part of the penetrating member and/or the safety shield and the probe where a probe is provided can be prevented.

Another modification of an automatic retractable safety penetrating instrument according to the present invention is illustrated in FIG. 55 at 2360, the instrument 2360 being similar to automatic retractable safety penetrating instrument 2260 in that a safety shield 2363 is utilized to trigger retraction. Penetrating member 2362 for instrument 2360 is made up of a distal part 2370 and an end part. 2372, the distal part including a distal end 2376 joined to an elongate body 2374 with an extension 2454 in the form of a plate extending proximally from an end wall 2452 of body 2374. Extension 2454 terminates proximally within the body of safety shield 2363 at a bent end defining a retraction member or including retraction plate 2394. End part 2372 includes a plate extending distally from a rear wall of hub 2366 and terminating distally at a bent or angled end with a retracting spring 2402 connected between the angled end of end part 2372 and the end wall 2452 of distal part 2370 to bias the distal part in a proximal direction. A locking and releasing mechanism 2412 similar to locking and releasing mechanism 2112 is disposed partly in hub 2366 and partly in the body of safety shield 2363 with a base 2416 of the locking and releasing mechanism being secured to end part 2372. A locking member 2422 of locking and releasing mechanism 2412 engages retraction plate 2394 to prevent proximal movement of the distal part 2370 when the instrument is in the extended position illustrated in FIG. 55. Safety shield 2363 is concentrically disposed around body 2374, the safety shield terminating proximally at an end flange disposed in hub 2366 with the body of the safety shield passing through an opening in a front wall of the hub. An operating member or flange 2388 projects inwardly from an inner surface of the wall of the safety shield body for engaging triggers 2424 or 2426 on arm 2418 of locking and releasing mechanism 2412. An operating spring 2398 is connected between the end flange and a rear wall of the hub, and a cushion spring 2400 is connected between the end flange and a front wall of the hub to position the operating member at an initial position proximally of triggers 2424 and distally of triggers 2426 in the extended position for the instrument. A push member 2371 can be provided in instrument 2360 to be moved by end cap 2406 to engage the end flange of the safety shield for use in setting the instrument in the extended position.

In operation, instrument 2360 is forced through tissue causing safety shield 2363 to be moved proximally such that operating member 2388 is moved proximally from the initial position to a set position without causing bending or flexing of arm 2418. Once a distal end of the portal sleeve has entered the anatomical cavity, the safety shield 2363 will be moved distally causing operating member 2388 to engage a trigger 2426 in response to movement of the operating member toward the initial position or a trigger 2424 in response to movement of the operating member distally of the initial position to flex arm 2418 and release locking member 2422 from retraction plate 2394. Accordingly, retracting spring 2402 will move the distal part 2370 of the penetrating member proximally relative to the end part 2372 to a retracted position. By arranging the operating member 2388 to be engaged by the retraction plate 2394, the safety shield 2363 can be moved to a retracted position with the penetrating member. Push member 2371 can be utilized to set the instrument in the extended position via squeezing operation of end cap 2406 causing distal movement of the safety shield and, via engagement of operating member 2388 with retraction plate 2394, the penetrating member.

Yet another modification of an automatic retractable safety penetrating instrument according to the present invention is illustrated at 2460 in FIG. 56. Penetrating member 2462 for automatic retractable safety penetrating instrument 2460 is similar to penetrating member 1862 being made up of a distal part 2470 and an end part 2472 with the distal part including a distal end 2476, a body 2474 and a neck 2554. End part 2472 terminates proximally at a retraction plate 2494 disposed in hub 2466, and a retraction spring 2502 is connected between the retraction plate and the rear wall of the hub to bias the end part in a proximal direction. A locking and releasing mechanism 2512 similar to locking and releasing mechanism 1912 is disposed in hub 2466 for locking the retraction plate 2494 against a front wall of the hub in an extended position for the instrument illustrated in FIG. 56. Locking and releasing mechanism 2512 is mounted in end cap 2506 to serve as a push member for setting the instrument in an extended position, and an additional push member 2471 can be mounted in end cap 2506 for use in moving the end part 2472 distally when setting the instrument in the extended position. A plurality of internal walls or shoulders 2552' are disposed within end part 2472 with the walls 2552 having openings therein allowing passage therethrough by the neck 2554. Neck 2554 terminates proximally at an operating member or flange 2488 disposed in hub 2466. A helical coil operating spring 2498 is concentrically disposed around neck 2554 and connected between the neck and a wall 2552' of the end part to bias the distal part 2470 in a distal direction. More than one operating spring can be provided; and, as shown in FIG. 56, two operating springs 1498 are provided with each operating spring connected between the neck 2554 and an internal wall 2252'. A cushion spring 2500 is disposed concentrically around the neck 2554 and connected between body 2474 and a wall 2552' to bias the distal part in a proximal direction such that operating flange 2488 is maintained in an initial position disposed proximally of trigger 2524 and distally of triggers 2526 with the instrument in the extended position. Protrusions in the form of nubs or pins 2545' are provided on neck 2554 for use in mounting the operating and cushion springs between the neck 2554 and the internal walls 2552' and for compressing or collapsing the springs upon movement of the distal part in a proximal direction.

In use, the automatic retractable safety penetrating instrument 2460 is forced through tissue causing distal part 2470 to be moved proximally relative to end part 2472 such that operating member 2488 is moved proximally of the initial position to a set position, the nubs 2545' collapsing the operating and cushion springs along the neck 2554. With the operating member in the set position, shoulder 2480 will be in abutment with stop 2492, and the instrument will be in an operative position. Once a distal end of the portal sleeve 2464 has entered the anatomical cavity, the distal part 2470 will be moved distally causing operating member 2488 to move toward the initial position to engage trigger 2526 or distally of the initial position to engage trigger 2524 and flex arm 2518 thusly releasing the retraction plate 2494.

An additional modification of an automatic retractable safety penetrating instrument is illustrated in FIG. 57 at 2560. Instrument 2560 is similar to automatic retractable safety penetrating instrument 2460 except that neck 2654 for automatic retractable safety penetrating instrument 2560 is offset from and not aligned with a longitudinal axis of the instrument as is neck 2554 for instrument 2460. The retraction member for instrument 2560 is formed as an internal wall or shoulder 2652' extending inwardly from an inner surface of the wall of the end part 2572 to be engaged, within the end part, by locking member 2622, the retraction member having an opening therein allowing passage therethrough by the neck 2654. End part 2572 terminates proximally at a retraction plate or flange disposed in hub 2566 with retracting springs 2602 connected between the retraction plate and a rear wall of the hub to bias the end part in a proximal direction. Accordingly, in the automatic retractable safety penetrating instrument 2560, the locking member 2622 engages the retraction member, wall 2652', and not the retraction plate 2594 to hold the end part 2572 against proximal movement. Locking and releasing mechanism 2612 for automatic retractable safety penetrating instrument 2560 is mounted in end cap 2606 for use as a push member, via engagement of locking member 2622 with wall 2652', for setting the instrument in an extended position. An additional push member 2571 is mounted in end cap 2606 for engaging retraction plate 2594 when setting the instrument in the extended position via squeezing operation of the end cap. In the automatic retractable safety penetrating instrument 2560, triggers 2624 and 2626 are disposed within the end part 2572 such that the length of hub 2566 can be minimized to be no larger than necessary to allow retraction of end part 2572. Neck 2654 terminates proximally at an operating member or flange 2588 disposed in end part 2572 with the operating member having an angled end to facilitate proximal movement past triggers 2626 and engagement of triggers 2624 or 2626 upon distal movement of the operating member. An additional internal wall 2652" is provided in end part 2572, with an operating spring 2598 disposed around neck 2654 and connected between the internal wall 2652" and the body 2574 to bias the distal part 2570 distally. A cushion spring 2600 disposed around neck 2654 is connected between the neck 2654 and wall 2652' to bias the distal part proximally such that the operating member is maintained at an initial position proximally of triggers 2624 and distally of triggers 2626 in the extended position illustrated in FIG. 57.

Operation of instrument 2560 is similar to that for automatic retractable safety penetrating instrument 2460. During penetration of tissue, distal part 2570 moves proximally relative to end part 2572 causing proximal movement of operating member 2588 past triggers 2626. Once a distal end of portal sleeve 2564 has entered the anatomical cavity, operating member 2588 will move distally engaging triggers 2624 or 2626 to flex arm 2618 and release the retraction member, wall 2652'. Accordingly, retracting springs 2602 move the end part 2572 and with it distal part 2570 to the retracted position.

Yet another modification of an automatic retractable safety penetrating instrument according to the present invention is illustrated at 2660 in FIG. 58. Penetrating member 2662 for automatic retractable safety penetrating instrument 2660 is similar to penetrating member 1862 and includes an end part 2672 and a distal part 2670 having a distal end 2676, a tubular or partly hollow or tubular body 2674 and a neck 2754. A retraction member engages the proximal end of distal part 2670 and includes a retraction plate 2694 disposed in hub 2664 with an extension 2697 extending distally from the retraction plate to terminate at a forward wall or end flange 2751 disposed in body 2674 with the extension 2697 being concentrically disposed in neck 2654. Neck 2654 terminates proximally at an operating member or flange 2688 disposed in end part 2672, and an operating spring 2698 is disposed concentrically around extension 2697 and connected between operating member 2688 and retraction plate 2694 to bias the distal part 2670 in a distal direction. A cushion spring 2700 is concentrically disposed around the extension 2697 and connected between the forward wall 2751 and an end wall 2752 of body 2674 to bias the distal part in a proximal direction such that operating member 2688 is maintained in an initial position with the instrument in the extended position as illustrated in FIG. 58. A retracting spring 2702 is disposed in hub 2664 and connected between the retraction plate 2694 and a rear wall of the hub to bias the retraction member in a proximal direction. Locking and releasing mechanism 2712 for automatic retractable safety penetrating instrument 2660 is made up of a linkage arrangement including a link arm 2718 having an end pivotally connected at a joint to a trigger 2724 including a trigger cam 2727 and a trigger leg 2729 and an opposite end pivotally connected at a joint to a link 2723' pivotally mounted in hub 2664. Link 2723' is disposed in engagement with the retraction plate in the extended position for the instrument illustrated in FIG. 58 and is mounted on a joint in hub 2664 to rotate, such as in a counterclockwise direction looking at FIG. 58, to be disposed out of the path of longitudinal movement of retraction plate 2694 in response to proximal movement of link arm 2718. A locking arm 2718' is pivotally mounted in the hub, such as along the hub rear wall, and is biased to a locked position wherein an end or finger 2822 of the locking arm engages a lateral or upper edge or side of the retraction plate 2694 to prevent proximal movement thereof. The locking arm 2718' can be biased to the locked position in various ways, such as by a spring at the joint mounting the arm 2718' along the hub rear wall. With the arm 2718' in the locked position, locking member 2822 will be disposed in the path of movement of link arm 2718. The linkage can be biased, such as with springs provided at one or more joints of the linkage, to rotate link 2723' to release retraction plate 2694 with arm 2718' preventing movement of the linkage due to the bias. Where the arm 2718' both engages the retraction plate and holds link 2723' thereagainst, redundant protection is provided.

Operation of automatic retractable safety penetrating instrument 2660 is similar to that previously described in that the distal part 2670 will be moved proximally relative to end part 2672 during penetration of tissue causing operating member 2688 to be moved proximally from the initial position to the set position. Once a distal end of the portal sleeve has entered the anatomical cavity, distal part 2670 will be moved distally relative to end part 2772 causing operating member 2688 to move distally of the initial position to engage trigger cam 2727 and pivot trigger leg 2729 clockwise looking at FIG. 58 moving link arm 2718 proximally to engage a nub 2710' on locking member 2822 such that the locking arm 2718' is moved laterally, i.e. in a direction transverse to the direction of proximal movement of link arm 2718 to be released from retraction plate 2694 allowing the distal part 2670 of the penetrating member to be moved relative to the end part 2672 to a retracted position.

An additional modification of an automatic retractable safety penetrating instrument according to the present invention is illustrated in FIG. 59 at 2760. Penetrating member 2762 for automatic retractable safety penetrating instrument 2760 is similar to penetrating member 2362 except that body 2774 for penetrating member 2762 is hollow or tubular or partly hollow or tubular to receive the forward wall 2851 of the retraction member and the end part 2772 of the penetrating member is secured in or formed with a front wall of hub 2766. The retraction member for instrument 2760 includes forward wall 2851, retraction plate 2794 disposed in hub 2766 and a side or connecting member 2853 joining the retraction plate to the forward wall with neck 2854 of distal part 2770 extending through the connecting member to terminate proximally at an operating flange 2788 disposed in end part 2772. An operating spring 2798 is connected between the forward wall 2851 and an end wall 2852 of body 2774 to bias the distal part in a distal direction, and a cushion spring 2800 is disposed around neck 2854 and connected between forward wall 2851 and an internal shoulder or abutment 2780 of body 2774 to bias the distal part in a proximal direction such that operating member 2788 is maintained in an initial position proximally of trigger 2824 with the instrument in the extended position illustrated in FIG. 59. A retracting spring 2802 is connected between retraction plate 2794 and a rear wall of hub 2766 to bias the retraction member in a proximal direction. A locking and releasing mechanism 2812 is disposed in end part 2772 and includes a linkage arrangement having a link arm 2818 pivotally connected at a joint at one end to a locking member 2822 engaged with a bent or angled portion of connecting wall 2853 to prevent movement of the retracting mechanism proximally. Arm 2818 is pivotally connected at a joint at an opposite end thereof to trigger 2824 pivotally mounted in the end part and including a trigger cam 2827 and a trigger leg 2829. A locking arm 2818' pivotally mounted at a joint along the rear wall of hub 2766 terminates distally at a locking member 2822' biased to engage the linkage to prevent proximal movement of link arm 2818 such that the locking member 2822 is maintained in engagement with the retraction member in the extended position for the instrument. The linkage can be biased to rotate locking member 2822 counterclockwise looking at FIG. 59 to release the retraction member with arm 2818' preventing movement of the linkage due to the bias.

When automatic retractable safety penetrating instrument 2760 is utilized to penetrate tissue and enter an anatomical cavity, distal part 2770 of penetrating member 2762 will be moved proximally during penetration of the tissue causing movement of operating member 2788 from the initial position to a set position. The distal part 2770 will be moved distally upon a distal end of the portal sleeve entering the anatomical cavity, and the operating member 2788 will be moved distally of the initial position to engage trigger cam 2827 causing rotation of trigger 2824 clockwise and movement of link arm 2818 proximally to engage nub 2810' moving locking arm 2818' in a direction transverse to the direction of proximal movement of arm 2818 such that the locking member 2822 is released from the retraction member. Accordingly, retracting spring 2802 will move the retraction member proximally carrying with it the distal part 2770 of the penetrating member to a retracted position.

An additional modification of an automatic retractable safety penetrating instrument according to the present invention is illustrated in FIG. 60 at 2860 wherein the operating spring and the retracting mechanism are in the nature of a linkage arrangement. Penetrating member 2862 for automatic retractable safety penetrating instrument 2860 includes a distal part 2870 terminating proximally at an operating member or flange 2888 disposed in hub 2866 and an end part 2872 terminating proximally at a retraction plate 2894 disposed in hub 2866. A linkage 2898 including a pair of links 2898' and 2898" pivotally connected to each other at a central joint is pivotally connected to the operating flange and the retraction plate at distal and proximal end joints. A spring mounted at the central joint rotationally biases the links 2898' and 2989" to a normal position wherein the operating members 2888 is maintained in an initial position and the junction of the distal part 2870 is disposed beyond the distal end of the portal sleeve by a distance equal to the spacing between shoulder 2880 and abutment 2892 in the extended position illustrated in FIG. 60. A cross link 2900' is pivotally connected to linkage 2898 at retraction plate 2894 and to a linkage 2902. Linkage 2902 includes a distal link 2902' pivotally connected at a joint to cross link 2900', a proximal link 2902" pivotally secured to a rear wall of the hub and a cross link 2902" pivotally connected to the distal and proximal links at joints. Linkage 2902 is biased, such as with springs at one or more joints of the linkage, to a collapsed condition with cross link 2900' moving end part 2872 proximally. A locking and releasing mechanism 2912 is disposed in hub 2866 and includes an arm 2918 having a plurality of teeth or barbs 2921 thereon for engaging distal link 2902' to lock the linkage 2902 in an expanded, non-collapsed position in the extended position for the instrument illustrated in FIG. 60 and a trigger 2926. Trigger 2926 has a trigger cam 2927 disposed proximally of the operating flange in the initial position and a bent trigger leg 2929 pivotally mounted in hub 2866 at 2929' to be disposed in abutment with retraction plate 2894 with the instrument in the extended position. Trigger leg 2929 is hinged, pivotal or made flexible at 2929" along a portion of the leg disposed along arm 2918 allowing a forward portion of the trigger leg to rotate, clockwise looking a FIG. 60, around pivot 2929' and a rearward portion of the trigger leg to rotate, counter-clockwise looking at FIG. 60, in response to counterclockwise rotation of trigger cam 2927. A push member 2871 is disposed in end cap 2906 for moving the linkage 2902, via engagement of protrusion 2928 with link 2902', distally to engage teeth 2921 when setting the instrument in the extended position.

During operation, automatic retractable safety penetrating instrument 2860 is forced through tissue causing proximal movement of distal part 2870 such that operating member 2888 is moved proximally by trigger cam 2927 without causing flexing of arm 2918. Once a distal end of the portal sleeve has entered the anatomical cavity, the distal part 2870 will be moved distally causing movement of operating member 2888 toward the initial position to engage trigger cam 2927 to bend or pivot trigger leg 2929 at 2929" causing trigger-leg 2929 to rotate around pivot 2929' to be disposed out of the path of movement of retraction plate 2894 and arm 2918 to be flexed in a direction outwardly from a longitudinal axis of the instrument such that link 2902' is released from the barbs causing the linkage 2902 to move to a collapsed position carrying end part 2872 and with it distal part 2870 to a retracted position.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. An automatic retractable safety penetrating instrument for introducing a sleeve into a cavity in the body comprising a sleeve for providing a passage through a cavity wall and having a distal end for positioning in the body cavity, a proximal end for positioning externally of the body cavity and a lumen extending between said distal and proximal ends;

a penetrating member disposed in said lumen of said sleeve and having a distal end for penetrating the cavity wall and terminating proximally at a hub;

a retracting mechanism for moving said distal end of said penetrating member proximally relative to said sleeve from an extended position where said distal end of said penetrating member protrudes beyond said distal end of said sleeve to a retracted position within said sleeve;

a locking and releasing mechanism for automatically actuating said retracting mechanism to move said distal end of said penetrating member to said retracted position in response to said distal end of said sleeve entering the body cavity; and control means carried by said hub for selectively disabling said locking and releasing mechanism to prevent automatic retraction of said distal end of said penetrating member from said extended position.

2. An automatic retractable safety penetrating instrument as recited in claim 1 and further comprising an elongate member movable longitudinally relative to said penetrating member and having a blunt distal end, and means biasing said elongate member distally toward an extended position where said blunt distal end protrudes beyond said distal end of said penetrating member, and wherein said control means includes means for selectively retracting said elongate member with said penetrating member when said penetrating member is automatically moved to said retracted position or maintaining said elongate member in said extended position when said penetrating member is moved automatically to said retracted position.

3. An automatic retractable safety penetrating instrument as recited in claim 2 wherein said elongate member is a probe passing through said penetrating member.

4. An automatic retractable safety penetrating instrument as recited in claim 2 wherein said elongate member is a shield disposed around said penetrating member.

* * * * *